US012697463B2

(12) United States Patent
Ayzenberg et al.

(10) Patent No.: US 12,697,463 B2
(45) Date of Patent: Aug. 4, 2026

(54) SLEEP ASSISTANCE THROUGH GENERATION AND EVALUATION OF GENERATIVE SLEEP CONTENT AND/OR SLEEP IMPROVEMENT INTERVENTIONS INCLUDING TRAINING, ADJUSTING, MEDIATING, AND/OR INTEGRATING OUTPUTS OF ONE OR MORE AI MODELS

(71) Applicant: Stealth Labs Inc., Brookline, MA (US)

(72) Inventors: Yadid Ayzenberg, Brookline, MA (US); Amir Lazarovich, Apex, NC (US); Michal Matuszczak, Warsaw (PL)

(73) Assignee: Stealth Labs Inc.

( * ) Notice: Subject to any disclaimer, the term of this patent is extended or adjusted under 35 U.S.C. 154(b) by 154 days.

(21) Appl. No.: 18/816,277

(22) Filed: Aug. 27, 2024

(65) Prior Publication Data

US 2026/0061152 A1 Mar. 5, 2026

(51) Int. Cl.
*A61M 21/02* (2006.01)
*G10L 13/027* (2013.01)
(Continued)

(52) U.S. Cl.
CPC ........... *A61M 21/02* (2013.01); *G10L 13/027* (2013.01); *G10L 15/22* (2013.01); *H04R 1/1016* (2013.01); *A61M 2205/52* (2013.01)

(58) Field of Classification Search
CPC .............. A61M 21/02; A61M 2205/52; A61M 2021/0022; A61M 2021/0027; A61M 2021/0044; A61M 2021/0083; A61M 2205/332; A61M 2205/3553; A61M 2205/505; A61M 2205/587; A61M 2209/088; A61M 2210/0612; A61M 2230/005; A61M 2230/04; A61M 2230/06; A61M 2230/10; A61M 2230/63; G10L 13/027; G10L 15/22; H04R 1/1016;
(Continued)

(56) References Cited

U.S. PATENT DOCUMENTS

2025/0050056 A1* 2/2025 Lee ...................... A61B 5/4812

FOREIGN PATENT DOCUMENTS

KR 2024038545 A 3/2024

* cited by examiner

*Primary Examiner* — Paul Kim
(74) *Attorney, Agent, or Firm* — Peter Jensen-Haxel

(57) ABSTRACT

Disclosed are a system, a device, and/or a method of sleep assistance through generation and evaluation of generative sleep content and/or sleep improvement interventions including training, adjusting, mediating, and/or integrating outputs of one or more AI models. In one embodiment, a system includes an earbud generating an audio generation request through a voice interface, which is parsed by a sleep assistance server to extract a narrative prompt. A generative content server inputs the narrative prompt into an artificial neural network to generate a text data, and then text-to-speech model to generate a narrative audio. A content integration routine may overlay the narrative audio data with additional music and/or physiological guidance data. A generative audio data is returned to the earbud to assist in achieving sleep. The system may evaluate physiological data to determine effectiveness of the sleep assistance audio, and may augment, fine-tune, and/or retrain one or more AI models.

13 Claims, 26 Drawing Sheets

(51) Int. Cl.
*G10L 15/22* (2006.01)
*H04R 1/10* (2026.01)

(58) Field of Classification Search
CPC .... A61N 1/36025; G16H 40/67; G16H 50/70; G16H 50/20; G16H 20/70; A61B 5/4806; A61B 5/4812
USPC .......................................................... 381/110
See application file for complete search history.

Sleep Evaluation and Assistance Network 199

Sleep Assistance Server 200

Processor 201

Memory 203

Sleep Assistance OS 110

Sleep Assistance Model 115

Base LLM 111

Text RAG Data 112

LLM Fine Tuning Model 114

Low Rank Adaptation 116

Speech-to-Text Model 218

Cognitive State Engine 204

State Monitoring Routine 206

State Determination Routine 208

Physiological Data 205

Request Agent 210

Content Request Parser 212

Sleep Improvement Request 170

Cont. Prompt Extraction Routine 214

Assistance Parser 216

Audio Generation Request 111

Sleep Session Engine 220

Sleep Metric Routine 222

Metric Reporting Routine 223

Improv. Reporting Subroutine 224

Session Summary Text 226

Session Summary Audio 228

Element Evaluation 230

Generative Element 232

Element Effectiveness Value 234

Element Effectiveness Rating 236

Sleep Assistance Engine 240

Query Submission Routine 242

Query Receipt Routine 244

Intervention Gen. Routine 246

Intervention Subroutine 248

Sleep Content Coordination Engine 270

Content Selection Routine 272

Effectiv. Selection Routine 274

Gen. Cont. Request Routine 276

Content Delivery Routine 278

Content Evaluation Engine 250

Content Effectiveness Routine 252

User Feedback Routine 253

Evaluation Storage Subroutine 254

Effectiv. Reporting Subroutine 255

Element Eval. Routine 256

Effectiveness Summary Text 257

Effectiveness Sum. Audio 258

General Sleep Metric Baseline Data 225

Intervention Evaluation Engine 260

Intervention Effectivness Routine 262

Intervention Qual. Routine 261

User Feedback Routine 263

Eval. Storage Subroutine 264

Effectiv. Reporting Subroutine 265

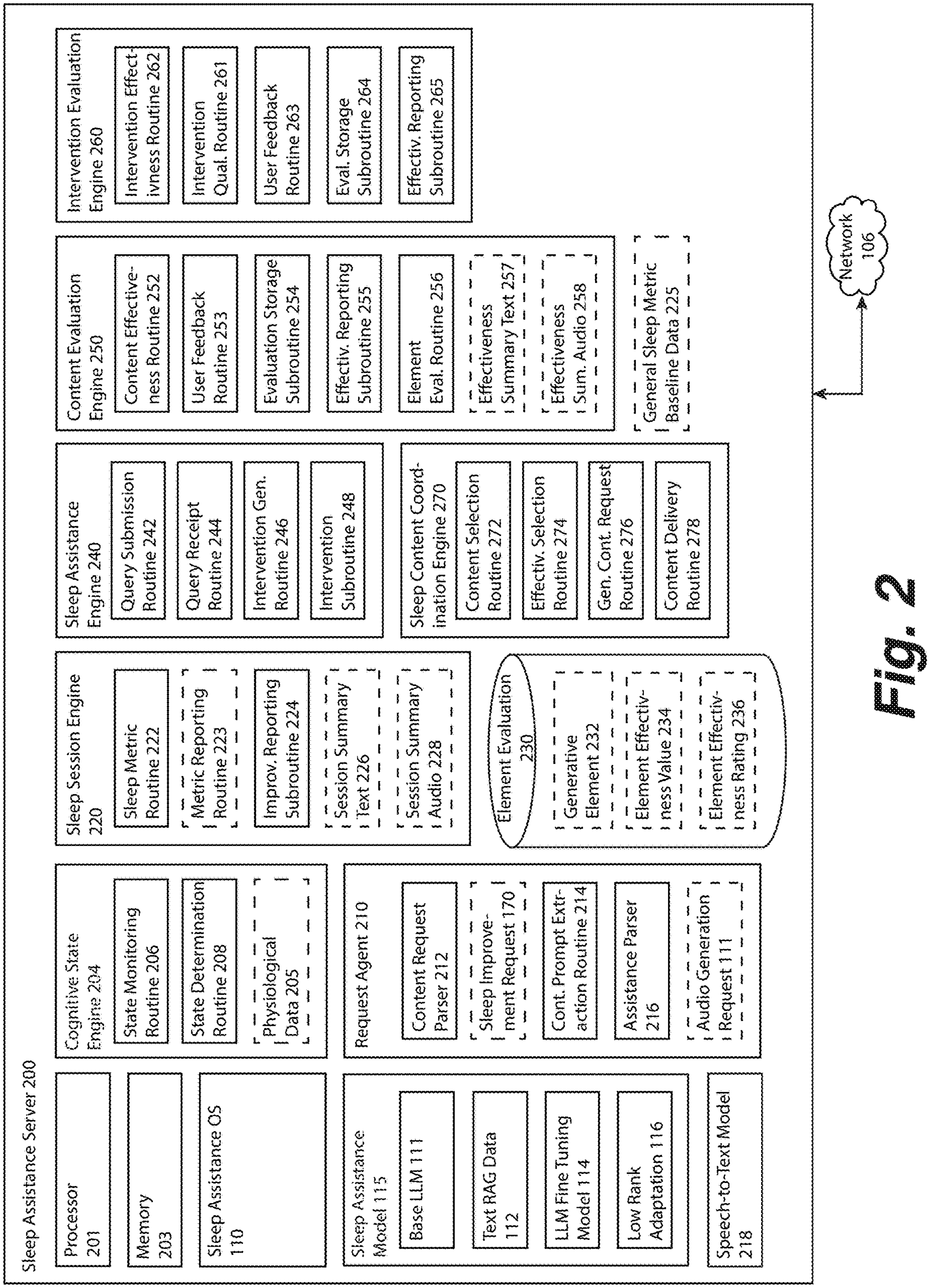

Fig. 2

Generative Content Server 300

Processor 301

Prompt Receipt Agent 304

Memory 303

Generative Content Engine 320

Effectiveness Guid. Model Routine 321

Recorded Query Routine 322

Threshold Value 323
Threshold Rating 325

Music Prompt Interpretation Routine 326

Guidance Prioritization Subroutine 328

Text-Audio Element Relation Sub. 329

Text Generation Routine 330

Voice Generation Routine 332

Music Generation Routine 340

Ambient Generation Routine 350

Phys. Guidance Routine 360

Model Augmentation System 370

General Augmentation Routine 372

Specific Augmentation Routine 374

Sleep Assistance Audio 102

Model Training Engine 390

Fine Tuning Routine 392

Content Integration Engine 380

Content Integration Model 382

Text Generation Model 130

Music Generation Model 140

Ambient Sound Gen. Model 150

Phys. Guidance Model 160

General Augment Narrative Data 134

General Augment Music Data 144

General Augment Ambient Data 154

Narrative Audio Data 832

Phys. Guidance Template 864

Text-to-Speech Model 192

Text Data 830

Text-Music Relation Model 352

Music Audio Data 840

Ambient Audio Data 000

Generative Sleep Content 800

Network 106

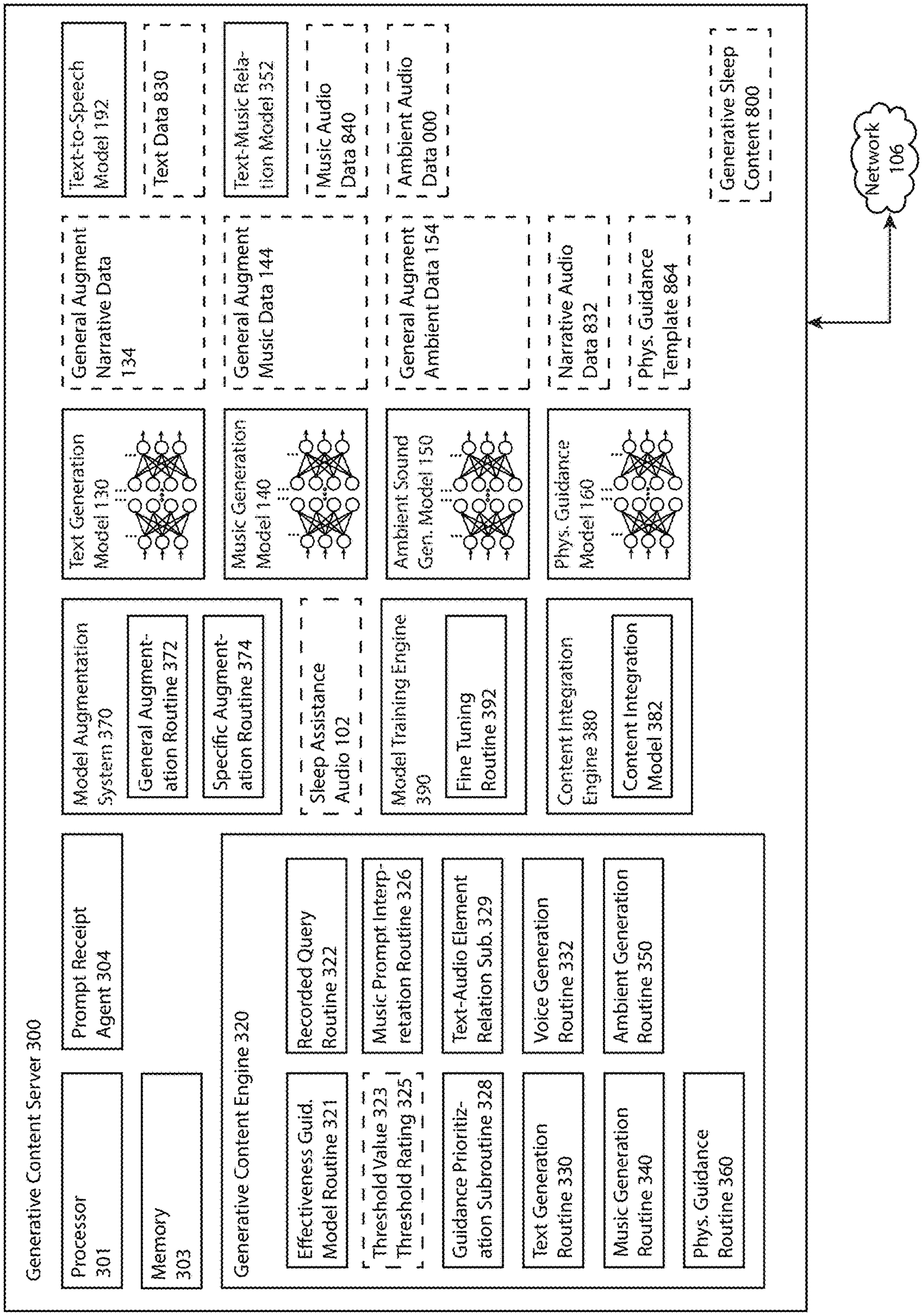

Fig. 3

Example Generative Prompt Extraction and Formation 799

Sleep Session Analysis Process Flow 1150

D

START

NARRATIVE REQUEST? 1800

YES

EXTRACT NARRATIVE PROMPT 1802

NO

EXTRACT MUSIC PROMPT 1808

YES

MUSIC REQUEST? 1806

DETERMINE NARRATIVE MODIFIERS 1804

NO

DETERMINE MUSIC MODIFIER 1810

AMBIENT REQUEST? 1812

YES

EXTRACT AMBIENT PROMPT 1814

NO

GENERATE MUSIC / AMBIENT PROMPT FROM OTHER PROMPT(S) 1820

YES

FORCE MUSIC / AMBIENT INCLUSION? 1818

DETERMINE AMBIENT MODIFIERS 1816

NO

PHYSIOLOGICAL GUIDANCE REQUEST? 1822

YES

EXTRACT PHYSIOLOGICAL GUIDANCE PROMPT 1824

NO

E

END

DETERMINE PHYSIOLOGICAL GUIDANCE MODIFIER 1826

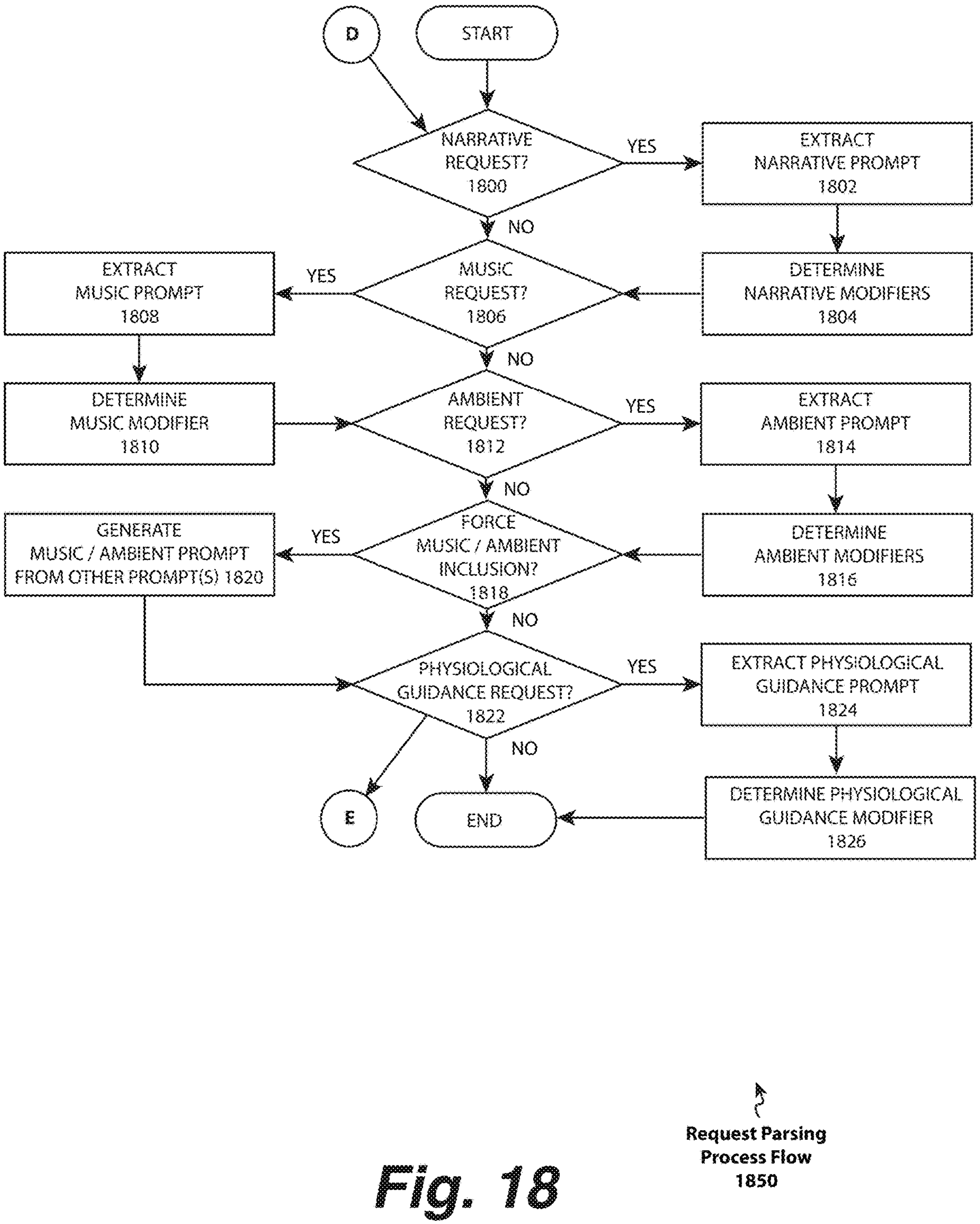

*Fig. 18*

START

5

PHYSIOLOGICAL GUIDANCE PROMPT? 2000

YES

F

NO

GENERATIVE CONTENT? 2002

YES

INPUT PHYS. PROMPT INTO PHYS. GUIDANCE TEMPLATE MODEL 2012

NO

GENERATE PHYS. GUIDANCE TEMPLATE 2014

UTILIZE RECORDED AUDIO DATA? 2004

NO

LOAD RECORDED PHYSIOLOGICAL GUIDANCE AUDIO 2006

OPTIONALLY ADD DESCRIPTION OF PHYSIOLOGICAL AUDIO TO CONTEXT WINDOW 2007

YES

SELECT PREEXISTING PHYS. GUIDANCE TEMPLATE 2008

LOAD PREEXISTING PHYS. GUIDANCE TEMPLATE 2010

OPTIONALLY ADD / TEXTUALIZE GUIDANCE TEMPLATE TO CONTEXT WINDOW 2016

6

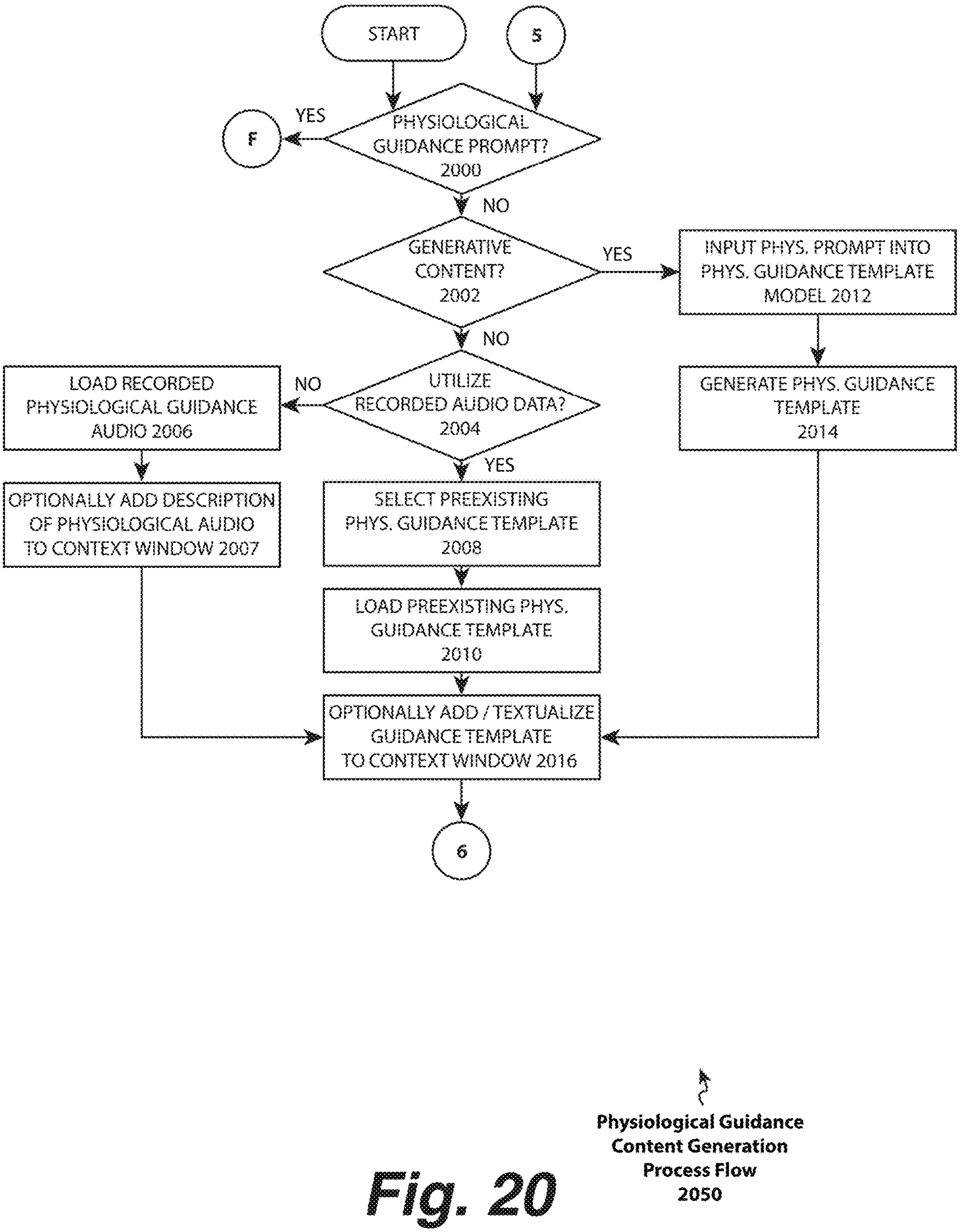

Fig. 20

START
8
H
UTILIZE MUSIC? 2300
NO
I
YES
SELECT RECORDED MUSIC AUDIO / MUSIC DESCRIPTION DATA 2304
NO
UTILIZE EXISTING MUSIC? 2302
YES
COMBINE WITH GENERATIVE DATA? 2205
YES
CONSTRAIN MUSIC TO PHYS. GUIDE? 2306
YES
GENERATE MUSIC CONSTRAINT FROM PHYS. GUIDANCE TEMPLATE 2308
NO
NO
INPUT MUSIC PROMPT INTO MUSIC GENERATION MODEL 2310
GENERATE MUSIC AUDIO DATA AND/OR MUSIC DESCRIPTION DATA 2312
LOAD MUSIC AUDIO DATA AND/OR MUSIC DESC. DATA INTO PENDING GENERATIVE AUDIO DATA 2314
END
9

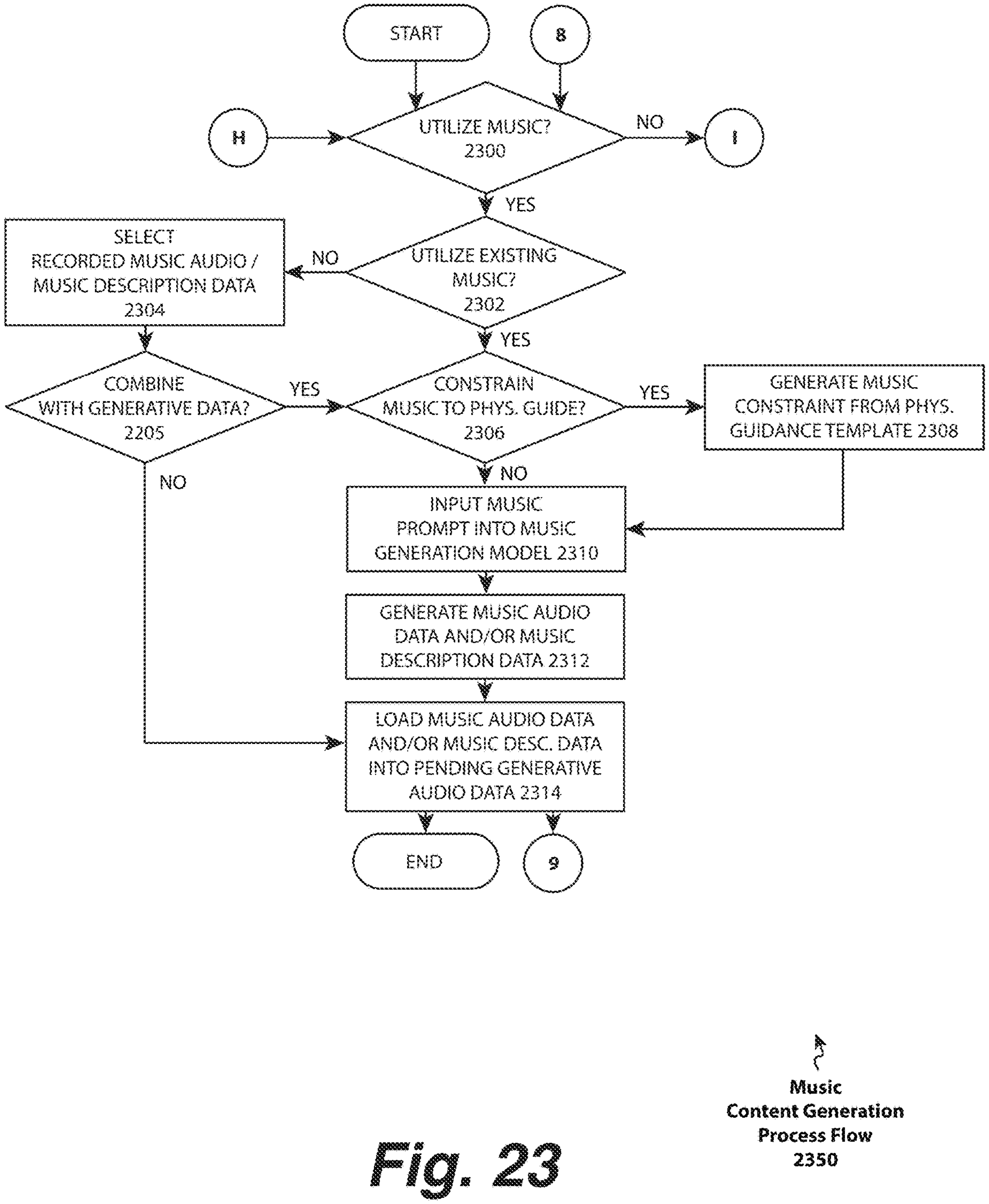

Fig. 23

Content Integration Process Flow 2450

SLEEP ASSISTANCE THROUGH GENERATION AND EVALUATION OF GENERATIVE SLEEP CONTENT AND/OR SLEEP IMPROVEMENT INTERVENTIONS INCLUDING TRAINING, ADJUSTING, MEDIATING, AND/OR INTEGRATING OUTPUTS OF ONE OR MORE AI MODELS

FIELD OF TECHNOLOGY

This disclosure relates generally to data processing devices and, more particularly, to a method, a device, and/or a system of sleep assistance through generation and evaluation of generative sleep content and/or sleep improvement interventions including training, adjusting, mediating, and/or integrating outputs of one or more AI models.

BACKGROUND

Sleep is an important part of health and wellbeing. However, it can be increasingly difficult for some people to achieve consistent, comfortable, and/or restful periods of sleep. This can especially be true because of the diversity of sleep environments, personal preferences, dependence on electronic devices, genetic tendencies, health conditions, and/or other individualized needs involving sleep.

While electronics can detract from sleep, certain technology has begun to assist users in tracking and improving sleep. For example, there are trackers (including in some smartphones) that can track user motion and may be used to determine periods of sleep and/or basic sleep metrics. Other similar devices may be worn on the wrist, in earbuds, or may even use detectors remote to the user, such as a bedside alarm clock or charging unit.

However, despite these advances, numerous challenges may still arise. The user may be able to see data explaining basic sleep metrics, but may not be able to know why they did or did not sleep well. Naturally, the user may have a difficulty self-evaluating because users attempting to sleep tend to try to decrease cognitive activity, rather than try to assess why they are having trouble sleeping. At the same time, outside observations are limited to only that data that can be collected through sensors and may not be able to be readily combined with internal information known to the user. As a result, many of the metrics and other information may not be actionable. It may also be difficult for a user to get answers to questions they may have, or combine what they know intuitively or factually with any physiological or other data gathered through technological means.

A common sleep aid may include auditory sound provided within the sleep environment of the user, and sometimes delivered directly to the ear of the user through headphones and/or earbuds. For example, some users have favorite music, podcasts, and/or ambient sounds ("babbling brooks," "crashing waves", "forest birds," etc.) that they listen to when falling asleep. Other audio can include broad spectrum sound (e.g., "white noise," "pink noise") and/or masking sounds capable of masking environmental noise.

Technology has also provided new means and unprecedented selection in content. However, while sleep may include some general considerations for selecting content (e.g., "calm" content) individual users may have specific needs or requirements when selecting sleep audio. As one example, a user may find that a certain audio track helps them sleep, but after hearing it too many times it may have the opposite effect. Rather, it may be the characteristics and/or elements of the audio track that are reliably and/or repeatedly conducive to aiding sleep. Those characteristics and/or elements may be difficult to identify or find in another audio track.

In some cases, the user may not even be aware of (or correct about) which content actually assist in inducing or maintaining sleep. Similarly, the user may not understand why certain audio tracks induce or maintain sleep, while others do not. Users respond differently to various audio sounds, music, and/or ambient sound, and the response may be both conscious and unconscious. Determining the effectiveness of any sound may be further complicated by the numerous other environmental factors (e.g., noise when traveling in a hotel), the subjective mind state of the user (e.g., anxiety), and/or health (e.g., the user has a cold and is in discomfort).

Good and/or sufficient sleep can also be seen as having economic value (e.g., for self-productivity and health). There is a continuing need for new technologies that assist users in achieving consistent, comfortable, restful, and/or quality sleep, especially technologies that may be adaptable to the sleep needs, environments, and/or circumstances of individuals.

A promising technology applicable to many industries and disciplines are artificial intelligence models ("AI models) and/or machine learning ("ML") techniques, including artificial neural networks and ML retraining. For example, large language models (LLMs) are useful for responding to a variety of questions posed by a user through the generation of predictive text. Some AI models are generative, for example able to generate narrative text, sound, and even music.

However, numerous challenges may still exist in selecting, adapting, training, utilizing, and retraining these models. For example, because many AI-based technologies involve hidden layers of processing nodes, each with varying weights that are adjusting during training, and/or transformers, as known in the art, challenges may exist in formulating an input (and/or "prompt") to control the output. Also, AI-based models may sometimes work well when specialized, but may begin to produce strange or useless results when significantly broadened to encompass too many capabilities. Utilizing two or more specialized AI models may be possible. However, coherently coordinating the AI models and integrating the outputs and/or products may also pose a challenge. Efficiency challenges exist in determining when and how to "engineer" prompts, supplement prompts, add context to prompts with outside information, fine tune models, and/or custom train models. Finally, challenges may exist in measuring and responding to the effectiveness of model outputs.

New systems, devices, and/or methods are needed for making AI-based technologies more efficient and/or effective, including as they relate to the generation of sound and/or analysis of information that could assist in inducing or maintaining sleep.

SUMMARY

Disclosed are a method, a device, and/or a system of sleep assistance through generation and evaluation of generative sleep content and/or sleep improvement interventions 180 including training, adjusting, mediating, and/or integrating outputs of one or more AI models. In one embodiment, a system for generating customized audio for increasing effectiveness of relaxation and/or sleep includes a network, an earbud wearable by a user, a sleep assistance server, and a generative content server. The earbud includes a speaker, a microphone, a processor of the earbud, a memory of the earbud that is a non-transient computer readable memory of the earbud, and a wireless network interface controller communicatively coupled to the network. The earbud includes a request generation routine that includes computer readable instructions that when executed on the processor of the earbud generate an audio generation request through a voice interface implemented on the speaker and the microphone.

The sleep assistance server is communicatively coupled to the network and may include a processor of the sleep assistance server and a memory of the sleep assistance server that is a non-transient computer readable memory of the sleep assistance server.

The sleep assistance server includes a request agent including computer readable instructions that when executed receive an audio generation request through the voice interface. The sleep assistance server also includes a content prompt extraction routine comprising computer readable instructions that when executed: (i) parse the audio generation request to extract a narrative prompt, and store the narrative prompt in the memory of the sleep assistance server.

The generative content server is communicatively coupled to the network and includes a processor of the generative content server, a memory of the generative content server, a text generation routine, a voice generation routine, a content integration routine, and a generative content engine. The text generation routine includes computer readable instructions that when executed input the narrative prompt into a text generation model comprising an artificial neural network of the text generation model and generate a text data as the output of the artificial neural network of the text generation model. The artificial neural network includes a plurality of nodes comprising a set of input nodes, a set of hidden nodes, and a set of output nodes.

The voice generation routine includes computer readable instructions that when executed input the text data into a text-to-speech model and store a narrative audio data as an output of the text-to-speech model. The content integration routine includes computer readable instructions that when executed generate a generative audio data comprising an overlay of the narrative audio data and a music audio data, a physiological guidance data, and/or an ambient audio data. The generative content engine includes computer readable instructions that when executed transmit the generative audio data to the earbud of the user to assist the user in achieving at least one of relaxation and sleep through the customized audio.

The earbud may include an inertial measurement unit and a physiological signal agent that includes computer readable instructions that when executed gather a physiological data of the user from the inertial measurement unit of the earbud worn by the user while the generative audio data plays sound on the speaker of the earbud. The physiological data may include amotion of the user comprising a heartbeat, a respiration, and/or a macro movement.

The sleep assistance server may further include a state monitoring routine, a sleep metric routine, and/or a sleep content evaluation routine. The state monitoring routine that includes computer readable instructions that when executed utilize the physiological data gathered from the inertial measurement unit to determine the user is in at least one of a sleep state and an awake state over a time period.

The sleep metric routine may include computer readable instructions that when executed determine one or more sleep metrics for a sleep session that may include a sleep onset latency value, a length of a sleep period during the time period, a ratio of the sleep period to an awake period during the time period, a number of REM periods, a length of REM periods, a number of Non-REM periods, a length of Non-REM periods, a number of interstitial awake periods, and/or a length of the awake period during the time period.

The sleep content evaluation routine may include computer readable instructions that when executed extract one or more generative elements of at least one of the narrative audio data and the text data associated with the narrative audio data, and store one or more generative elements in association with an effectiveness value and an effectiveness rating based on the one or more sleep metrics.

The generative content server may include a general augmentation routine that includes computer readable instructions that when executed (i) query a general augment data that includes a general augment narrative data, a general augment music data, a general augment ambient data, and/or a general augment voice data; (ii) extract a subset of the general augment data based on textual association with the audio generation request, and (iii) load the subset of the general augment data into an input prompt of an artificial neural network and/or a context window of the artificial neural network. The input prompt may include at least one of the narrative prompt, the music prompt, and the ambient prompt. The artificial neural network may include an artificial neural network of the text generation model.

The generative content server may also include a specific augmentation routine that includes computer readable instructions that when executed (i) query a user specific augment data that includes a user augment narrative data, a user augment music data, a user augment ambient data, and/or a user augment voice data, (ii) extract a subset of the user specific augment data relevant to the audio generation request, (iii) overwrite at least some of the subset of the general augment data within the input prompt of the artificial neural network and/or a context window of the artificial neural network, and (iv) load the subset of the user specific augment data into the input prompt of the artificial neural network and/or the context window of the artificial neural network.

The generative content server may include a model training routine that may include computer readable instructions that when executed retrain the artificial neural network of the text generation model based on the effectiveness value and/or the effectiveness rating. The retraining may include adjusting a parameter of at least one of the artificial neural network of the text generation model. Adjusting the parameter comprising modifying a node weight of an ANN node, and tuning the parameter adjusts a weight value of at least one node of the set of input nodes, the set of hidden nodes, the set of output nodes. The text generation model may include a large language model. The text data input into a voice synthesizer comprising a custom voice model. The generative content server may also include a guidance prioritization subroutine comprising computer readable instructions that when executed constrain the output of the artificial neural network of a narrative generation model to produce the text data in which a text clause of the text data is temporally associable with a physiological guidance element of a physiological guidance template. The text-to-speech model may generate the narrative audio such that a voiceover of the text data is temporally associated with a physiological guidance element.

In another embodiment, a method includes gathering physiological data from a user from a sensor of the earbud and initiating a sleep session data. The method may furthermore include monitoring a cognitive state of the user for a time period, where the sleep state is determined based on a respiration rate, a respiration rate variability, a respiration rate curve, a heartrate, a heartrate variability, and/or a heartrate curve. The method in addition includes determining the user is in a sleep state based on the physiological data, then determining the user is in the concerned awake state based on the physiological data. The method may calculate one or more sleep metrics having a sleep onset latency value, a length of a sleep period during the time period, a ratio of the sleep period to an awake period during the time period, a number of REM periods, a length of REM periods, a number of Non-REM periods, a length of Non-REM periods, a number of interstitial awake periods, and/or a length of the awake period during the time period. The method furthermore includes reporting the one or more sleep metrics to the user through a voice interface using a speaker of the earbud upon a determination the user is in the concerned awake state, as a result assisting the user in evaluating the sleep effectiveness. Other embodiments of this aspect include corresponding computer systems, apparatus, and computer programs recorded on one or more computer storage devices, each configured to perform the actions of the methods.

Implementations may include one or more of the following features. The method may include: receiving a first user request for a sleep assistance audio; initiating the sleep assistance audio generated from a first audio data on an earbud worn by an user, determining an effectiveness value of the sleep assistance audio utilizing at least one of the sleep metrics of the time period compared against at least one of a general sleep metric baseline and an user baseline sleep metric generated with data having one or more previous time periods; querying the user for an effectiveness rating of the sleep assistance audio over at least one of the time period and a segment of the time period; receiving the effectiveness rating from the user; and generating a sleep audio effectiveness data by associating (i) at least one of the effectiveness value and the effectiveness rating and (ii) at least one of an identifier of the first audio data and an element of the first audio data; and storing the sleep audio effectiveness data association with an user profile of the user. The method may include: receiving a second user request for the sleep assistance audio; determining that at least one of that the effectiveness value is below a threshold value and the effectiveness rating is below a threshold rating; and initiating the sleep assistance audio generated from a second audio data on the earbud worn by the user. The method may include: receiving a second user request for the sleep assistance audio; parsing the second user request to determine a requested element of the sleep assistance audio of the second user request; generating a prompt from the second user request for at least one of selection of the sleep assistance audio and generation of the sleep assistance audio; initiating a retrieval augmented generation data, referred to as a session RAG, for use in association with the sleep session; querying the user profile and loading a description of the first audio data and at least one of the effectiveness rating and the effectiveness value into the session RAG; and submitting the prompt and the session RAG to a large language model having an artificial neural network. The method may include: inputting into an artificial neural network at least one of (i) the sleep data, and (ii) the one or more sleep metrics, where the artificial neural network at least one of trained with and fine-tuned with data having one or more sleep improvement interventions 180 associated with at least one of sleep data and a set of sleep metrics; outputting a first sleep improvement intervention 180 of the one or more sleep improvement interventions 180; determining the user is initiating the sleep session; reporting the sleep recommendation to the user through a voice interface using a speaker of the earbud, where the first sleep improvement intervention 180 having at least one of a decreased environmental noise, an increased sleep period, an earlier sleep time, a later awakening time, and utilization of a different audio data to generate the sleep assistance audio. The method may include: receiving a sleep improvement request from the user, where the sleep improvement request received through a voice interface of an earbud worn by the user; generating a prompt having data extracted from the sleep improvement request; submitting the prompt to a large language model having an artificial neural network of a sleep assistance model, where the artificial neural network of the sleep assistance model at least one of trained with and fine-tuned with a training data having a text question related to sleep effectiveness paired with a text answer related to sleep effectiveness. receiving an output from the ANN of the sleep assistance model having a predictive text of the sleep assistance model; and providing the predictive text of the sleep assistance model to the user through the voice interface as a second sleep intervention. The method may include: reporting the effectiveness value to the user upon determination the user is in the concerned awake state; generating a summary text data of the one or more sleep metrics; inputting the summary text into a text-to-speech model; generating a summary audio; and transmitting the summary audio to the earbud worn by the user, where the sleep assistance audio generated from at least one of a music audio data, a physiological guidance template, a narrative audio data, and an ambient sound data, where the sleep assistance audio may include a generative audio that is output from an artificial neural network of a text generation model, an artificial neural network of a music generation model, and an artificial neural network of an ambient sound generation model, and where the sleep session persists until an automatic determination of the concerted awake state. Implementations of the described techniques may include hardware, a method or process, or a computer tangible medium.

In another embodiment, a method may include receiving an audio generation request through a voice interface collected on a microphone of an earbud. The method may also include parsing the audio generation request to extract a narrative prompt and a physiological guidance prompt. The method may furthermore include storing the narrative prompt in a computer readable memory. The method may in addition include determining a narrative modifier from the audio generation request having at least one of a narrative style description and a narrative genre description. The method may moreover include inputting the narrative prompt into a text generation model having an artificial neural network of the text generation model. The method may also include generating a text data as the output of the artificial neural network of the text generation model. The method may furthermore include inputting the text data into a text-to-speech model. The method may in addition include outputting a narrative audio data. The method may moreover include storing the physiological guidance prompt in the computer readable memory. The method may also include determining a physiological guidance modifier from the audio generation request having a physiological guidance type, where the physiological guidance type having at least one of a respiration rate, a respiration pattern, and a heart rate. The method may furthermore include inputting the physiological guidance prompt into a physiological guidance model having an artificial neural network of the physiological guidance generation model. The method may in addition include generating a physiological guidance template as an output of the artificial neural network of the physiological guidance model, where the physiological guidance having one or more physiological. The method may moreover include generating the generative audio data having an overlay of the narrative audio data and audio generated from the physiological guidance template. The method may also include transmitting the generative audio data to the earbud of the user to assist the user in achieving at least one of relaxation and sleep through the customized audio. Other embodiments of this aspect include corresponding computer systems, apparatus, and computer programs recorded on one or more computer storage devices, each configured to perform the actions of the methods.

Implementations may include one or more of the following features. The method may include: parsing the audio generation request to further determine if a music prompt is included within the audio generation request; generating, if the music prompt was not present when the audio generation request was parsed, the music prompt by inputting the narrative prompt into a text-music relation model relating a text to at least one of musical elements, a music style description, and a music genre description, optionally extracting a music modifier having at least one of a music filter, the music style description, and the music genre description; storing in the computer readable memory the music prompt and optionally at least one of the music style description, the music genre description, and the music filter; inputting the music prompt into a music generation model having an artificial neural network of the music generation model, where the music generation model trained with training data having associations between text tokens and musical elements; generating a music audio data as an output of the artificial neural network of the music generation model, where the generative audio data may include an overlay of the music audio data. The method may include: parsing the audio generation request to further determine an ambient sound prompt; storing the ambient sound prompt in the computer readable memory; receiving an ambient modifier having at least one of an ambient filter and an ambient style description; inputting the ambient sound prompt and the ambient modifier into an ambient sound generation model having an artificial neural network of the ambient sound generation model, where the ambient sound generation model trained with training data having associations between text tokens and sound elements; generating the ambient audio data as an output of the artificial neural network of the ambient generation model, where the generative audio data may include an overlay of the ambient audio data. The method may include: querying a general augment data having at least one of general augment narrative data, general augment music data, general augment ambient data, and general augment voice data; extracting a subset of the general sleep model augment data based on textual association with the audio generation request; loading the subset of the general augment data into at least one of an input prompt of an artificial neural network and a context window of the artificial neural network, where the input prompt is at least one of the narrative prompt, the music prompt, and the ambient prompt, and where the artificial neural network is at least one of an artificial neural network of the text generation model, an artificial neural network of the music generation model, and an artificial neural network of the ambient sound generation model. The method may include: querying an user specific augment data having at least one of user augment narrative data, user augment music data, user augment ambient data, and user augment voice data, extracting a subset of the user specific augment data relevant to the audio generation request; overwriting at least some of the subset of the general augment data within at least one of the input prompt of the artificial neural network and the context window of the artificial neural network; and loading the subset of the user specific augment data into at least one of the input prompt of the artificial neural network and the context window of the artificial neural network. The method may include: constraining the output of the artificial neural network of the ambient sound generation model to produce an ambient audio data in which an ambient element is temporally associated with a physiological guidance element; constraining the output of the artificial neural network of the music generation model to produce the music audio data in which a musical element is temporally associated with a physiological guidance element; and constraining the output of the artificial neural network of the text generation model to produce the text data in which a text clause of the text data is temporally associable with a physiological guidance element, where the text-to-speech model generates the narrative audio such that a voiceover of the text data is temporally associated with a physiological guidance element. The method may include: gathering a physiological data of the user from a sensor of an earbud worn by the user while the generative audio data plays sound on a speaker of the earbud; determining the user is in a sleep state; determining one or more sleep metrics having a sleep onset latency value, a length of a sleep period during the time period, a ratio of the sleep period to an awake period during the time period, a number of REM periods, a length of REM periods, a number of Non-REM periods, a length of Non-REM periods, a number of interstitial awake periods, and a length of the awake period during the time period; extracting one or more generative elements of at least one of the generative audio data, the narrative audio data, the narrative text data associated with the narrative audio data, the music audio data, the ambient audio data, and the one or more physiological guidance elements; storing the one or more generative elements in association with an effectiveness value and an effectiveness rating; retraining at least one of the artificial neural network of the text generation model, the artificial neural network of the music generation model, the artificial neural network of the physiological guidance model and the artificial neural network of the ambient generation model, where retraining may include adjusting a parameter of at least one of the artificial neural network of the text generation model, the artificial neural network of the music generation model, and the artificial neural network of the physiological guidance model and the artificial neural network of the ambient generation model, and where adjusting the parameter having modifying a node weight of an ANN node. The method may include: querying a prerecorded audio having at least one of a recorded narrative audio, a recorded music audio, a recorded ambient audio, and a recorded physiological guidance audio, and integrating the prerecorded audio with the generative audio, where the artificial neural network each having a plurality nodes having a set of input nodes, a set of hidden nodes, and a set of output nodes, where tuning the parameter adjusts a weight value of at least one node of the set of input nodes, the set of hidden nodes, and the set of output nodes, where the text generation model is a large language model, and where the narrative text data input into a voice synthesizer having a custom voice model. Implementations of the described techniques may include hardware, a method or process, or a computer tangible medium.

BRIEF DESCRIPTION OF THE DRAWINGS

The embodiments of this disclosure are illustrated by way of example and not limitation in the figures of the accompanying drawings, in which like references indicate similar elements and in which:

FIG. 2 illustrates the sleep assistance server of FIG. 1, including the sleep assistance OS, a cognitive state engine for determining a sleep state of the user from physiological data, a request agent for parsing requests and generating prompts as model inputs, a sleep session engine for determining sleep metrics, a content assistance engine, a content evaluation engine for determining effectiveness of preexisting and/or generative content or elements thereof, and/or an intervention evaluation engine for determining effectiveness of interventions, according to one or more embodiments.

FIG. 3 illustrates the generative content server of FIG. 1 for generating a sleep assistance audio, including a generative content engine usable to parse inputs, select, and control one or more generative models, including for example a text generation model, a physiological guidance model, a music generation model, and/or an ambient sound generation model, according to one or more embodiments.

FIG. 18 illustrates a generative request parsing process flow, including as may be utilized in conjunction with the generative request processing process flow of FIG. 17, according to one or more embodiments.

FIG. 20 illustrates a physiological guidance content generation process flow, according to one or more embodiments.

FIG. 23 illustrates a music content generation process flow, according to one or more embodiments.

Other features of the present embodiments will be apparent from the accompanying drawings and from the detailed description that follows.

DETAILED DESCRIPTION

Disclosed are a method, a device, and/or system of sleep assistance through generation and evaluation of generative sleep content and/or sleep improvement interventions 180 including training, adjusting, mediating, and/or integrating outputs of one or more AI models. Although the present embodiments have been described with reference to specific example embodiments, it will be evident that various modifications and changes may be made to these embodiments without departing from the broader spirit and scope of the various embodiments.

Figure 1A:
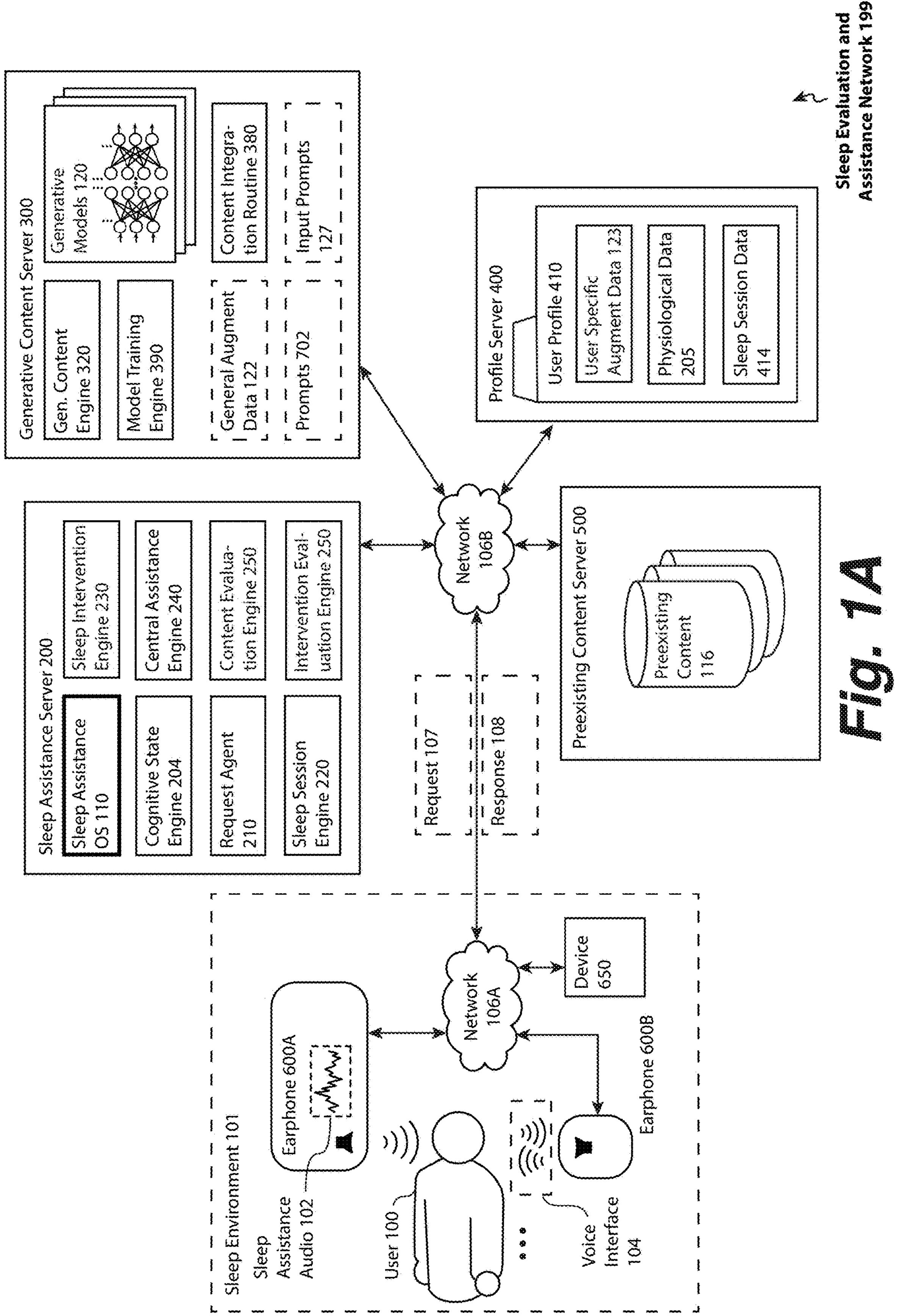
FIG. 1A illustrates a sleep evaluation and assistance network in which sleep of a user can be analyzed, sleep assistance audio generated, and requests for sleep assistance resolved, including a sleep assistance server for providing analysis and generating sleep improvement interventions and a generative content server including communicative coupling to one or more generative models configured to generate physiological guidance, narrative text or audio, music description or audio, and/or ambient sound descriptions or audio, and as each such function, AI-based models, and/or elements thereof may be mediated and coordinated by a sleep assistance operating system (sleep assistance OS), according to one or more embodiments.

FIG. 1 illustrates a sleep evaluation and assistance network 199 usable to assist a user 100 with sleep, according to one or more embodiments. The user 100 may desire to achieve deep sleep, sustained sleep, rapid onset of sleep, and/or other beneficial sleep objectives. The user 100 may be faced with a variety of both internal and external (and/or physical and mental) constraints, challenges, and/or disruptions that may inhibit onset of sleep, cause light sleep, amplify the disturbance of environmental noise or discomfort, etc.

In one or more embodiments, the user 100 may desire a sleep assistance audio 102 to assist the user 100 in initiating or maintaining sleep. In a simple example, the sleep assistance audio 102 may include traditional prerecorded soundtracks, e.g., the recorded music audio 540. However, in a more complex example, and as shown and described throughout the present embodiments, the sleep assistance audio 102 may include generative sleep content 800 which may be proposed by the user 100 and/or automatically formulated and generated. The generative sleep content 800 may include, for example, custom and/or tailored elements based on favorable characteristics for sleep identified for the particular instance of the user 100 and/or a population of users 100. The generative content may also include content or elements thereof previously measured for effectiveness in improving sleep metrics, either for a user 100 and/or a wider population of users 100. In one or more embodiments, and as further shown and described throughout the present embodiments, the sleep assistance audio 102 may include a generative audio that is output from an artificial neural network of a text generation model 130, an artificial neural network of a music generation model 140, and an artificial neural network of and/or an ambient sound generation model 150, including possible physiological guidance such as respiration control cues overlayed and/or incorporated into each possible generative category.

The sleep assistance audio 102 may then be played for the user 100 on one or more speakers, feedback and physiological data gathered and evaluated for effectiveness, and the results utilized to inform the user 100 to improve future sleep assistance audio 102. Effectiveness evaluations may also be utilized to prompt-engineer, guide, and/or retrain generative models for the benefit of the user 100 and other users 100.

In one or more embodiments, the sleep assistance audio 102 may be played on a speaker within the sleep environment 101. In one or more preferred embodiments, the speaker may be included within an earphone 600. The earphones 600 may be instantiated as an earbud to minimize discomfort and provide additional sound masking during sleep. The earphone 600 may further include a microphone which may gather sound from the user 100. The sound from the user 100 may include speech for interacting with and/or controlling the sleep evaluation and assistance network 199 and components thereof, for example implementing a voice interface 104. (In one or more embodiments, the microphone may also help to implement the physiological sensors 612, as shown and described in conjunction with FIG. 6, and throughout the present embodiments).

The user 100 may generate a request 107 for sleep assistance, for example through a smartphone application (e.g., an "App") or, in one or more preferred embodiments, through the voice interface 104. Use of the voice interface 104 may assist in lowering a cognitive load on the user 100 during interactions, such as requesting assistance and/or providing feedback to the sleep evaluation and assistance network 199. For example, the user 100 may keep their eyes closed, preventing light from entering the retina which can disrupt sleep.

The request 107 may include multiple forms of requested assistance, including a generative sleep content request 700 and/or, as further described below, a sleep improvement request 170. In one or more embodiments, the request 107 may include a generative sleep content request 800 including at least one or more aspects of audio content generated in response to the request of the user 100, including in real time. The generative sleep content request 800 may include a request for a narrative story (e.g., a "sleep story"), music, ambient sound (e.g., nature sounds, environmental sounds, other ambience). The generative sleep content request 800 may also include and/or incorporate (e.g., into structure or content of the narrative, music, and/or ambience) physiological guidance, as may be useful to control breathing, thinking or cognitive patterns, and/or heartrate control.

The request 107 may be transmitted over a network 106 and received and parsed by a sleep assistance sleep operating system 110, also shown and described herein as the sleep assistance OS 110. The network 106 may include one or more local area networks, wide area networks, virtual private networks, and/or may include the Internet. In the present embodiment, the network may include a local network (e.g., the network 106A, such as a Bluetooth® and/or WiFi network) and a wide area network (e.g., the network 106B, such as the Internet), each of which may be communicatively coupled through one or more access points. As described in conjunction with the embodiments of FIG. 1B and FIG. 1C, the sleep assistance OS 110 may be based on one or more "artificial intelligence" and/or large language models capable of providing assistance, For example, in one or more embodiments, the sleep assistance OS may be specifically adapted as shown and described herein to control, coordination and/or mediate one or more additional devices, systems, and/or AI models (including the sleep assistance model 115 and/or the generative content models 120).

Figure 7:
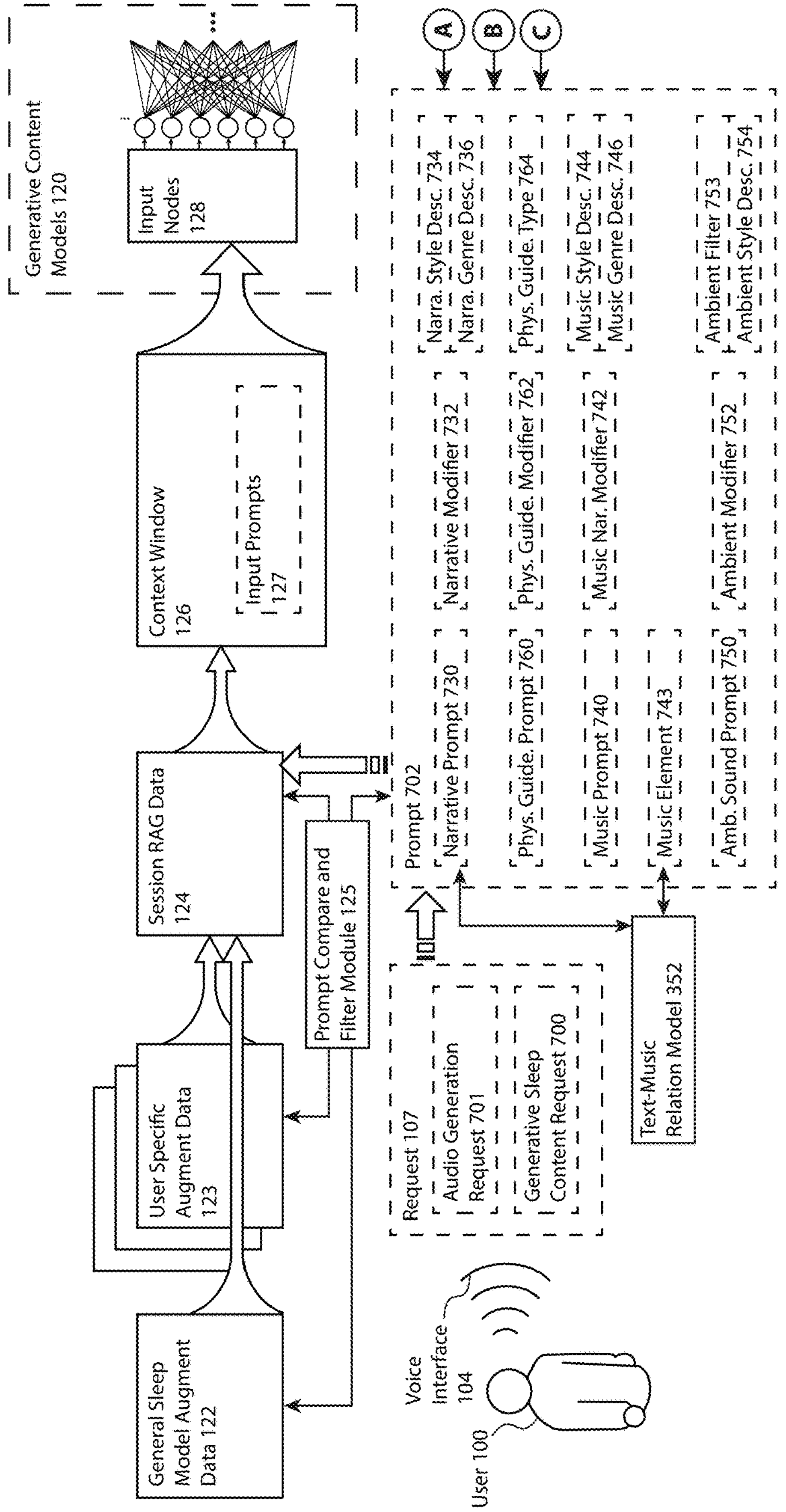
FIG. 7 illustrates an example of a generative prompt extraction and formulation process, including parsing an audio generation request into one or more prompts and elements thereof, including automated prompt structuring through comparison with one or more general and/or user specific augment data before the prompts are provided as inputs to one or more generative content models, according to one or more embodiments.

The sleep assistance server 200 may include a request agent 210 for processing requests and developing and engineering generative prompts, as further shown and described in conjunction with the embodiments of FIG. 2 and FIG. 7.

Generative prompts extracting from the request 107 may be formulated (e.g. into the prompts 702), combined with data of the user 100 from a user profile 410, engineered after contextualization with the user data, and/or then utilized for generative production of the sleep assistance audio 102 or portions thereof. In one or more embodiments, the sleep assistance server 200 may forward prompts, engineered prompts, and/or other data usable as inputs to a generative content server 300. A generative content engine 320 may select one or more appropriate generative content models 120 and utilize such data as inputs to the one or more generative models 120, for example to generate narrative, music, ambiance, and/or physiological guidance. A content integration engine 380 may integrate two or more aspects of the outputs of the generative content model 120, including possible re-submission and re-integration if needed to ensure quality. Where preexisting content 510 is utilized in conjunction with generative content, the content integration engine 380 may additionally combine the generative content with the preexisting content 510. The resulting audio from the outputs of the one or more generative content models 120 may then be returned for playback to the earphone 600 over the network 106 as part of the response 108. As a result, the user 100 may be able to initiate, enhance, and/or maintain sleep by utilizing custom generated content unique to their changing circumstances, tastes, or preferences. At the same time, potentially powerful or generalizable patterns may be derived from, and fed back into, the AI models, their training data, and/or their augmentation sources. Generation of the sleep assistance audio 102 is further shown and described in conjunction with FIG. 1B, FIG. 2, FIG. 3, FIG. 5, FIG. 7, FIG. 8, FIG. 9, FIG. 17 through FIG. 24, and throughout the present embodiments.

The effectiveness of preexisting and/or generative sleep assistance audio 102 may be evaluated both with objective data (the physiological data 205, the sleep session data 414 derived therefrom, and/or the sleep metrics data 418 developed therefrom) and/or with user 100 opinion data, such as user 100 feedback and/or explicit user 100 ratings. For example, the physiological data 205 may include respiration rate, respiration rate variability, heartrate, heartrate variability, and/or user macro movements indicative of restlessness, such as rolling over or changing sleeping position. For example, as shown and described herein, the physiological data 205 may be analyzed to determine cognitive states of the user 100, including for example an awake state, a pre-sleep state, an asleep state, a rapid eye movement (REM) sleep state, a non-rapid eye movement (NREM) state, and/or other cognitive states. Cognitive states may be determined over time periods, including a sleep session to generate time series data, e.g., a set of time periods 416 in which the user 100 was in various cognitive states over the course of a sleep session. In one or more embodiments, the sleep session may be initiated automatically (e.g., the user 100 installing the earbuds in their ears) or manually (e.g., the user 100 reporting through the voice interface 104 they are intending to fall asleep soon), and may persist until a manual termination, automatically (e.g., the user 100 taking out their earbuds), and/or by automatic detection of a concerted awake state of the user 100 (e.g., the user 100 engaging concerted macro motions, walking motions, or beginning to speak in a way not likely to be intended communication through the voice interface 104). A concerted awake state may also be confirmed or refuted by query to the user 100 via the voice interface 104.

Each sleep session may be stored in the sleep session data 414, and multiple instances of the sleep session data 414 may record data related to the long-term sleep activities and qualities of the user 100. It will be noted that the user 100 may be sleeping within a sleep environment 101. For example, the user 100 may be sleeping in a room such as a bedroom or hotel room, an outdoor area within the hearing range of the user 100, and/or any area external to the user that can generate noise the user 100 could hear while attempting to sleep. The sleep session data 414 may also include other relevant data sensed within the sleep environment 101, for example temperature, ambient sound, humidity, brightness, and/or other data which may have an effect on the sleep cycles, circadian rhythm, and/or general physical and mental comfort of the user 100. Such environmental data may be time-sequenced along with cognitive state, in one or more embodiments.

The sleep session data 414 may be used to generate sleep metrics which may be stored in the sleep metrics data 418. The sleep metrics data 418 may include, for example, a sleep onset latency value, a length of a sleep period, a ratio of the sleep to awake periods, a number of REM periods, and/or other sleep metrics shown and described herein or as may be known in the art for determining sleep quality. The sleep metrics data 418 may also include comparative metrics. For example, after sufficient collection of data for the user 100, a baseline may be established, as may be stored in the user baseline sleep metrics data 417. Other comparative metrics may be made against a larger population of users 100 and/or relevant selective sub-populations of users 100 for which data is collected. Collection, evaluation and generation of physiological data 205, sleep session data 414, and/or sleep metrics data 418 are further shown and described in conjunction with the embodiments of FIG. 2, FIG. 9, FIG. 10, FIG. 11, and FIG. 12.

In one or more embodiments, the sleep assistance audio 102 may be measured for effectiveness in inducing or maintaining sleep and/or any of the cognitive states determinable through the physiological data 205. In a straightforward example, effectiveness may be evaluated without regard to other data or factors. For example, sleep assistance audio 102 may be determined to be effective when inducing sleep within five minutes. In another of many examples, sleep assistance audio 102 may be evaluated with respect to other users 100 and/or a general baseline. For example, the sleep assistance audio 102 may be determined to be effective when the sleep assistance audio 102 indices sleep within the $60^{th}$ percentile for a sleep onset latency ranking, either against other sleep assistance audio 102 attempted by the user 100 and/or against sleep assistance audio attempted by other users 100. In yet another example, the user 100 may be queried and asked to rate the effectiveness, either subtly when falling asleep and/or upon waking. In yet another example, individual elements and/or characteristics may be assessed for effectiveness, including dichotomous testing (e.g., "A-B testing") to test effectiveness.

Upon determining effectiveness, elements and/or characteristics of the sleep assistance audio 102 may be extracted for further use and/or refinement. This may both further improve or "hone in" on the most effective elements or characteristics of sleep assistance audio 102 for the user 100 and/or a population of users 100. Extraction of elements and/or characteristics may also compile a set of generative "building blocks" with which new sleep assistance audio 102 can be created without sounding repetitive and/or without the user 100 becoming desensitized to sleep-inducing or sleep-maintaining affects. Determining the effectiveness of sleep assistance audio 102 is further shown and described throughout the present embodiments. Determining effectiveness of sleep assistance audio 102 and/or generative sleep content 800, and utilizing such effectiveness in prospective generation for the benefit of the user 100 and/or a population of users 100, is further shown and described in conjunction with the embodiments of FIG. 2, FIG. 10, FIG. 13, FIG. 14, and throughout the present embodiments.

As further shown and described below, the sleep assistance audio 102 and the elements and/or characteristics thereof may be utilized to further refine one or more generative content models 120, for example through expanding data available to the generative models 120 through retrieval augmented generation, through fine-tuning the generative content models 120, and/or through custom training and/or retraining of base models (e.g., the text generation base model 132, the music generation base model 142, etc.). In one or more embodiments, one or more of the generative content models 120 may each comprise an artificial neural network, where each artificial neural network may include a plurality nodes comprising a set of input nodes, a set of hidden nodes, and a set of output nodes.

In addition to the generation and evaluation of sleep assistance audio 102, in one or more embodiments the sleep evaluation and assistance network 199 may include the capability to report sleep data, respond to questions related to sleep health, and/or to formulate actionable sleep improvement interventions 180. Notably, this capability may include evaluation of particular data relevant to the user 100 generating the request 107. As a threshold example, information regarding sleep can be appropriately and opportunistically reported to the user 100, for example providing a voiceover of the sleep metrics data 418 for a previous nights'sleep session data 414 upon the user 100 waking through the voice interface 104. However, the user 100 may also ask questions and/or request information about either general aspects of sleep, or particular aspects that relate to them or their sleep data. Responses may include a sleep improvement intervention 180 that provides particular instructions on how to achieve better sleep, including general aspects such as selecting a restful sleep environment 101 and/or particular aspects such as improving sleep metrics such as sleep onset latency. In one or more preferred embodiments, both the query of the user 100 and additional context such as the sleep session data 414 and/or sleep metrics data 418 derived therefrom may be considered in formulating the sleep improvement intervention 180. As will be shown and described throughout the present embodiments, the sleep assistance OS 110 may receive and parse the request for sleep assistance (e.g., within the request 107), gather additional context or inputs (including for example through a user specific augment data 123), and utilize data of the request 107 and additional context for formulated inputs to a specialized AI model, e.g., the sleep assistance model 115. Generation of the sleep improvement 180 to provide assistance to the user 100 is further shown and described in conjunction with FIG. 1C, FIG. 2, FIG. 10, FIG. 15, and throughout the present embodiments.

In one or more embodiments, sleep improvement interventions 180 and elements thereof (e.g., individual steps, guidelines, or requirements) may be evaluated for effectiveness. In one or more embodiments, the user 100 may be queried to determine if the sleep improvement intervention 180 was, or is being, properly implemented. As just one straightforward example, the user 100 may be provided with a sleep improvement intervention 180 that requests that the user 100 not to look at a computing device screen within 30 minutes of lying down to sleep. The user 100 may later be asked if and/or to what extent they followed the sleep improvement intervention 180 so that effectiveness can be properly determined. In another example, the user 100 may be instructed to keep their heartrate below a threshold for a period of time prior to lying down to sleep, where sensor data may be utilized to verify compliance with the sleep improvement intervention 180 so that effectiveness can be properly evaluated. Similar to the determination of effectiveness of the sleep assistance audio 102, the determination of effectiveness of the sleep improvement intervention 180 can include an objective determination without regard to additional data, comparison to other sleep improvement interventions 180 utilized by the user 100, and/or against baselines of the user 100 and/or a population or sub-population of users 100. Determination of effectiveness of the recommendations and/or sleep improvement interventions 180 are further shown and described in FIG. 2, FIG. 10, FIG. 13 through FIG. 16, and throughout the various embodiments. It should be noted that, in one or more embodiments, the sleep improvement intervention 180 may include sleep assistance audio 102. In this case, both the sleep assistance audio 102 and utilization of the sleep assistance audio 102 may be assessed for effectiveness, as shown and described throughout the present embodiments.

As a result of several of the embodiments described above, the sleep evaluation and assistance network 199 may (i) provide an easily interfaced with, communicated with, and controlled technology platform to monitor and track sleep of a user 100, generate custom sleep assistance audio 102, evaluate effectiveness of sleep assistance audio 102 and/or continually improve the process of its generation, provide sleep health information to users 100, respond to sleep health questions, formulate sleep improvement interventions 180 including in combination with personal sleep data, evaluate the effectiveness of sleep improvement interventions 180, and/or continually improve the process of providing information and/or generating recommendations and interventions. The sleep evaluation and assistance network 199, both collectively and in its individual aspects, provides a substantial capability to improve sleep health of at least a sub-population of users 100, including both immediate effects to improve sleep and long-term effects to improve sleep health and hygiene. Each of the below embodiments will now be described in further detail.

Figure 1B:
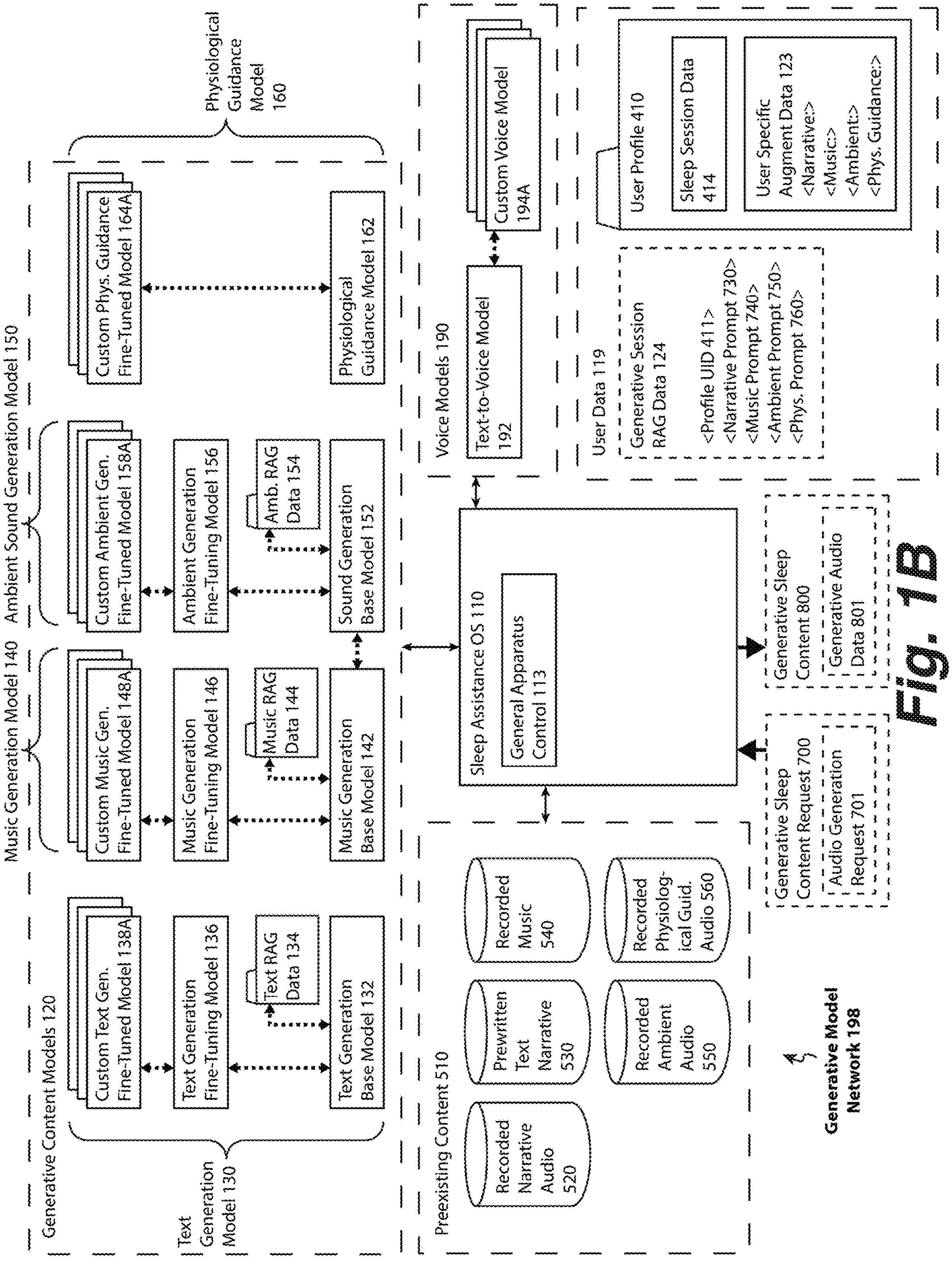
FIG. 1B illustrates a generative model network, including the sleep assistance OS for receiving generative sleep content requests and generating generative sleep content, along with mediating: preexisting content, generative content models (including narrative text generation, music generation, ambient sound generation, and physiological guidance pattern data), a cognitive state engine for determining a sleep state of the user, custom voice model(s), and user data such as that stored in association with a user profile, according to one or more embodiments.

FIG. 1B illustrates a generative model network 198, according to one or more embodiments. In one or more embodiments, the generative model network 198 may coordinate one or more generative and/or transformative models, including AI-based models. For example, the generative model network 198 may mediate and pass data, model inputs, and/or model outputs between devices, systems, and/or other AI models. In one or more embodiments, the generative model network 198 may include the sleep assistance OS 110 communicatively coupled to a set of generative content models 120, a cognitive state engine 204, a set of voice models 190, a set of user data 119, and/or a set of preexisting content 510.

According to one or more embodiments, the sleep assistance OS 110 may include a large language model or other predictive text model configured to recognize commands and generative requests of the user 100. The present embodiment of FIG. 1B focuses on generative requests, for example the generative sleep content request 702.

In one or more embodiments, the sleep assistance OS 110 receives a request 107 and/or a generative sleep content request 700. As further shown and described in conjunction with the embodiment of FIG. 2, the request 107 may have been pre-parsed to extract the generative sleep content request 800, and/or the generative sleep content request 800 may have been succinctly preformatted when generated by the user 100 (e.g., through a specific set of questions and answers processed through the voice interface 104). Alternatively, or in addition, the sleep assistance OS 110 may be configured to recognize and extract the generative sleep content request 700 or portions thereof, for example where the sleep assistance OS 110 includes a large language model with access to, or trained with, additional data specifying examples of generative requests and competent responses thereto.

In one or more embodiments, the sleep assistance OS 110 may parse and structure prompts for additional models, alone or in combination with traditional parsing systems that may recognize and group particular words within narrative text, music, ambient sound, and/or physiological guidance. Prompt parsing and structuring are further shown and described in conjunction with the embodiments of FIG. 2, FIG. 7, FIG. 17, FIG. 18, and throughout the present embodiments.

In one or more embodiments, the sleep assistance OS 110 may determine one or more generative content types to initiate, e.g., narrative text, music, ambient, and/or physiological guidance. In one or more embodiments, the sleep assistance OS 110 may determine whether each type will be generated utilizing preexisting content 510 and/or elements and qualities thereof, or generative content, and may additionally determine a priority or level. The priority level may implement a relative importance and/or order of operations, for example which content may constrain the generative and/or integration priorities of which other content. For example, where the user 100 requests "a calm story about a girl who discovers an abandoned castle and finds a great treasure set to music," it may be determined that (i) narrative text is of greater importance to the user 100 than the music because more description and modifiers exceed those of the music description; (ii) the subject matter of the story must include a girl, a castle, and a treasure; (iii) the music should include description and/or modifiers associated with the story, for example "calm". Although some large language models (e.g., GPT4) may be sufficient to generate a competent narrative responsive to narrative request, in one or more preferred embodiments a large language model included within or accessible to the sleep assistance OS 110 may be specialized to generate competent sleep-improving generative content, as will be further shown and described herein. For example, and without limitation, specialization may be implemented in whole or in part through retrieval augmented generation ("RAG") specialized for sleep content (including both generally applicable RAG and user specific RAG), fine-tuning models based on competent predictive responses, and/or custom training of AI models and/or AI base models.

Additionally, the sleep assistance OS 110 may reference the user data 119 to detect and extract for use inputs to the generative content models 120, additional information or data related to the user 100, and/or the preferences of the user 100. For example, it may have been determined that certain synthetic voices are more effective at inducing and/or maintaining sleep in the user 100, and a particular voice model (or custom voice model 194) may be stored for use by a text-to-speech model 192 for final generation of the generative sleep content 800.

In one or more embodiments, the generative content models 120 may include a text generation model 130, a music generation model 140, an ambient sound generation model 150, and/or a physiological guidance model 160, each of which may be comprised of one or more artificial neural networks. In one or more embodiments, each of the generative content models 120 may comprise an artificial neural network including a plurality nodes comprising a set of input nodes, a set of hidden nodes, and/or a set of output nodes. In one or more embodiments, a text generation model 130 may include a text generation base model 132, which may include a large language model (LLM). As just one example, the text generation base model 132 may include Llama 2, GPT-4, and/or Claude. In one or more embodiments, the text generation model 130 may include one or more text retrieval augmented generation data 134, also shown and described herein as the text RAG data 134. The text RAG data 134 may include data that may be accessed to improve context, engineer narrative prompts 730, and/or improve predictive text performance of the large language model. For example, the text RAG data 134 may include additional curated data about what narratives and/or narrative elements are, or are not, calming or conducive to sleep quality for a large population of users 100 and/or subpopulation of users 100. All or a portion of the text RAG data 134 may be accessed and/or loaded into a context window (e.g., the context window 126 of FIG. 7) to improve competence of the text generation base model 132, according to one or more embodiments. Where a portion of the text RAG data 134 is selected, the portion may be selected based on relevance of the generative sleep content request 700.

In one or more embodiments, the text generation model 130 may include a text generation fine-tuning model 136. The text generation fine-tuning model 136 may include a copy of all or a portion of the text generation base model 132 in which a plurality of decision nodes of the text generation base model 132 have had node-weights or other decision variables adjusted based on a training dataset. For example, the training dataset may include a list of generative sleep content requests 700 or narrative-relevant portions thereof, each associated with one or more competent examples written or otherwise approved by authorized and/or qualified persons (or even other trained, trusted, and/or statistically proven AI models). In one or more other embodiments, the text generation fine-tuning model 136 may include a low rank adaptation (LoRA). Use of the text generation fine-tuning model 136 may assist in improving response speed in generating an output of the text generation model 130 and/or free additional space within the context window 126 such that a greater amount of information that may change relatively quickly can be incorporated as inputs to the text generation model 130.

In one or more embodiments, the text generation model 130 may be or include a custom text generation fine-tuned model 138. For example, the custom text generation fine-tuned model 138 may be established for sub-population of users 100 and/or even for a particular user 100. The custom text generation fine-tuned model 138 may include a LoRA developed for each sub-population of users 100 and/or individual users 100. Although not shown, it should be noted that the text generation model 130 may also include a large language model trained from scratch, e.g., a custom developed and trained, rather than commercially available, artificial neural network. The training dataset for narrative text may include a large dataset of narrative stories, bedtime stories, podcast scripts, etc. In one or more embodiments, an algorithm for determining a general degree of excitement or stimulation may be used as a training data content filter, the algorithm filtering or selecting based on word choice, sentence structure, syntax, semantics, and/or other narrative analysis techniques known to those skilled in the art. The training set may further include text of effective narratives and input prompts therefore, for example as generative content effectiveness may be evaluated for effectiveness as shown and described herein. The music generation model 140 may output either audio data and/or a description of musical data or elements thereof (e.g., a MIDI file) that may be rendered.

In one or more embodiments, the music generation model 140 may include a music generation base model 142. The music generation base model 142 may be or include a commercially available music generation model, for example AudioCraft, AIVA, Ecrett, Mubert, Musicfy.lol, Soundraw, and/or other commercially available or open source music generation models. The music generation model 140 may be able to receive as an input a music prompt 141, which may include a text prompt, a composition (including a melody), and/or other human or machine-readable musical descriptions (e.g., tablature, soundwave descriptions, MIDI files, etc.).

In one or more embodiments, the music generation model 140 may include a music generation retrieval augmented generation data 144, also referred to the music RAG data 144. The music RAG data 144 may include additional information usable to expand context for the music generation base model 142, for example melodies that match certain narrative genres or styles, musical elements or instruments generally preferred and/or favored, etc. As one example, wind instruments or bass stringed instruments may be preferred for relaxation and sleep versus percussion instruments, whereas vocals may depend on tonal range and lyric discernability which could otherwise keep the cognition of the user 100 engaged. The music RAG data 144 may include any data that may be utilized as a responsive input to the prompt of the music generation base model 142, for example both audio descriptions of music, audio descriptions of musical elements, and/or text-based narrative descriptions of music or elements thereof.

The music generation model 140 may include a music generation fine-tuning model 146. For example, the music generation base model 142 or portion thereof may be further trained such that node weights of the artificial neural network or other decision elements are adjusted to more closely adhere to training examples and/or criteria. In one or more embodiments, the training dataset may include prompts associated with competent audio or music composition data. In one or more embodiments, the music generation fine-tuning model 146 may include a LoRA. In one or more other embodiments, the music generation model 140 may be or include a custom music generation fine-tuned model 148, for example as may be trained on training data including music or music preferences of a subpopulation of one or more users 100. For example, music and the elements thereof may be a partially cultural interpretation in which certain sounds, instruments, or music may be effective for some (e.g., effective at inducing or maintaining a state of restfulness and/or sleep), while being off-putting or undesired able for others. Modifying the music generation model 140 to accommodate differing cultural interpretations may be effected through the music RAG data 144. Alternatively, or in addition, increased query efficiency and long-term computational resource efficiency may be achieved through training and use of the custom music generation fine-tuned model 148.

In one or more embodiments, the generative content models 120 may include an ambient sound generation model 150. An ambient sound within the sleep assistance audio 102 may include a sound effect, a background sound, and/or a setting sound. For example, in one or more embodiments the ambient sound may include a nature sound (e.g., an insect, a bird singing), a natural environmental sound (e.g., the sound of wind through tree, water running in a stream, dripping water in a cave, crashing waves at a beach), and/or sound effects of man-made environments (e.g., background engine noise, the sounds of several people talking in the background such as in a busy café, the sounds of a cityscape, etc.). The ambient sound generation model 150 may accept as inputs any of a text prompt, an audio wave, a digital description of an ambient sound or elements thereof, etc. The ambient sound generation model 150 may generate as outputs a description of the ambient sound (e.g., description of individual sounds and their composition and/or arrangement). As further shown and described below, physiological guidance may be "encoded" in the ambient sound such that a user 100 may use the ambient sound as conscious or unconscious queues, for example to assist in breathing or to help management of their heartrate, according to one or more embodiments.

In one or more embodiments, the ambient sound generation model 150 may include a ambient sound generation base model 152, for example a commercially available artificial neural network (e.g., ElevenLabs, LOVO AI, etc.).

It should be noted that, in one or more embodiments, the same or a similar specialized model may be utilized to generate both ambient sound and music. In this case, the music generation model 140 may be implemented as a fine-tuned version of the ambient sound generation base model 152.

In one or more embodiments, the ambient sound generation model 150 may include an ambient retrieval augmented generation data 154, also referred to the ambient RAG data 154. The ambient RAG data 154 may include additional information usable to expand context for the ambient sound generation base model 152, for example ambient sound audio or text descriptions thereof that match certain narrative genres or styles that may be generally preferred and/or favored for inducing or maintaining a restful state and/or sleep. The ambient RAG data 154 may include any data that may be utilized as a responsive input to the prompt of the ambient sound generation model 150, for example both audio descriptions of ambient sounds, audio descriptions of ambient sound elements, and/or text-based narrative descriptions of ambient sounds or elements thereof.

The ambient sound generation model 150 may include an ambient generation fine-tuned model 156. For instance, the ambient sound generation base model 152 or portion thereof may be further trained such that node weights of an artificial neural network of the ambient sound generation model 150 or other decision elements may be adjusted to adhere to training examples and/or other criteria. In one or more embodiments, the training dataset may include prompts associated with one or more designations of competent ambient audio data. Similar to the music generation fine-tuning model 146, the ambient generation fine-tuned model 156 may include a LoRA. In one or more other embodiments, the ambient sound generation model 150 may be or include a custom ambient generation fine-tuned model 158, for example as may be trained on training data including ambient sound preferences of a subpopulation of users 100, or even individual users 100. Modifying the ambient sound generation model 150 may be effected through the music RAG data 144, or, for increased query efficiency and long-term computational resource efficiency, development of the custom ambient generation fine-tuned model 158.

In one or more embodiments, it will be appreciated that the ambient sound generation model 150 may primarily arrange or mix a catalogue of preexisting sounds. For example, there may be a library of audio files, audio elements, and/or descriptions of ambient sound that can be composed or arranged into a soundscape. The artificial neural network of the sound generation model 105 may receive as an input a text prompt, select and arranges the sound responsive to the text prompt, and output a description of the arrangement or composition of the audio files, audio elements, and/or descriptions of ambient sound. For example, the output may include the ambient composition data 852 which can be rendered into audio.

In one or more embodiments, the generative content models 120 may include a physiological guidance model 160. The physiological guidance model 160 may include an artificial neural network that may be configured to generate a competent template for physiological guidance cues to aid the user 100 in respiration, to control heartrate, and/or other control over other physiological aspects of the human body. The output of the physiological guidance model 160 may include a description of physiological guidance events arranged over a time period. The physiological guidance events may be rendered to produce sound that may be combined and/or overlaid with narrative text, music, and/or ambient sound. Alternatively or in addition, and as further shown and described below, a description of the physiological guidance events and timing thereof may be provided as a suggestion or constraint to one or more other of the generative content models 120, e.g., as an additional input or context influencing the output.

Many physiological guidance patterns may have been determined by sleep specialists, as known in the art. As an example, a common breathing technique for inducing relaxation and sleep may include inhaling for 4 seconds, holding a breath for 7 seconds, and exhaling slowly for 8 seconds. The long exhale may be able to activate the parasympathetic nervous system, which can signal the brain to relax, lower heart rate and blood pressure, and/or increase melatonin production. However, it may be difficult for a user 100 to maintain this count accurately. It also will be recognized that such timings are likely only to be approximate and may vary based on user 100. In one or more embodiments, an advantage of the physiological guidance model 160 may include determining the exact timing (e.g., breaching in for 4.3 seconds), varying the periods over time (e.g., starting with holding breath for 5 seconds, and over the course of two minutes transitioning to a full 7 seconds), and/or otherwise altering the physiological guidance template based on the sleep session data 414 and/or user profile data 412 such as height and/or weight. Due to measured effectiveness, as further described below, the physiological guidance model 160 may be able to refine existing known physiological guidance techniques.

In one or more embodiments, the physiological guidance model 160 may include a custom physiological guidance fine-tuned model 164. For example, the physiological guidance base model 162 or portion thereof may be further trained such that node weights of an artificial neural network of the physiological guidance base model 162 or other decision elements thereof may be adjusted to adhere to training examples and/or other criteria. In one or more embodiments, the training dataset may include prompts associated with competent physiological guidance patterns or cues, including as may have been tested and received effectiveness evaluation as shown and described herein.

Figure 8:
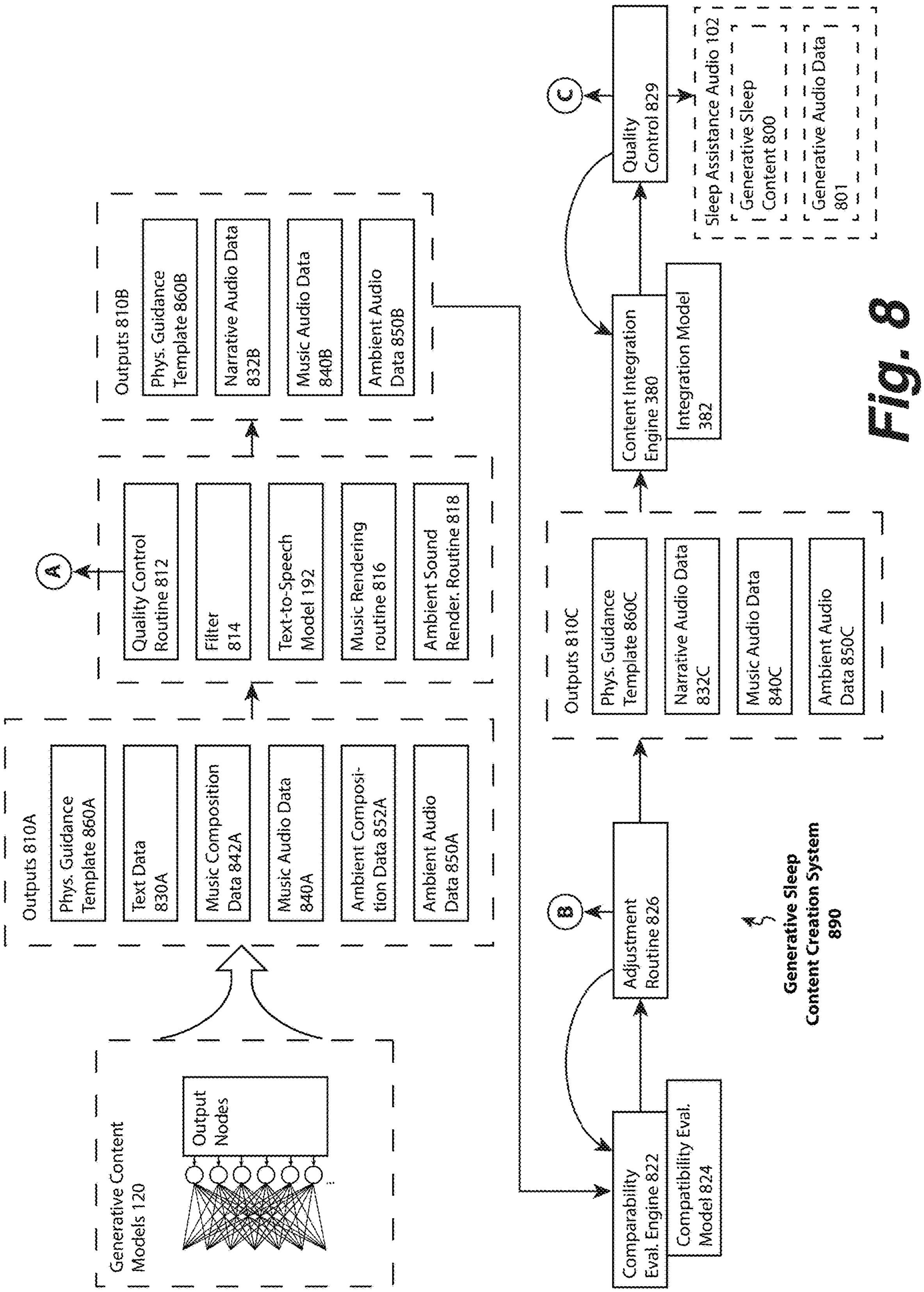
FIG. 8 illustrates a generative sleep content creation system, including non-audio, narrative, music, sound, and voice rendering, generative output adjustment, and/or AI model output integration, according to one or more embodiments.

In one or more embodiments, and as further shown and described in conjunction with the embodiment of FIG. 8, the inputs and outputs of two or more of the generative content models 120 may be coordinated, including selective serialization and integration such that the resulting output is effective at inducing and/or maintaining sleep. For example, it will be recognized that coherent synthesis of narrative, music, ambient sound, and/or physiological guidance may increase cognitive "acceptance" of the audio by the user 100, and therefore possibly relaxation. As a first example, the narrative text (e.g., the text data 830) may be generated before ambient sound is generated, where the ambient sound is associated with each portion of the story to match a setting or environment of the story. For example, in a part of a narrative story where a protagonist of the story is outside, the ambient sound may include nature sounds. In another example, physiological guidance may be the first to guide or constrain the output of additional generative content models 120 (e.g., the highest priority), whether the physiological guidance originates from a preexisting physiological guidance template and/or analysis of a recorded physiological guidance audio 560. For instance, a constraint may include generating narrative text with punctuation (a comma, period, or other pause) occurring at each transition between breathing in, holding breath, or breathing out. Similarly, music and/or ambient sound occurrence may occur according to physiological guidance events specified in the template. Additional examples are provided throughout the present embodiments.

In one or more embodiments, the sleep assistance OS 110 may also be communicatively coupled with the voice models 190, including a text-to-speech model 192 for converting and/or rendering text into audio, and/or one or more custom voice models 194. The custom voice models 194 may include data from a specific real voice and/or samples recorded therefrom, and/or a custom synthetic voice or personality. For example, the custom voice model 194 may have been generated from a sample submitted by the user 100 or licensed from a voice actor or celebrity (e.g., a famous nature film narrator). Software comprising a voice synthesizer may utilize the custom voice model 194 for generation of audio from text. In one or more embodiments, and as further shown and described in conjunction with the embodiment of FIG. 8, any other generative content models 120 that do not output audio data may be rendered by analogous description-to-sound models and/or algorithms.

In one or more embodiments, the sleep assistance OS 110 may be communicatively coupled with user data 119, including a user profile 410 including a sleep session data 414 and a user specific augment data 123 which may be accessed and used in conjunction with generative content creation. Although not shown, any of the custom models may be specified through database pointers and/or stored directly in association with the user profile 410 (e.g., the custom text generation fine-tuned model 138, the custom music generation fine-tuned model 148, the custom ambient generation fine-tuned model 158, and/or the custom physiological guidance fine-tuned model 164). The user data 119 may also include a user specific augment data 123 specifying successful prompts (or portions or keywords thereof) related to generation of narrative, music, ambient, physiological guidance, and/or rendering thereof, and as each may have been identified to be effective under varying conditions for the user 100.

The user data 119 may additionally include a session RAG data 124 for a generative content session in which parsed 702 prompts may be gathered and additional context stored before passing to a context window 126 to be provided to input nodes 128 of one or more generative content models 120. For example, the session RAG data 124 initiated for a generative content session (e.g., responsive to a generative sleep content request 700) may include each of the prompts shown and described in conjunction with the embodiment of FIG. 7, and any context data associated with each as may be extracted from the text RAG data 134, the music RAG data 144, the ambient RAG data 154, and/or as each may be mediated against and/or overwritten by user specific data in the user specific augment data 123. Although shown in logical association with the user data 119, the session RAG data 124 may be stored on the sleep assistance server 200 or in another location.

Upon any quality control, rendering, and/or integration, for example as shown and described in conjunction with the embodiment of FIG. 8, the sleep assistance OS 110 may return the generative sleep content 800 to the user 100 over the network 106, for example to be played on the earphone 600 to assist the user 100 in achieving and/or maintaining sleep.

Figure 1C:
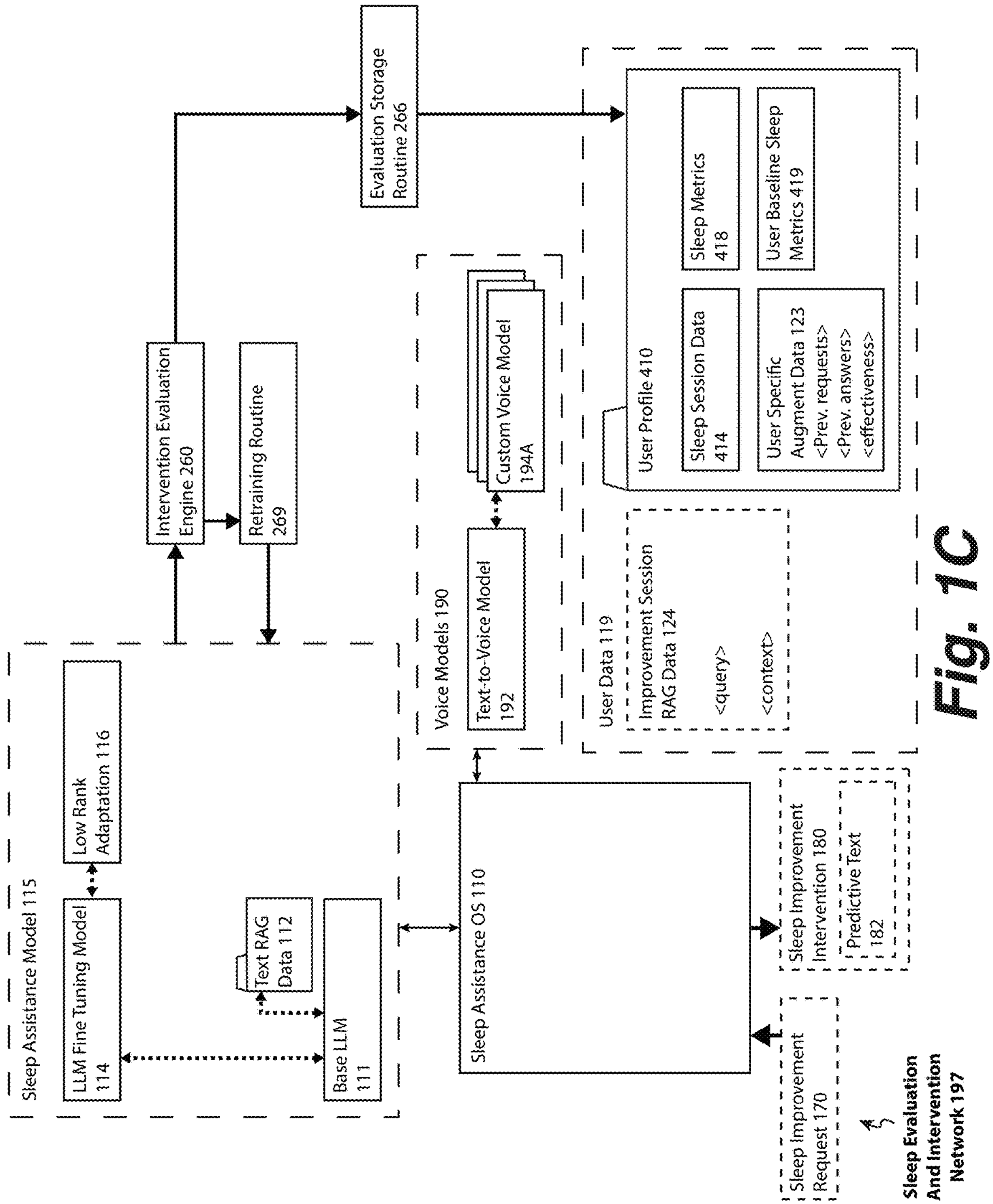
FIG. 1C illustrates a sleep evaluation and intervention network, including the sleep assistance OS for receiving sleep improvement requests and generating sleep improvement interventions, along with mediating: a sleep assistance model, an intervention evaluation engine for determining effectiveness of implemented interventions, the custom voice model(s), and/or the user data, according to one or more embodiments.

FIG. 1C illustrates a sleep evaluation and intervention network 197, according to one or more embodiments. In one or more embodiments and the embodiment of FIG. 1C, the sleep assistance OS 110 may receive a request 107 initiated by a user 100, for example through the voice interface 104. The request 107 may include a request for general information about sleep or sleep health and/or a specific question about sleep or sleep health. However, in one or more embodiments, the request 107 may include a sleep improvement request 170 initiated by the user 100. For example, the user 100 may request that they receive assistance in falling or maintaining sleep based on having difficulty sleeping over the past several days. Alternatively, or in addition, the request 107 may be automatically generated following sleep pattern analysis (e.g., based on the physiological data 205 and/or the sleep metrics data 418). In one or more other embodiments, a sleep improvement request 170 may be automatically initiated based on the general inquiry of the user 100, e.g., as an inference of an issue experienced by the user 100 and with which the user 100 may appreciate proactive assistance. The request 107 may be initially parsed to recognize and/or remove general requests without regard to user specific information from requests implicating the data of the user 100, especially assistance in achieving or maintaining sleep as may be formulated into a sleep improvement intervention 180 for the user 100.

Where the request 107 includes a general request for information, the sleep assistance OS 110 may further parse the request 107 to develop a prompt which may be input into the sleep assistance model 115. The sleep assistance model 115 may include a large language model configured to generate predictive text answering queries of the user 100. For example, the sleep assistance model 115 may include a base large language model 111 (also shown and described herein as the base LLM 111), for example GPT (e.g., GPT4) or Llama (e.g., Llama 2). In one or more embodiments, the sleep assistance model 115 may include the text RAG data 134 storing additional sleep-related information, research, and up-to-date information that may have developed following training of the base LLM 111. In one or more other embodiments, the base LLM 111 may be further fine-tuned as the LLM fine-tuning model 114 and/or may be used in conjunction with a low rank adaptation 116, also referred to herein as the LoRA 116.

In one or more embodiments, the user 100 may request sleep assistance, advice, and/or an actionable sleep intervention. In response, the sleep assistance OS 110 may formulate a sleep improvement intervention 180, which may also be referred to as a sleep improvement intervention 180, as predictive text of the sleep assistance model 115. In one or more embodiments, the user 100 may be asked a series of questions to help determine an effective possible sleep protocol, including current or previous strategies that user 100 has attempted or employed, what the user 100 finds generally effective, the preferences of the user 100, any relevant known medical conditions (e.g., insomnia), etc.

In one or more embodiments, the parsed prompt requesting sleep assistance may be input into the sleep assistance model 115. Additional information within the improvement session RAG file 174 which may be provided to the context window 126 may include data from the text RAG data 134 and/or data from the user profile 410, especially any relevant data from the current or former sleep session data 414, sleep metrics data 418, user baseline sleep metrics data 417, and/or the user specific augment data 123 (optionally including any previous effective interventions and/or any preferences of the user 100).

In one or more embodiments, a sleep improvement intervention 180 may be derived based on evaluating the sleep metrics data 418, reviewing physiological data 205, and/or asking one or more questions of the user 100. For example, it may be determined that from one or more data sources that the user 100 may not be going to sleep earlier enough, may be varying their sleep pattern too greatly, may be receiving too many environmental disturbances (e.g., noise, a snoring partner), may be eating too late, may be receiving too much visual stimulation or bright light entering the retina prior to attempting to sleep, etc. As an example, the sleep improvement intervention 180 may include: recommending that the user go to sleep at a specific time (based on their alarm/wake up) to get sufficient sleep, and maintain a regular sleep schedule.

An output of the sleep assistance model 115 may be gathered as the predictive text 182, converted to audio (e.g., through use of the voice models 190, for example as described above) and transmitted back to a device (such as the device 650) the user 100 over the network 106. The audio may be stored and transmitted as the sleep improvement intervention 180, for example provided to the user 100 on the speaker 606 of the earphones 600 (e.g., via the voice interface 104). In one or more other embodiments, the sleep improvement intervention 180 may be delivered through other means, for example text message or email. Delivery of the sleep improvement intervention 180 may be scheduled or timed to occur when it is most likely to be understood and implemented, for example just as a user 100 is preparing for sleep and/or when a sleep session has just been initiated.

Following delivery of the sleep improvement intervention 180, effectiveness may be tracked both by monitoring implementation of the sleep improvement intervention 180 and assessing its impact and/or correlation with improved sleep. In one or more embodiments, the user 100 may be instructed on the sleep improvement intervention 180, and then queried as to whether it was properly implemented. For example, the user 100 may have requested help sleeping, and a first attempt may involve reducing access to display screens, phones, and/or social media within 45 minutes of an intended sleep time. The user 100 may be queried about halfway through a sleep countdown period to determine if the user 100 adhered to a prescriptive intervention, and of not, then to what extent the user 100 adhered. The user 100 may also be queried as to a perceived effectiveness both during a prescribed sleep improvement intervention 180 and/or after. It will be recognized that gathering opinions or feedback from the user 100 may be less important than potentially disrupting sleep. In one or more embodiments, therefore, a cognitive state of the user 100 may be monitored and communication withheld until the user 100 is in a concerned awake state, for example the next morning.

In one or more embodiments, physiological data 205, sleep session data 414, and/or sleep metrics data 418 may be utilized to determine effectiveness of the sleep intervention. In one or more embodiments, the evaluation may be made by an intervention evaluation engine 260, as further shown and described in conjunction with the embodiment of FIG. 2. For example, monitoring of physiological data 205 in the pre-sleep state may determine that the user 100 was able to maintain a more stable respiration pattern, and the sleep session data 414 may determine that the user 100 improved sleep onset latency and/or REM sleep periods. The same sleep improvement intervention 180 may be recommended and/or attempted multiple times to improve statistical correlation. To assist in identifying false positives or extraneous factors, the user 100 also may be asked additional factors, such as their emotional state, whether they are in an unfamiliar location (e.g., a hotel), etc. Many other data analysis techniques for identifying causation and/or correlation will be apparent to one skilled in the art of data analysis, and polling, including use of the sleep session data 414, the sleep metrics data 418, and/or direct queries to the user 100.

Sleep improvement interventions 180 determined to be effective may be used to further improve future queries of the user 100, for example by storing the sleep improvement intervention 180 and data thereof within or in association with the user profile 410 (e.g., in the user specific augment data 123). For example, an evaluation storage subroutine 266 may be utilized to store the data in association with the user profile 410, as may be further shown and described in conjunction with the embodiment of FIG. 2. Alternatively, or in addition, effective interventions may be utilized to augment, train, re-train, and/or fine-tune the sleep assistance model 115. As an example, where a certain physiological guidance protocol resulted in a substantial decrease in a sleep onset latency period, especially among users 100 reporting or inferring sleep-impairing anxiety, the physiological guidance protocol may be added to a training dataset that includes a set of competent responses to anxious thoughts or emotions. A retaining routine 269 may be utilized to retrain the sleep assistance model 115, as further may be shown and described in conjunction with the embodiment of FIG. 2. It will be recognized that the sleep improvement intervention 180 may include recommending sleep assistance audio 102 such as generative sleep content 800, including possible use of physiological guidance to implement other breathing exercises that may be otherwise included within a sleep improvement intervention. In this way, use of the generative content may directly help implement and support sleep improvement interventions 800, according to one or more embodiments.

FIG. 2 illustrates a sleep assistance server 200, according to one or more embodiments. In one or more embodiments, the sleep assistance server 200 may include the sleep assistance OS 110, a cognitive state engine 204, a request agent 210, a sleep session engine 220, a sleep improvement intervention 180 engine 230, a sleep assistance engine 240, a content evaluation engine 250, and/or an element evaluation database 251, in addition to other elements shown in FIG. 2 and further described below. The sleep assistance server 200 may include a processor 201 that may include one or more computer processors and/or central processing units (CPUs), and a memory 203 which may include a physical non-transient computer readable memory. The sleep assistance server 200 may be communicatively coupled to the network 106.

In one or more embodiments, the sleep assistance server 200 may include the sleep assistance OS 110 or portion thereof. For example, the sleep assistance OS 110 may include one or more large language models accepting text prompt inputs, which may be located within or remote to the sleep assistance server 200 (e.g., available through remote procedure call and/or API call). Although shown as discrete elements in FIG. 2, each of the engines, systems, routines, subroutines, agents, databases, data, and files may be communicatively coupled to one another, through the network, the memory 203, and/or other communication networks or buses. In one or more embodiments, it will be recognized sleep assistance OS 110 may be communicatively coupled to each of the other agents, engines, routines, and/or other elements shown and described in the embodiment of FIG. 2 and the other figures, including through remote procedure call.

In one or more embodiments, the sleep assistance server 200 may include a cognitive state engine 204 which may be configured to determine a cognitive state of the user 100 from sensor data. The cognitive state may include an awake state, a pre-sleep state (a "drowsy state"), a sleep state, and/or gradations within a sleep state, such as a REM state, a deep sleep state, an NREM state, and/or a shallow sleep state. The cognitive state may be specified and stored as cognitive state data identified by an identifier, such as the cognitive state ID 415, as shown and described in conjunction with FIG. 4. The cognitive state may be determined utilizing physiological information about the user, for example physiological data 205 generated from sensors (e.g., the physiological sensors 612 of FIG. 6) on one or more devices worn by the user 100 and/or within the sleep environment 101 of the user 100. For example, in one or more embodiments the physiological data 205 may include motion data from an inertial measurement unit (IMU) and/or accelerometer of an earbud (e.g., an earbud instance of the earphones 600), from a microphone (e.g., the microphone 608), and/or coordination of the signals from each to determine physiological events of significance. The physiological data 205 may include temperature, sound generated by the body of the user 100, and/or motion data (both macro motions, such as the user 100 rolling over or walking, and micro movements, such as a motion from a heartbeat or lungs expanding from breathing).

In one or more embodiments, the physiological data 205 may be transmitted from one or more devices, such as the earphones 600, and/or the device 650, over the network 106 to the cognitive state engine 204. As may be known in the art, individual physiological events such as heartbeats and respiration events may be determined from the physiological data 205.

In one or more embodiments, the cognitive state engine 204 may include a state monitoring routine 206 configured to monitored cognitive state of the user 100. In one or more embodiments, the state monitoring routine 206 may include computer readable instructions that when executed monitor a cognitive state of the user 100 for a time period. For example, the state monitoring routine 206 may monitor the sleep state of the user 100 over the course of a sleep session, e.g., from a time period from when the sleep session begins until a time period where the sleep session is determined to have ended, for example as further shown and described below. State monitoring may be initiated in association with initiating of a sleep session. The sleep state may be monitored continuously and/or periodically and from analysis of the physiological features determined from the physiological data 205, and as may be logged in the sleep session data 414. For example, cognitive state may be determined every 10 seconds, 30 seconds, or 60 seconds based on analysis of physiological features.

The cognitive state engine 204 may include a state determination routine 208 configured to determine cognitive state of the user 100. In one or more embodiments, the state determination routine 208 may include computer readable instructions that when executed determine the user 100 is in a sleep state based on the physiological data 205. As known in the art, cognitive state such as the sleep state may be determined from analysis of heart rate, heart rate variability, a heartrate curve, respiration rate, a respiration rate curve, respiration rate variability, and/or the type and extent of macro movements of the user 100. In one or more embodiments, the state determination routine 208 may include computer readable instructions that when executed determine the user 100 is in the concerned awake state based on the physiological data 205. For example, following a period of determined sleep state, a relatively abrupt change in heartrate, respiration rate, respiration rate variability, and/or macro motion (e.g., especially certain motions, such as sitting up or walking, as determinable by an IMU), and/or other indicators such as the user 100 speaking or using the voice interface 104, may be used to determine a concerted awake state.

The cognitive state of the user 100 may be stored in a time-sequenced data file, for example logging the cognitive state as may be stored in the sleep session data 414 and identified through a cognitive state ID 415, at each reference point and/or measurement point along a timeline. The time-sequenced data may be stored within the sleep session data 414, for example with designated periods for an initial awake state, sleep state, and termination of the sleep state, which may include sub-periods for REM sleep, deep sleep, NREM sleep, and/or shallow sleep (e.g., the time periods 416, each of which may also be tracked or labeled through a unique and/or sequential identifier).

The request agent 210 may be configured receive and parse the request 107, including routing and/or allocating sub-requests to the sleep assistance OS 110, other portions of the sleep assistance server 200, and/or other portions of the generative content server 300, according to one or more embodiments. The request 107 which may include the audio generation request 701 may be generated through a voice interface 104 collected on a microphone (e.g., the microphone 608) of an earbud (e.g., an instance of the earphones 600). The request 107 may include multiple aspects or sub-requests, including for example (i) a request to control a device aiding in sleep, such as the earphones 600 (e.g., a hardware command such as a change in volume, a change in noise canceling, a power-off command, etc.); (ii) a generative sleep content request 700, (iii) a sleep improvement request 170; (vi) a request for sleep data personal to the user 100 (e.g., physiological information, sleep session data 414, sleep metrics data 418, etc.); (v) a request for general information (e.g., time of day or night, weather), and/or (vi) a general request for sleep information. In one or more embodiments, the request agent 210 may include a content request parser 212 which may be configured to parse the request 107, including recognition and delineation of any of the above categories, e.g., separation of any generative sleep content request 700 from any sleep improvement request 170. In one or more embodiments, the content request parser 212 may include computer readable instructions that when executed receive a request 107 from the user 100 including an audio generation request 701 for generation of sleep assistance audio 102. The audio generation request 701 may include a generative sleep content request 700, for example as further shown and described in conjunction with FIG. 1B. In one or more embodiments, the content request parser 212 may be configured to recognize and/or delineate a request for preexisting audio versus one having at least one component of generative audio. In one or more embodiments, the content request parser 212 includes computer readable instructions that when executed generates a prompt from the user for selection of the sleep assistance audio 102 (e.g., from the preexisting content 510) and/or generation of the sleep assistance audio 102 (e.g., from generative content and/or combinations of generative content with preexisting content 510).

Any generative sleep content requests 700 and portions thereof may be passed to the content prompt extraction routine 214 which may be configured to further parse the type of generative request and components thereof. The content prompt extraction routine 214 may be configured to extract a generative narrative request and data thereof from the request 107. In one or more embodiments, the content prompt extraction routine 214 may include computer readable instructions that when executed parse the audio generation request 701 to extract a narrative prompt 730. For example, the narrative prompt 730 may be identified through portions of transcribed text from the voice of the user 100 which relate to narrative, story, and/or verbalized content and common words or descriptors thereof. In addition, narrative prompts 730 may also be extracted and applied from other portions, as described below (e.g., a request for "calm" music may be extracted and applied for use as a prompt in generating a "calm" story).

In one or more embodiments, the content prompt extraction routine 214 may include computer readable instructions that store the narrative prompt 730 in a computer readable memory (e.g., the memory 203). For example, the narrative prompt 730 may be stored in session RAG data 124 initialed for a generative content session and/or within the context window 126. In one or more embodiments, the content prompt extraction routine 214 may include computer readable instructions that when executed determine a narrative modifier 732 from the audio generation request 701 comprising at least one of a narrative style description 734 and a narrative genre description 736. For example, the narrative style specified in the narrative style description 734 may include the writing style of a famous author (e.g., Ernest Hemingway, with short and succinct sentences), expository writing, descriptive writing, and/or qualities such as baroque, positive, melancholy, etc. The narrative genre description 736 may include descriptions such as fiction, non-fiction, speculative fiction, science fiction, fantasy, travel, adventure, romance, horror, etc.

The content prompt extraction routine 214 may be configured to extract a physiological guidance request and data thereof from the request 107. In one or more embodiments, the content prompt extraction routine 214 may include computer readable instructions that when executed parse the audio generation request 701 to extract a physiological guidance prompt 760. The physiological guidance prompt 760 for example may include a description of a breathing exercise, a heartrate control exercise, a muscular and/or motion control exercise for relaxation, etc. In another example, the physiological guidance type may include at least one of guiding a respiration rate and/or controlling a respiration pattern. In one or more embodiments, the content prompt extraction routine 214 may include computer readable instructions that when executed store the physiological guidance prompt 760 in the computer readable memory (e.g., the memory 203). In one or more embodiments, the content prompt extraction routine 214 may include computer readable instructions that when executed determine a physiological guidance modifier 762 from the audio generation request 701 comprising a physiological guidance type 764. The physiological guidance modifier 762 may include qualities and/or characteristics of the physiological guidance, for example tapering off, transitioning, etc.

The content prompt extraction routine 214 may be configured to extract a music generation request and data thereof from the request 107. In one or more embodiments, the content prompt extraction routine 214 may include computer readable instructions that when executed parse the audio generation request 701 to further determine if a music prompt is included within the audio generation request 701, including for example a music modifier 742 such as the music style description 744 (calm, allegro, complex, simple, major, minor, orchestral, synthesized, etc.) and/or the music genre description 746 (e.g., classical, jazz, bluegrass, country, popular, etc.). It should be noted that the music prompt 740 may include negative prompts (e.g., requested for exclusion and/or deemphasis), which may also be referred to as a music filter 743 within the context of AI model prompting. For example, the music filter may be optionally extracting form the music prompt 740, e.g., exclusion of percussion, inclusion of only stringed instruments, inclusion of piano and only one other instrument, etc. In one or more embodiments, the content prompt extraction routine 214 may include computer readable instructions that when executed store in the computer readable memory the music prompt 740 and optionally at least one of the music style description 744, the music genre description 746, and/or the music filter 743.

In one or more embodiments, the content prompt extraction routine 214 also may be configured to extract an ambient sound request and data thereof from the request 107. In one or more embodiments, the content prompt extraction routine 214 may include computer readable instructions that when executed parse the audio generation request 701 to further determine an ambient sound prompt 750 and may store the ambient sound prompt 750 in the computer readable memory (e.g., the memory 203). The content prompt extraction routine 214 may include computer readable instructions that when executed parse the request 107 to determine a requested element of the sleep assistance audio 102. The requested element may include, for example, an instrument (e.g., a bass), a type of sound (e.g., wind, a type of bird call), a note, a tonal frequency, and/or other sound elements.

In one or more embodiments, the request 210 may include an assistance parser 216 which may include computer readable instructions that when executed receive a user request 107 including a sleep improvement request 170 received through the voice interface 104 of an earbud (e.g., an instance of the earphones 600) worn by the user 100. The sleep improvement request 170 and prompt elements related thereto may be forwarded to the sleep improvement intervention 180 engine 230, as further shown and described below.

In one or more embodiments, the request agent and/or the parsing of the request 107 may be affected by an artificial neural network trained with training data comprising example requests from users 100 (e.g., similar to or typical of the requests 107) and delineated prompts 702 therefore, including possible competent reframing, restatement, and/or re-engineering of prompts 702 into the input prompts 127. In one or more embodiments, the request agent 210 may be included within and/or may be accessible to the sleep assistance OS 110 as an internal or external AI model, respectively. In one or more other embodiments, the request agent 210 may be implemented with a parsing tree classifying and separating (or duplicating, where appropriate, such as adjectives or genres meant to apply to multiple aspects of the request) information within the request 107, for example first into at least any generative sleep content request 700 and any sleep improvement request 170, and then possibly into further sub-categories. For example, the parse tree classification may separate portions of the generative sleep content request 700 into prompts related to physiological guidance, narrative, music, ambient sound, and/or other qualities. Other processes and techniques for parsing the request 107 will be apparent to one skilled in the art.

In one or more embodiments, the sleep assistance server 200 may include a sleep session engine 220 configured to setup, monitor, record, and/or manage sleep session data 414 for the user 100. In one or more embodiments, the sleep session engine 220 may include computer readable instructions that when executed initiate a sleep session data 414. The sleep session data 414 may be associated with a user profile 410, for example stored within the user profile 410, on the sleep assistance server 200 during monitoring, and/or may be stored locally to the earphones 600 or another device 650 to which the earphones 600 is communicatively coupled, such as a smartphone. In one or more embodiments, sleep session may be initiated by the user 100, for example explicitly (e.g., the user 100 using the voice interface 104 to enter a voice command to begin the sleep session) or implicitly. For instance, an implicit initiation may include the user 100 placing the earphones 600 on and/or in their ears, as may be sensed by sensors of the earphones 600. In another example, an implicit determination may include the user 100 placing the earphones 600 on their ears between 8 PM and Midnight, and/or then laying down as may be determined by an IMU). Once initiated, monitoring of the user 100 may begin, including cognitive state determination as shown and described in conjunction with the cognitive state engine 204, above, and throughout the present embodiments.

Contemporaneous with, or upon completion of, a sleep session (e.g., and/or possible finalization of a sleep session data 414), a number of sleep metrics may be calculated and optionally stored in the sleep session data 418. In one or more embodiments, the sleep session engine 220 may include a sleep metric routine 222, which may include computer readable instructions that when executed calculates one or more sleep metrics stored within the sleep metrics data 418, for example from the sleep session data 414 and/or additional data available to the sleep session engine 220. The sleep metrics may include a sleep onset latency value, a length of a sleep period during the time period, a ratio of sleep periods to an awake period during the time period, a number of REM periods, a length of REM periods, a number of Non-REM periods, a length of Non-REM periods, a number of interstitial awake periods, and/or a length of the awake period during the time period. In one or more embodiments, sleep metrics within the sleep metrics tracked and stored within the sleep metrics data 418 may also include sleep efficiency (e.g., time asleep as a proportion of time “in bed”, percentage of sleep as a proportion of a sleep target or goal, an average breathing rate for resting respiration, and/or an average resting heartrate. Still other sleep metrics may include: the total number of sleep cycles, a measure of gross motor movements during sleep and/or a period while the user is falling asleep, a measure of fine motor movement during sleep and/or the period while the user is falling asleep (e.g., indicating restlessness).

In one or more embodiments, the sleep session engine 220 may include a metric reporting subroutine 223, which may include computer readable instructions that when executed report the one or more sleep metrics to the user 100, for example by delivering audio (e.g., the session summary audio 228) to be played through the voice interface 104 using a speaker 606 of the earphone 600 (e.g., an earbud) to assist the user 100 in evaluating their sleep effectiveness. The session summary audio 228 may be delivered upon a determination the user 100 is in the concerned awake state. The session summary audio 228 may be generated through the voice-to-text system from a narrated text (e.g., the session summary text 226) description of the sleep metrics data 418 and/or values thereof.

In one or more embodiments, evaluation of sleep metrics data 418, either for a sleep session or multiple sleep sessions, may result in unrequested improvement and/or sleep improvement intervention 180 opportunities which may be provided to the user 100. In one or more embodiments, the sleep session engine 220 may include an improvement reporting subroutine 224, which may include computer readable instructions that when executed report a sleep improvement intervention 180 to the user 100 through the voice interface 104 using the speaker 606 of the earphone 600.

In one or more embodiments, the sleep assistance server 200 may include a sleep assistance engine 240 configured to generate recommendations and/or sleep improvement interventions 180 following either or both of a request from the user 100 and/or an automatically generated internal request based on analysis of the sleep metrics data 418 (e.g., several sleepless nights in a row, increasing sleep onset latency metrics over a rolling seven-day period, etc.). In one or more embodiments, the request for sleep assistance (e.g., the sleep improvement request 170) may be resolved only utilizing data within the request 107 (e.g., the literal words of the user 100), and/or may be resolved with contextual data from the user profile 410, including previously stored sleep improvement request 170, physiological data 205, sleep session data 414, and/or sleep metrics data 418.

In one or more embodiments, the sleep assistance engine 240 may include computer readable instructions that when executed generates a prompt comprising data extracted from the sleep improvement request 170. For example, the prompt may be an input for a large language model such as the sleep assistance model 115. The prompt may include data extracted from the user profile 410. For example, if the user 100 requests assistance with sleep but provides no additional information, the user profile 410 may be referenced to determine, e.g., by inspection of one or more sleep session data 414, that the user 100 has been waking about two-to-three hours after falling asleep. This may be indicative of indigestion, acid reflux, and/or other issues related to digestion.

In the above example, a certainty of the sleep issue and/or the prescribed intervention may be relatively low. This can be measured through numerous methods. In one or more embodiments, an input may be fed into an artificial neural network several times and the outputs gathered and compared for similarity and/or divergence. Any random component and/or variation provided to the input may generate varying results. Where the results, as which may include predictive text, are similar or include restatements of the diagnosis and/or intervention, then sufficient information may be available to provide a productive intervention for the user 100 to attempt. Alternatively, where a substantial variation is shown between outputs (e.g., word choice or vocabulary, phrasing, length or complexity of response, levels of detail, and/or derived meaning), the information utilized may be insufficient, and the user 100 may be queried (e.g., through the voice interface 104) for additional information. A separate artificial neural network may be able to recognize and assess the similarity of outputs with training data comprising pairs or multiple associated outputs considered similar.

In one or more embodiments, the sleep assistance engine 240 may include a query submission routine 242, which may include computer readable instructions that when executed submit the prompt to a large language model (also abbreviated herein as an "LLM") comprising an artificial neural network (also abbreviated herein as an "ANN"), for example included within the sleep assistance model 115. The artificial neural network (ANN) of the sleep assistance model 115 may be trained with and/or fine-tuned with a training data including a text question related to sleep effectiveness paired with a text answer related to sleep effectiveness. In one or more other embodiments, an output of the artificial neural network may be a designation one or more categories of sleep issue (e.g., insomnia, indigestion, environmental disturbance, snoring partner, anxiety, etc.), which then may be paired with pre-formulated interventions. This may assist in providing clear, uniform instructions that can be adjusted after monitoring use and effectiveness for the entire population or a subpopulation of the users 100.

In one or more embodiments, the sleep assistance engine 240 may include a query receipt routine including computer readable instructions that when executed receive an output from the ANN of the sleep assistance model 115, the output including a predictive text of the sleep assistance model 115 (e.g., the predictive text 182). The predictive text may be human-readable narrative that may include a full description of the issue and/or its possible complete or partial solution, and/or may be a short label or type of a sleep issue which can be paired with prewritten interventions, depending on the training data used to train the sleep assistance model 115.

In one or more embodiments, the sleep assistance engine 240 may include an intervention generation routine 246. The intervention generation routine 246 may be configured to (i) assess the diagnosis of the sleep issue and/or formulation of a sleep improvement intervention 180 as competent, (ii) reformulate the sleep improvement intervention 180 into an easily understand and human-actionable set of steps for delivery over the voice interface 104, and/or (iii) pair the diagnosis with one or more prewritten sleep improvement interventions 180. Assessment of competence in the diagnosis and/or sleep improvement intervention 180 may be effected by a quality control artificial neural network which may assess the output of the sleep assistance model 115, as known in the art. Other methods for assessing quality and accuracy of AI model outputs that are known in the art may also be utilized. Similarly, the intervention generation routine 246 may reformulate the output, for example summarizing (reduction to 100 characters, 50 words, reformulation as ten or fewer key points each having twelve or fewer words, etc.). In one or more other embodiments, the output of the sleep assistance model 115 may be paired with preexisting sleep improvement interventions 180 written or assessed by sleep experts, and possibly specialized for succinct delivery through the voice interface 104.

In one or more embodiments, the sleep assistance engine 240 may include an intervention reporting subroutine 248 providing the predictive text of the sleep assistance model 115 (and/or prewritten diagnoses and interventions) to the user 100 through the voice interface 104 as a sleep improvement intervention 180. As just a few straightforward examples, the sleep improvement intervention 180 may include a decreased environmental noise (e.g., in the sleep environment 101), an increased sleep period, an earlier sleep time, a later awakening time, and utilization of a different audio data to generate the sleep assistance audio 102.

Sleep improvement interventions 180 may also be separated into actionable sub-steps provided at the outset of each sleep session to help assess individual variables that may impact sleep. For example, the National Institute of Health (NIH) may recommend multiple interventions for insomnia, but during a first sleep session the user 100 may be advised to "Make your bedroom sleep friendly. Sleep in a cool, quiet, dark place. Avoid watching TV or looking at electronic devices, as the light from these sources can disrupt your sleep-wake cycle."

The user 100 may be questioned on their implementation (or light and temperature data also may be assessed from one or more devices of the user 100 to determine compliance with "cool" and "dark"). If properly implemented at least to a threshold degree, the results may be evaluated for effectiveness (e.g., as further shown and described in conjunction with the intervention evaluation engine 260, below). During the next morning, the user 100 may be instructed, in accordance with NIH guidelines: "Get regular physical activity during the daytime, at least 5 to 6 hours before going to bed. Exercising close to bedtime can make it harder to fall asleep." This process may continue, with progress and evaluation tracked through the user profile 410.

In one or more embodiments, the sleep assistance server 200 may include a content evaluation engine 250 which may be configured to evaluate sleep assistance audio 102 for its effectiveness. Effectiveness key performance indicators (e.g., "sleep KPIs") may include any of the sleep metrics within the sleep metrics data in the sleep metrics data 418, and in one or more preferred embodiments, sleep onset latency, continuity of sleep (especially during environmental noise as may be detected by one or more microphones of one or more devices of the user 100), number and length of REM cycles, and/or total length of sleep. Effectiveness also may be determined entirely or in part by narrative feedback and/or ratings provided by the user 100, for example through the voice interface 104. In one or more embodiments, objective data such as the sleep metrics data 418 and the feedback of the user 100 may have a weighted importance in evaluating effectiveness.

In one or more embodiments, the content evaluation engine 250 may include a content effectiveness routine 252 which may include computer readable instructions that when executed determine an effectiveness value of the sleep assistance audio 102 utilizing the sleep metrics data 418 of a time period (e.g., the time period of sleep session data 414, or relevant portion when the sleep assistance audio 102 was being played for the user 100), compared against a general sleep metric baseline (e.g., the general sleep metric baseline data 225) and/or a user baseline sleep metric 417 generated with data comprising one or more previous time periods (e.g., from one or more sleep sessions). For example, the sleep assistance audio 102 may be determined effective where sleep onset latency was twenty minutes or fewer, and represented at least a 10% decrease in time from other sleep assistance audio 102 attempted by the user 100.

In one or more embodiments, the content evaluation engine 250 may include a user feedback routine 253 configured to query the user 100 and receive feedback on the sleep assistance audio 102. In one or more embodiments, the user feedback routine 253 may include computer readable instructions that when executed query the user 100 for an effectiveness rating of the sleep assistance audio 102 over the time period and/or a segment of the time period (e.g., a portion of the time over which the sleep session data 414 was generated). The time period, or a description of the time period, as well as a possible description of the sleep assistance audio 102, may be provided to the user 100 to help ensure feedback is adequately associated with the sleep assistance audio 102. For example, the user 100 may be asked through the voice interface 104: "Did the story you were told before you fell asleep help you to relax?", and/or "when you woke in the middle of the night, did the ambient sound of the forest help you fall back to sleep?". Alternatively, or in addition, the user 100 may be asked to provide a score on a sliding scale, for example how helpful the sleep assistance audio 102 was on a scale of one to five.

In one or more embodiments, the user feedback routine 253 may include computer readable instruction that when executed receive the effectiveness rating from the user 100. For example, the effectiveness rating may be a score (e.g., eight out of ten, a letter grade, a pass or fail grade, etc.). Other indicators may be assigned to indicate incomplete or uncertain effectiveness based on one or more other factors, and/or limiting applicability of the effectiveness determination to a certain context defined by the user 100 or otherwise determined (e.g., the user 100 is attempting to sleep on an airplane, bus, or boat). Alternatively, the user 100 may provide the effectiveness rating in the form of narration which may be assessed for positive responses and a numerical score assigned.

In one or more embodiments, the content evaluation engine 250 may include an evaluation storage subroutine 254 which may generate a sleep audio effectiveness data 421 by associating (i) at least one of the effectiveness value and/or the effectiveness rating with (ii) at least one of an identifier of an audio data of the sleep assistance audio 102 and/or an element of the sleep assistance audio 102. For example, the generative sleep content 800 may have been stored for future use pending evaluation (e.g., if the user 100 finds it highly effective, it can be used again or analyzed to be further refined; if the user 100 finds it ineffective, it can be discarded or analyzed to determine if certain elements are counterproductive to the sleep of the user 100). Alternatively or in addition, the text prompts leading to the output that was evaluated to be effective may be stored and associated with a unique identifier, which may be more efficient that audio storage and may generate a similar, although unlikely identical result unless the generative content models 120 are configured to be deterministic. In other words, a collection of prompts, rather than model output may be evaluated for effectiveness in assisting the user 100 with sleep. It should be noted that, in one or more embodiments, the content evaluation engine 250 may be evaluating preexisting content 510, such as a well-known song or soundtrack, in which case the sleep audio effectiveness data 421 may designate the preexisting content 510 through a unique identifier. The evaluation storage subroutine 254 may also include computer readable instructions that when executed store the sleep audio effectiveness data 421 in association with a user profile 410 of the user 100, for example as further shown and described in conjunction with the embodiment of FIG. 4.

The content evaluation engine 250 may include an effectiveness reporting routine 255 configured to report the effectiveness to the user 100, for example at an opportune time through the voice interface 104. In one or more embodiments, the effectiveness reporting routine 255 may include computer readable instructions that when executed report the effectiveness value to the user 100 upon determination the user 100 is in the concerned awake state (e.g., a concerted awake state at the end of, or terminating, a sleep session). For example, the user 100 may be informed, before or after soliciting feedback from the user 100, that the sleep assistance audio 102 helped the user 100 to achieve a 14% increase in sleep onset latency.

In one or more embodiments, elements and/or characteristics of sleep assistance audio 102 may be evaluated for effectiveness. For example, elements of content (e.g., an ambient sound, a music instrument, a particular waveform, low tonal ranges, etc.) and/or characteristics (e.g., style, genre, stylistic consistency, etc.) may be tracked and scored for effectiveness over one or more sleep sessions. It may be determined, for example, that despite the user 100 requesting certain sleep assistance audio 102, that certain frequency ranges and/or instruments (e.g., a piccolo) may disrupt initiation of sleep and increase sleep onset latency, for example when pairing the frequency ranges with elevating heart beat, increased respiration rate variability, etc. Other evaluations may include masking audio, particular masing sounds or waveforms, broad spectrum masks (e.g., white noise, pink noise, brown noise), and/or other sleep assisting audio known in the art.

In one or more embodiments, the element evaluation routine 256 may include computer readable instructions that when executed extract one or more elements (including without limitation generative elements) of at least one of the generative sleep content 800, such as the generative audio data, the narrative audio data 830, the narrative text data 832 associated with the narrative audio data 830, the music audio data 840, the ambient audio data 850, and/or one or more physiological guidance elements. The element evaluation routine 256 may then store the one or more generative elements in association with an element effectiveness value 234 and/or an element effectiveness rating 236. For example, storage may occur in an element evaluation database 251. In one or more embodiments, elements determined to be effective may be added as positive prompts within a generative sleep content request 700, and elements determined to be ineffective and/or counter-effective may be added as negative prompts (e.g., a request for an artificial neural network to exclude the subject matter of the negative prompt from the output and/or predictive output of the AI model). In one or more embodiments, the content evaluation engine 250 may generate an effectiveness summary text 257, which may be rendered as an effectiveness summary audio 258 and which may be included within the session summary audio 228 that may be reported to the user 100.

In one or more embodiments, the sleep assistance server 200 may include an intervention evaluation engine 260. The intervention evaluation engine 260 may be configured to produce one or more sleep improvement interventions 180 or aspects thereof for effectiveness in inducing, maintaining, and/or increasing quality of sleep. Effectiveness key performance indicators may include any of the sleep metrics within the sleep metrics data 418, and in one or more preferred embodiments, sleep onset latency, continuity of sleep (especially during environmental noise as may be detected by one or more microphones of one or more devices of the user 100), number and length of REM cycles, and/or total length of sleep. Effectiveness also may be determined entirely, or in part, by narrative feedback and/or ratings provided by the user 100, for example through the voice interface 104. In one or more embodiments, similar to evaluation of content effectiveness, objective data such as the sleep metrics data 418 and the feedback of the user 100 may have a weighted importance in evaluating effectiveness of each sleep improvement intervention 180 or portion thereof.

In one or more embodiments, the intervention evaluation engine 260 may include a intervention effectiveness routine 262 which may include computer readable instructions that when executed determine an effectiveness value of the sleep improvement intervention 180 utilizing the sleep metrics data 418 for a time period (e.g., the time period of sleep session data 414, or relevant portion when the sleep assistance audio 102 was being played for the user 100), compared against a general sleep metric baseline (e.g., the general sleep metric baseline data 225) and/or a user baseline sleep metric 417 generated with data comprising one or more previous time periods (e.g., from one or more sleep sessions). For example, the sleep improvement intervention 180 may be determined effective where the user 100 has fewer interstitial awake periods within the sleep session, where the user 100 achieves greater overall sleep, and/or where a positive trend in one or more sleep metrics is identified across two or more sleep sessions (e.g., by comparison of two or more sleep session data 418) upon continual practice of any steps or requirements described in the sleep improvement intervention 180.

In one or more embodiments, the intervention evaluation engine 260 may include an intervention quality routine 261 configured to effect quality control over implementation of the sleep intervention. In one or more embodiments, the intervention quality routine 261 may gather sensor inputs from one or more devices and/or receive answers from a questionnaire transmitted to the user 100 to determine if the sleep improvement intervention 180 was at least partially implemented. For example, where vigorous exercise ending at least four hours prior to an indented bedtime is including within the sleep improvement intervention 180, accelerometer sensor data from a smartwatch, a smartphone, and/or the earphones 600 may be used to disqualify an effectiveness evaluation of the sleep improvement intervention 180 for the sleep session of the user 100 for that night. Similarly, the user 100 may be queried with one or more questions about compliance and/or adherence to steps of the sleep intervention. For example, where the user 100 has an unusual bedtime and/or a specific shift in bedtime over several days, the user 100 may be asked if they switched to a different time zone. In such case, the user 100 may be proactively asked if they would like any sleep improvement intervention 180 related to ameliorating "jet lag."

In one or more embodiments, the intervention evaluation engine 260 may include a user feedback routine 263 configured to query the user 100 and receive feedback on the sleep improvement intervention 180 and any perceived effectiveness. In one or more embodiments, the user feedback routine 263 may include computer readable instructions that when executed query the user 100 for an effectiveness rating of the sleep improvement intervention 180 over the time period and/or a segment of the time period (e.g., a portion of the time over which the sleep session data 414 was generated). The time period, or a description of the time period, as well as a possible description of the sleep improvement intervention 180, may be provided to the user 100 to help ensure feedback is adequately associated with the sleep intervention. For example, the user 100 may be asked through the voice interface 104: "Did exercising in the afternoon, rather than in the evening, help you to sleep?". As another example, the user 100 may be asked: "Did covering all LED lights in your sleep environment help to you sleep?". Alternatively, or in addition, the user 100 may be asked to provide a score on a numeric scale as the helpfulness of the sleep improvement intervention 180.

In one or more embodiments, the user feedback routine 263 may include computer readable instruction that when executed receive the effectiveness rating from the user 100. For example, the effectiveness rating may be a score (e.g., eight out of ten). Alternatively, the user 100 may provide the effectiveness rating in the form of narration which may be assessed for positive responses and a numerical score assigned.

In one or more embodiments, the intervention evaluation engine 260 may include an evaluation storage subroutine 264 which may generate an intervention effectiveness data 423 by associating (i) at least one of the effectiveness value and/or the effectiveness rating with (ii) at least one of an identifier of a sleep improvement intervention 180, an identifier of a diagnosis, and/or an element of the sleep improvement intervention 180 such as a step, quality, or characteristic. For example, the sleep improvement intervention 180 may have been stored for future use pending evaluation (e.g., if the user 100 finds the sleep improvement intervention 180 highly effective, it can be used again or iteratively evolved to increase effectiveness; if the user 100 finds the sleep improvement intervention 180 ineffective, it can be discarded or recorded as already attempted within the user profile 410). Alternatively, or in addition, the text prompts leading to the output that was evaluated to be effective may be stored and associated with a unique identifier, which may be more efficient than audio storage and may generate a similar, although unlikely identical result unless the sleep assistance model 115 is configured to be deterministic, e.g., a collection of prompts, rather than model output may be determined to be effective for the assisting the user 100 with sleep. The evaluation storage subroutine 264 may also include computer readable instructions that when executed store the sleep audio effectiveness data 421 association with a user profile 410 of the user 100, for example as further shown and described in conjunction with the embodiment of FIG. 4.

The intervention evaluation engine 260 may include an effectiveness reporting routine 265 configured to report the effectiveness to the user 100, for example at an opportune time on the voice interface 104. In one or more embodiments, the effectiveness reporting routine 265 may include computer readable instructions that when executed report the effectiveness value to the user 100, for example upon a determination that the user 100 is in the concerned awake state (e.g., a concerted awake state at the end of, or terminating, a sleep session).

In one or more embodiments, elements or steps of the sleep improvement intervention 180 may be evaluated for effectiveness. For example, elements (e.g., limiting light, reducing consumption of stimulants, sound-based interventions, light-based interventions, consumption-based interventions, etc.) and/or steps may be tracked and scored for effectiveness over one or more sleep sessions. It may be determined, for example, that despite the user 100 following a protocol set forth in the sleep improvement intervention 180, some steps may be more important than others, and/or determinative in improving certain sleep metrics. Similarly to content evaluation, the physiological data 205, sleep session data 414, and/or sleep metrics data 418 may be utilized to determine which periods the sleep improvement intervention 180 impacted, and/or to what extent.

In one or more embodiments, the element evaluation routine 256 may include computer readable instructions that when executed extract one or more elements or steps from the sleep improvement intervention 180. The element evaluation routine 256 may then store the one or more elements or process steps in association with an intervention effectiveness value and/or an intervention effectiveness rating (e.g., stored within the intervention effectiveness data 423). Although not shown in FIG. 2, storage may occur in an intervention evaluation database. In one or more embodiments, elements or steps that may be determined to be effective may be added as positive prompts in association with a sleep improvement request 170, and elements determined to be ineffective and/or counter-effective may be added as negative prompts (e.g., a request for an artificial neural network to exclude the subject matter of the negative prompt from the predictive output of the sleep assistance model 115). In one or more embodiments, the intervention evaluation engine 260 may generate an intervention effectiveness summary text, which may be rendered as an intervention effectiveness summary audio and which may be included within the session summary audio 228 that may be reported to the user 100.

In one or more embodiments, the sleep assistance server 200 may include a sleep content coordination engine 270 which may be configured to mediate requests for sleep assistance audio 102. For example, where the request 107 for sleep assistance audio 102 is determined not to include a generative request, the content selection routine 272 may match a request for a preexisting audio track, or type of track (e.g., a request for an "ocean soundscape", where multiple preexisting audio tracks qualify), with one or more audio tracks, as may be known in the art. The sleep content coordination engine 270 may further include an effectiveness selection routine 274 that may be configured to evaluate predetermined effectiveness of sleep assistance audio 102, whether based on preexisting content 510 or generative content stored for later potential use. In one or more embodiments, the effectiveness selection routine 274 may include computer readable instructions that when executed determine that an effectiveness value of a potential selection is below a threshold value and/or an effectiveness rating of a potential selection is below a threshold rating, and then initiate the sleep assistance audio 102 selected and/or generated from a selection other than the potential selection. For example, the effectiveness selection routine 274 may query the sleep audio effectiveness data 421.

The sleep content coordination engine 270 may further include a generative content request routine 276 which may be configured to open and track any pending generative requests (e.g., the audio generation request 701), for example any sent to the generative content server 300. The generative content request routine 276 may include procedures for timeouts, request errors, and/or providing the user 100 with updates on generative requests, especially if generative requests and quality control thereof may take an indeterminate or variable amount of time between requests depending on complexity and/or the invoked generative content models 120.

In one or more embodiments, the sleep content coordination engine 270 may include a content delivery routine 278 configured to transmit and/or deliver the sleep assistance audio 102 to the user 100, for example on the earphones 600 or another device (e.g., a device 650 such as a smartphone). In one or more embodiments, the content delivery routine 278 which may be configured to transmit the sleep assistance audio 102 to the device 650 of the user 100 and/or store the sleep assistance audio 102 for later use in association with the user profile 410. The sleep assistance audio 102, including any generative sleep content 800, may have been received from the generative content server 300, for example as further shown and described below. In one or more embodiments, the content delivery routine 278 may include computer readable instructions that when executed transmit the generative audio data 801 to the earphone 600 (e.g., an earbud) of the user 100 to assist the user 100 in achieving at least one of relaxation and sleep through the customized audio.

FIG. 3 illustrates a generative content server 300, according to one or more embodiments. The generative content server 300 may include a processor 301 that may include one or more computer processors and/or central processing units (CPUs), and a memory 303 which may be a physical non-transient computer readable memory. The generative content server 300 may be communicatively coupled to the network 106. Although shown as discrete elements in FIG. 3, each of the engines, systems, routines, subroutines, agents, databases, data, and files may be communicatively coupled to one another, through the network, the memory 203, and/or other communication networks and/or communication buses.

In one or more embodiments, the generative content server 300 may receive one or more prompts parsed from the audio generation request 701 (e.g., the prompts 702, as may be further shown and described in conjunction with the embodiment of FIG. 7) for selection and/or creation of generative sleep content 800 that may be utilized as the sleep assistance audio 102.

In one or more embodiments, the generative content server 300 may include a generative content engine 320. The generative content engine 320 may be configured to receive one or more prompts (e.g., the prompts 702) and generate the generative sleep content 800 for use as, or to be included in, the sleep assistance audio 102. The generative content engine 320 may be communicatively coupled with and/or controlled by the sleep assistance OS 110. The generative content engine 320 may be communicatively coupled with one or more of the generative content models 120, the voice models 190, the user data 119 (e.g., stored on the profile server 400), and/or the preexisting content 510 (which may be stored on the preexisting content server 500). In one or more embodiments, the generative content engine 320 may include an effectiveness model guidance routine 321, a recorded query routine 324, a music prompt interpretation routine 326, a text generation routine 330, a voice generation routine 332, a music generation routine 340, an ambient generation routine 350, a physiological guidance generation routine 360, a guidance prioritization subroutine 328, and/or a text-audio element relation subroutine 329.

In one or more embodiments, the generative content engine 320 may be configured to initiate a file to gather inputs (e.g., one or more of the prompts 702 and/or engineered or adjusted input prompts 127) for the context window (e.g., the context window 126) or one or more of the generative content models 120. In one or more embodiments, the generative content engine 320 may include computer readable instructions that when executed initiate a retrieval augmented generation data, referred to as a session RAG data 124, for example use in association with the sleep session and assisting the user 100 to initiate or maintain sleep. The generative content engine 320 may call the model augmentation system 370 for a determination of any content or modification to be made in or to the session RAG data 124, for example adding data from a general sleep model augment data 122 and/or a user specific augment data 123, as further shown and described below and in conjunction with the embodiment of FIG. 7.

In one or more embodiments, the generative content engine 320 may be configured to gather and submit inputs to one or more generative content models 120. In one or more embodiments, the generative content engine 320 may include computer readable instructions that when executed submit one or more of the prompts 702 and the session RAG data 124 as inputs and/or within the context window 126 (e.g., as input prompts 127) of one or more of the generative content models 120, for example a large language model for narrative text generation. In one or more embodiments, the generative content engine 320 may be configured to gather and store outputs from the one or more generative content models 120. In one or more embodiments, the generative content engine 320 may include computer readable instructions that when executed output a predictive text based on the large language model prompts (e.g., the narrative prompt 730) and/or the session RAG data 124.

In one or more embodiments, the text generation routine 330 may be configured to generate an input prompt 127 for the text generation model 130, including utilization of the narrative prompt 730, the narrative modifier 732, the narrative style description 734, and/or the narrative genre description 736, as each are further shown and described in conjunction with the embodiment of FIG. 7. For example, the text data 830 to be generated may include a sleep story to help the user 100 to relax and/or fall asleep, including custom content, subject matter, and/or other requested narrative elements that the user 100 may request within the narrative prompt 730. In one or more embodiments, the text generation routine 330 may include computer readable instructions that when executed input the narrative prompt 730 into one or more text generation models 130 that include an artificial neural network of the text generation model 130, for example a large language model. In one or more embodiments, the text generation routine 330 may include computer readable instructions that when executed generate a text data 830 as the output of the artificial neural network of the text generation model 130. As further shown and described in conjunction with the embodiment of FIG. 8, additional quality control, filtering, and re-submission processes may be implemented to help ensure a competent output of the narrative and/or assist integration with one or more other generative aspects.

In one or more embodiments, the text data 830 may then be rendered into speech, for example utilizing the text-to-speech model 192 and/or a custom voice model 194. In one or more embodiments, the voice generation routine 332 may include computer readable instructions that when executed input the text data 830 into a text-to-speech model 192 and may output a narrative audio data 832. The text-to-speech model 192 may additionally utilize the custom voice model 194 to render the text data 830 as audio in a customized and particular voice.

In one or more embodiments, the physiological guidance generation routine 360 may be configured to generate an input prompt 127 for the physiological guidance model 160, including utilization of the physiological guidance prompt 760, the physiological guidance modifier 762, and/or the physiological guidance type 764, as each are further shown and described in conjunction with the embodiment of FIG. 7. For example, the physiological guidance prompt 760 may include custom requests for physiological guidance, including integration into one or more other aspects of generative content, such as blending the physiological guidance into the structure of the text data 830 and/or the narrative audio data 832, the music audio data 840, and/or the ambient audio data 850. In one or more embodiments, the physiological guidance may include breathing exercises and/or heartrate control.

In one or more embodiments, the text generation routine 330 may include computer readable instructions that when executed input the physiological guidance prompt 760 into a physiological guidance model 160, which may include an artificial neural network of the physiological guidance generation model 160. In one or more embodiments, the text generation routine 330 may include computer readable instructions that when executed generate a physiological guidance template 860 as an output of the artificial neural network of the physiological guidance model 160. The physiological guidance may include one or more physiological guidance elements, for example an inhalation event, a hold breath event, an exhalation event, a stretch of a muscle, etc.

In one or more embodiments, the music generation routine 340 may be configured to generate an input prompt 128 for the music generation model 140, including utilization of the music prompt 740, the music filter 743, the music style description 744, and/or the music genre description 746, as each are further shown and described in conjunction with the embodiment of FIG. 7. For example, the music prompt 740 may include requests for custom music, including being supportive of and/or enhancing a narrative within the text data 830, the narrative audio data 832, and/or the ambient audio data 850.

In one or more embodiments, the music generation routine 340 may include computer readable instructions that when executed input the music prompt 740 into a music generation model 140, which may include an artificial neural network of the music generation model 140. The music generation model 140 may be trained with training data that include associations between text tokens and musical elements, in one or more embodiments. In one or more embodiments, the music generation routine 340 may include computer readable instructions that when executed generate a music audio data 840 as an output of the artificial neural network of the music generation model 140.

In one or more embodiments, the generative audio data 801 may include an overlay of the music audio data 840 and the narrative audio data 832, for example as coordinated by the content integration engine 380.

In one or more embodiments, the ambient generation routine 350 may be configured to generate an input prompt 127 for the ambient sound generation model 150, including utilization of the ambient sound prompt 750, the ambient filter 153, and/or the ambient style description 754, as each are further shown and described in conjunction with the embodiment of FIG. 7. For example, the ambient sound prompt 750 may include requests for custom sound effects, custom arrangement or combination of sounds (e.g., an outdoor party with people talking in addition to the sound of crickets), including supportive of and/or enhancing a narrative or music, as may be further coordinated by the content integration engine 380.

In one or more embodiments, the ambient generation routine 350 may include computer readable instructions that when executed receive an ambient modifier 752 including an ambient filter 753 and/or an ambient style description 754. In one or more embodiments, the ambient generation routine 350 may include computer readable instructions that when executed input the ambient sound prompt 750 and any ambient modifier 752 into an ambient sound generation model 150, which may include an artificial neural network of the ambient sound generation model 150. The ambient sound generation model 150 may be trained with training data that includes associations between text tokens and one or more sound elements. As known in the art, text tokens may include groups of one or more characters (including letters, spaces, punctuation, and/or other characters) usable for generating predictive text. In one or more embodiments, the ambient generation routine 350 may include computer readable instructions that when executed generate the ambient audio data 850 as an output of the artificial neural network of the ambient sound generation model 150.

In one or more embodiments, the generative content engine 320 may include computer readable instructions that when executed transmit the generative audio data 801 for utilization by the earphone 600 (e.g., an earbud) of the user 100, for example to assist the user 100 in achieving at least one of relaxation and sleep through the customized audio. For example, the generative content engine 320 may forward the sleep assistance audio 102 and/or the sleep assistance audio 102 to the sleep assistance server 200, e.g., for storage, delayed delivery, on-demand delivery, and/or immediate delivery via the content delivery routine to one or more devices of the user 100 such as the earphones 600.

In one or more embodiments, the generative content engine 320 may include a guidance prioritization subroutine 328 configured to prioritize, emphasize, and/or enforce the physiological guidance template in the generative process of the generative content models 120, for example by constraining additional outputs of the text generation model 130, the music generation model 140, and/or the ambient sound generation model 150 such that the physiological guidance and/or the physiological guidance template 864 is maintained as a competent cue for physiological guidance. As an example, it may be beneficial for the user 100 for the ambient sounds to reinforce the physiological guidance cues, rather than conflict, mask, or detract from the physiological guidance cues.

In one or more embodiments, the guidance prioritization subroutine 328 may constrain the output of the artificial neural network of the ambient sound generation model 150 to produce an ambient audio data 850 in which an ambient element (e.g., a sound, a nature sound, an environment sound) is temporally associated with a physiological guidance element (e.g., a cue or pattern of related cues defining a single physiological event, such as a respiration cycle). As just one example, a nature soundscape may include a cicada sound, where the cicada hums loudly when the user 100 is to breath in, is silent when the user 100 is to hold their breath, and then initiate a soft descending hum when the user 100 is to breath out. In yet another example, respiration rate variability may be guided by the tone, amplitude, and/or other acoustical properties of elements within simulated background noise, such as a busy coffee shop or sounds of a cityscape. The intended effect may include for the user 100 to consciously notice the cues, subconsciously follow the cues, and/or potentially either depending on the attention and wakefulness of the user 100. For example, in one or more preferred embodiments, it may be advantageous to define physiological cues that are noticeable when the user 100 is actively engaged in physiological guidance exercises, but easy to ignore once no longer needed or desired.

In one or more embodiments, the guidance prioritization subroutine 328 may include computer readable instructions that when executed constrain the output of the artificial neural network of the music generation model 140 to produce music audio data 840 in which a musical element (e.g., a note, a musical phrase) is temporally associated with a physiological guidance element. In a straightforward example, the music may be generated in 4:4 time to approximate a 4-7-8 breathing exercise, with one beat assigned to each second (e.g., the result possibly including, for example, a 5-7-8 breathing exercise likely to provide similar benefits but within a familiar and subconsciously recognizable music structure). This incorporation of cues may both aid the user 100 in not being distracted by an unusual music structure, and may also assist in artificial neural network in predictive competence, for example due to possible prevalence of music having 4:4 time within a general and/or base model training dataset. In the present example, the inhalation phase may have an ascending scale, the hold phase a few varying and soft notes, and the breath out phase a descending scale. This general structure then may be able to be instantiated as having varying melodies and accompaniment. As a result, the music may have reduced repetition, yet still include a recognizable structure engraining the physiological guidance for the user 100.

In one or more embodiments, the guidance prioritization subroutine 328 may include computer readable instructions that when executed constrain the output of the artificial neural network of the text generation model 130 to produce the text data 830 in which a text clause of the text data 830 is temporally associated with a physiological guidance element. It will be noted that the text clause, which may end on punctuation such as a comma, period, question mark, exclamation mark, hyphen, colon, semicolon, etc., may approximate temporal association within the text data 830 and further refined during a text-to-speech process, in which audio may be precisely aligned with the physiological guidance template. The text-to-speech model 192 may then generate the narrative audio data 832 such that a voiceover of the text data 830 is temporally associated with a physiological guidance element. For example, speech rendering may be compressed or expanded to achieve proper temporal timing with the physiological guidance template. Where the text data 830 has been prepared to approximate the physiological guidance template, this may occur with little or no recognition by the user 100, who may remain unaware of the audio transformation.

In one or more embodiments, the recorded query routine 322 may be configured to gather and one or more preexisting and/or prerecorded contents, for example text or audio, for use as an input to one or more of the generative content models 120. In one or more embodiments, the recorded query routine 322 may include computer readable instructions that when executed query a preexisting audio comprising at least one of a recorded narrative audio 520, a prewritten narrative text 530, a recorded music audio 540, a recorded ambient audio 550, and/or a recorded physiological guidance audio 560.

In one or more embodiments, the generative content server 300 and/or the generative content engine 320 may include a content integration engine 380. The content integration engine 380 may be configured to integrate one or more outputs (e.g., the outputs 810) from the generative content models 120 such that audio elements are synchronized, and with no adverse thematic, stylistic, and/or audio effects resulting from integration. As one example, the content integration engine 380 may evaluate and remove any repetitive waveforms occurring, canceling waveforms, reinforcing waveforms, and/or masked waveforms occurring in each of one or more audio data. Prioritization may be assigned to some components (e.g., narrative) and less to others (e.g., ambient sound). The content integration engine 380 and various processes that may be effected thereby are further shown and described in conjunction with the embodiment of FIG. 8, and throughout the present embodiments.

In one or more embodiments, the content integration engine 380 may overlay and/or merge two or more audio data such as audio files or portions thereof. In one or more embodiments, the content integration engine 380 may include computer readable instructions that when executed generate the generative audio data 801 comprising an overlay of one of type of generative audio data 801 (e.g., the narrative audio data 832, the music audio data 840, the ambient audio data 850) and audio generated from the physiological guidance template 864. As one example, a music track or ambient audio track may be merged or "flattened" with a rending of the physiological guidance template 864 such as a voiceover of breathing exercises. However, in one or more embodiments, the audio tracks may be aligned but kept discrete, for example to be concurrently played as separate channels in a digital-to-analog (DAC) converter. Retaining individual audio data within the sleep assistance audio 102 may enable the user 100 to control the volume and/or other acoustic properties of each track separately. For example, the user 100 may instruct over the voice interface 104 to "please remove the ambient sound", or "please turn down the music so I can hear the story better," and such controls may be implemented without re-generation of the sleep assistance audio 102 and/or application of audio filters which may affect more than the intended target audio.

In one or more other embodiments, the integration of physiological guidance may occur through serialization of the inputs and output from one or more of the generative content models 120. For example, the physiological guidance template 864 or a text description thereof may be provided within the context window 126 and/or the input prompts 127 for generation of one or more audio data and/or data renderable into audio data such as text or music descriptions. In such case, the content integration engine 380 may include or call the physiological guidance generation routine 360, according to one or more embodiments.

The content integration engine 380 may be configured to integrate preexisting content 510, either with other preexisting content 510 (e.g., a recorded narrative audio 520 with a recorded ambient audio 550) and/or with generative content. In one or more embodiments, the content integration engine 380 may include computer readable instructions that when executed integrates preexisting and/or prerecorded audio with generative audio.

In one or more embodiments, the generative content engine 320 may include an effectiveness model guidance routine 321 which may be configured evaluate text, audio, and/or elements thereof for previously assessed effectiveness prior to providing input prompts 127 to the generative content models 120 and/or input nodes 128. The evaluated effectiveness may be tracked at several levels, including prompts 702 being input into the generative content models 120 and/or analyzed outputs of the generative content models 120. As just one example, an input prompt 127 including "electronica" or "synthesized style" may be determined to be ineffective for the user 100, whereas analysis of music audio data 840 as an output 810 may determine that certain patterns, sounds, and/or "instruments" may be ineffective. Such effectiveness evaluation may be further shown and described throughout the present embodiments. In one or more embodiments, the generative content engine 320 may query the user profile 410 to determine the effectiveness value, effectiveness rating, and/or a combined effectiveness score of one or more prompts or audio elements prior to utilization in an input prompt 128. Potential input prompts 127 determined to be ineffective may be removed, deemphasized, or deleted, whereas highly effective potential input prompts 127 may be added back in, unless either such addition or removal directly conflicts with the request of the user 100 (e.g., the user 100 included the word “synthesized” in the generative sleep content request 700).

In one or more embodiments, the effectiveness model guidance routine 321 may include computer readable instructions that when executed determine that the effectiveness value 323 is below a threshold value 325 and/or determine that an effectiveness rating is below a threshold rating. For example, where the effectiveness value 323 and the effectiveness rating may be hybridized into an effectiveness score, it may be similarly determined that the effectiveness score is below an effectiveness threshold score. The effectiveness model guidance routine 321 may generate generative sleep content 800 without utilizing those prompts, elements, and/or audio elements previously determined to be ineffective.

In one or more embodiments, it will be noted that audio elements determined to be ineffective may be isolated and described with text descriptions (e.g., “reverse prompted”), for example with an artificial neural network trained to recognize and describe using text any of the audio elements that were determined to be ineffective (and/or trained to recognize and describe other usable input prompts 127 for the generative content models 120 that were ineffective). For example, when a certain waveform is determined to increase the respiration rate and/or heart rate of the user 100 consistently through pairing and comparison of the sleep session data 414 with the generative sleep content 800, the waveform may be bounded, extracted, and input into the artificial neural network trained to associated sounds with text descriptions. For example, it may be determined that the waveform encodes a the sound characteristic of a bagpipe. As a result, data may be stored in association with the user profile 410 to designate the description or elements thereof as an ineffective prompt 702 and/or music prompt 740.

In one or more embodiments, the generative content server 300 includes a model augmentation system 370. The model augmentation system 370 may be configured to augment the audio generation request 701 and extracted prompts 702 thereof with additional context, as may be queried and copied from a general sleep model augment data 122 and/or a user specific augment data 123. In one or more embodiments, the model augmentation system 370 may include a general augmentation routine 372 configured to utilize a general sleep model augment data 122 in augmenting the audio generation request 701 and/or input prompts 127. For example, data from the general sleep model augment data 122 may be queried and added to the session RAG data 124, the context window 126, and/or may be utilized as input prompts 127. As one example, the general sleep model augment data 122 may include text and/or prewritten prompts highly correlated with effective generative content model 120 output results, and may therefore be used to supplement and/or engineer the input prompts 127. The general sleep model augment data 122 may be utilized as a default prompt engineering dataset for a large population of the user 100. In a straightforward example, the general sleep model augment data 122 may include text for positive prompts applying to music generation such as “calm,” “smooth transitioning”, “background”, “melodic”, and negative prompts such as “exciting”, “abrupt”, “heavy metal”.

The general sleep model augment data 122 may store prompts or other descriptors in discrete categories which can be separately queried upon a determination a given generative category (e.g., physiological guidance, narrative text, music, ambient, other) applies. For example, in one or more embodiments, the general sleep model augment data 122 includes a general physiological guidance augment data, a text RAG data 134, a music RAG data 144, an ambient RAG data 154, and/or a general augment voice data that may be usable for the voice-to-speech model 192. The text RAG data 134, the music RAG data 144, and the ambient RAG data 154 may be utilized for a general population of users 100, for example as examples of the general sleep model augment data 122 or portions thereof. In one or more embodiments, the general augmentation routine 374 may include computer readable instructions that when executed extract a subset of the general sleep model augment data 122 based on textual association with the audio generation request 701 and load the subset of the general sleep model augment data 122 into prompts 702 and/or input prompts 127 for use with an artificial neural network and/or a context window 126 of the artificial neural network. As further shown and described in conjunction with the embodiment of FIG. 7, optional mediation and/or deconfliction in prompts may occur, where either the audio generation request 701 and/or the general sleep model augment data 122 is given priority.

In one or more embodiments, the model augmentation system 370 may include a specific augmentation routine 374 configured to utilize a user specific augment data 123 in augmenting the audio generation request 701 and/or input prompts 127. For example, data from the user specific augment data 123 may be queried from the user profile 410 or a database associated with the user profile 410 and added to the session RAG data 124, the context window 126, and/or may be utilized as input prompts 127. As one example, the user specific augment data 123 may include text and/or prompts correlated with effective generative content model 120 output for the user 100 who generated the generative sleep content request 700. The user specific augment data 123 therefor may used to supplement and/or engineer the input prompts 127, including amending over and/or higher prioritization than the general sleep model augment data 122. For example, the user specific augment data 123 may store preferences of the user 100, either use as potential prompts 702, reverse-translated outputs described for use as prompts 702, prompts 702 determined to be effective or ineffective, etc. Similar to the general sleep model augment data 122, the user specific augment data 123 may include a data structure organizing types of prompts into categories for query efficiency. As further shown and described in conjunction with the embodiment of FIG. 7, optional mediation and/or deconfliction in prompts 702 may occur, where one of the audio generation request 701, the general sleep model augment data 122, and/or user specific augment data 123 may be given priority or priority with respect to certain generative categories. In one or more preferred embodiments, the prioritization may be: (i) the audio generation request 701, (ii) the user specific augment data 123, and (iii) the general sleep model augment data 122.

In one or more embodiments, the specific augmentation routine 374 may include computer readable instructions that when executed query the user profile 410 and load a description of an audio data and the effectiveness rating and/or the effectiveness value into the session RAG 124. In one or more embodiments, the specific augmentation routine 374 may include computer readable instructions that when executed query a user specific augment data 123 (which may include a user augment narrative data, a user augment music data, a user augment ambient data, and/or a user augment voice data) and extract a subset of the user specific augment data 123 relevant to the audio generation request 701. In one or more embodiments, the specific augmentation routine 374 may include computer readable instructions that when executed overwrite at least some of the subset of the general sleep model augment data 122 within the input prompt 128 of the artificial neural network and/or the context window 126 of the artificial neural network, and load the subset of the user specific augment data 123 into the input nodes 128 of the artificial neural network and/or the context window 126 of the artificial neural network.

In one or more embodiments, the generative content server 300 may include a music prompt interpretation routine 326 configured to generate music from a non-music request and/or non-music prompt 702, for example that of a narrative prompt 730. Music and/or ambient sound may be advantageous even when not requested, for example to supplement a sleep story primarily defined (or understood by the user 100 to be defined) by narrative. In one or more embodiments, the music prompt interpretation routine 326 may include computer readable instructions that when executed generate, if the music prompt 740 was not present when the audio generation request 701 was parsed, the music prompt 740 by inputting the narrative prompt 730 into a text-music relation model 352 relating a text to at least one of one or more musical elements, one or more music style descriptions 744, and/or one or more music genre descriptions 746. In one or more embodiments, a similar process may be utilized to generate unrequested ambient sound.

In one or more embodiments, one or more of the generative content models 120 may be retrained and/or data augmenting the generative content models 120 may be continuously or periodically updated based on effectiveness determinations and/or other determinations of competence and efficiency. In one or more embodiments, "retraining" a generative content model 120 may first include updating the general sleep model augment data 122 for use in prompt engineering and/or context window prompt expansion; second, fine-tuning a base model (e.g., the text generation base model 132) through node weight adjustment based on exemplars of competent training data (including through a low rank adaptation model); and/or third, optionally training a new base model with an expanded training dataset.

In one or more embodiments, the generative content server 300 may include a model training engine 390 that may be configured to amend the general sleep model augment data 122 and/or retrain one or more of the text generation models 130. In one or more embodiments, the training data may include prompts 702 and associated effectiveness scores (effectiveness values and/or effectiveness ratings) that may have been collected over a plurality of sleep session and in association with a population of users 100 and/or demographically related subpopulations thereof. Such feedback, combined with the physiological and sleep metric effectiveness analysis, may enable the generative content models 120 to continually improve at creating effective and custom sleep content for a wide population of users 100.

In one or more embodiments, the model training engine 390 may include computer readable instructions that when executed retrain (including possible readjustment of one or more parameters of) the artificial neural network of the text generation model 130, the artificial neural network of the music generation model 140, the artificial neural network of the physiological guidance model 160, and/or the artificial neural network of the ambient sound generation model 150. Adjusting the parameter may include modifying a node weight of an ANN node of these artificial neural networks. Adjusting a parameter may adjust a weight value of at least one node of the set of input nodes, the set of hidden nodes, and/or the set of output nodes. Where a base model is being fine-tuned, the fine tuning routine 392 may similarly effect fine-tuning utilizing the training dataset, as known in the art of AI model construction and training. The retrained models may be put back into production as the generative content models 120.

In one or more embodiments, one or more of the ANNs shown or described herein may include a feed-forward neural network. In one or more embodiments, the ANN may include a transformer model applying pairwise convolutional comparisons to groups of tokens, for example text tokens, music tokens, physiological guidance tokens, ambient sound tokens, and/or other tokens. In one or more embodiments, the ANN may include a self-attention layer applying one or more other ANNs or linear algebraic transformation to determine relatedness of pairs or groups of tokens, such as text tokens, music tokens, and/or ambient sound tokens. The transformer may include an encoder and a decoder. The decoder may utilize semi-supervised learning, for example unsupervised training on a large dataset and then supervised learning on a selected or smaller dataset (e.g., specialized for sleep).

In one or more embodiments, the artificial neural network may include a convolutional neural network ("CNN"). The CNN may be especially useful for recognition functions, as shown and described herein. For example, the CNN may be utilized to implement recognition of a type of request 107, recognition of relevant prompts 702 to be extracted from a request 107, recognition of patterns in physiological data, recognition of physiological events within physiological data, recognition of physiological features based on physiological event, recognition of sleep conditions based on sleep metrics (and/or physiological data, events, and/or features), and/or recognition of potential interventions based on sleep metrics (and/or physiological data, events, and/or features).

In one or more embodiments, the ANN may include a recurrent neural network ("RNN"). For example, the RNN may be utilized to evaluate sequence data within a physiological guidance template (e.g., a sequence of cues occurring over a temporal domain), sequence data for ambient sound, and/or sequence data for music. For instance, sequence data input into the RNN may include evaluation of order, context, and/or timing, according to one or more embodiments. In one or more embodiments, one or more of the present AI models may be configured as a Kolmogorov Arnold Network utilizing direct rather than approximate function representations.

Figure 4:
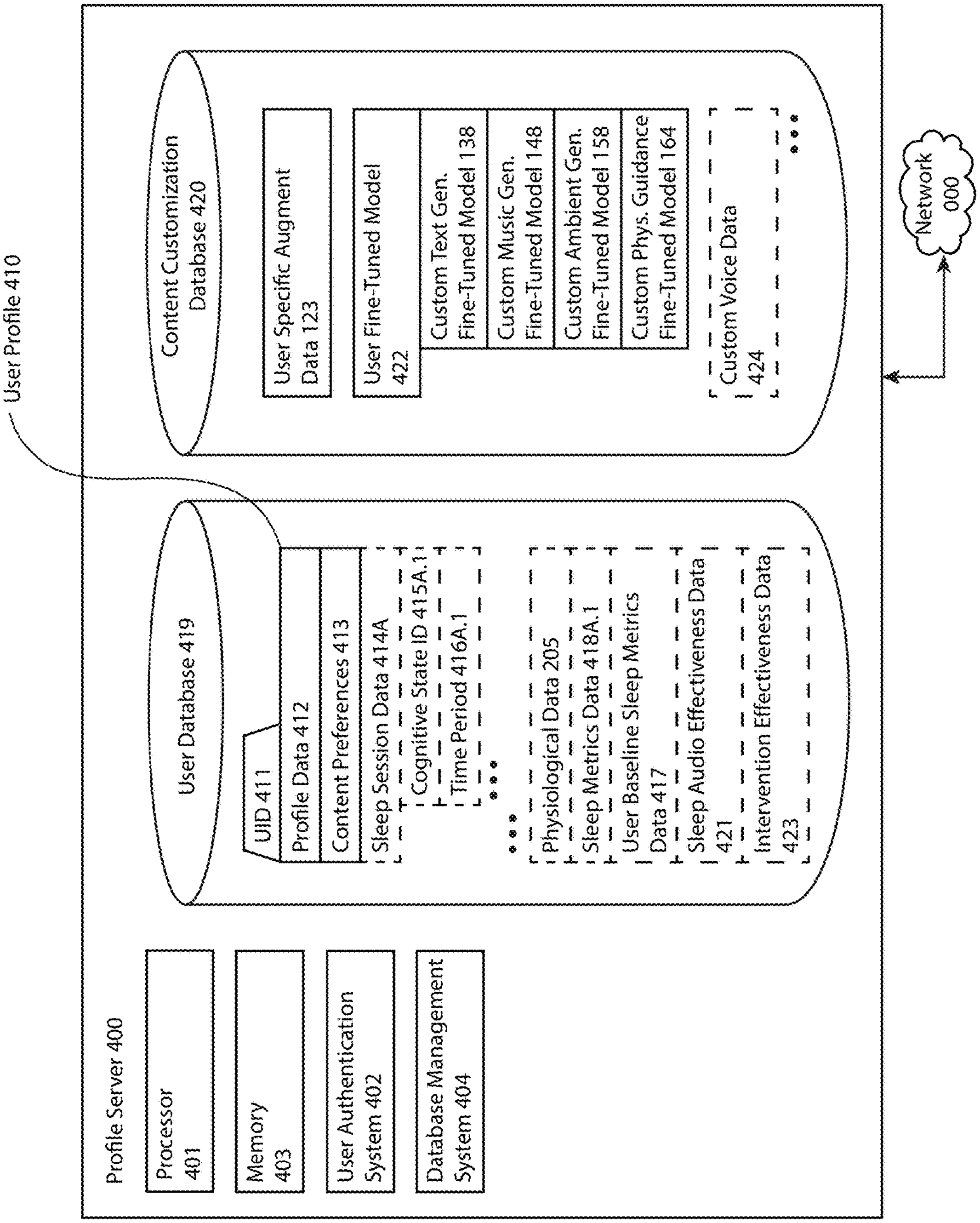
FIG. 4 illustrates a profile server including a user database storing sleep session data for one or more sleep sessions, sleep metric data for one or more sleep sessions, and/or user baseline sleep metrics, each of which may be usable to help evaluate effectiveness of generative content and/or sleep improvement interventions 180, and the profile server optionally including a content customization database including data to customize input prompts, customize the generative model to be applied, and/or model outputs to the individual needs of the user, according to one or more embodiments.

FIG. 4 illustrates a profile server 400, according to one or more embodiments. The profile server 400 may include a processor 401 that may include one or more computer processors and/or central processing units (CPUs), and a memory 403 which may be a physical non-transient computer readable memory. The profile server 400 may be communicatively coupled to the network 106. Although shown as discrete elements in FIG. 4, each of the engines, systems, routines, subroutines, agents, databases, data, and files may be communicatively coupled to one another, through the network, the memory 203, and/or other communication networks and/or communication buses.

The profile server 400 may include a user authentication system 402 configured to authenticate the user 100, a device 650 of the user 100, and/or earphones 600 such as an earbud. The device 650, for example may be a computer, a smartwatch, a smartphone (e.g., an iPhone, an Android® device, etc.). In one or more embodiments, the device 650 of the user 100 may include a microphone and a speaker on which the voice interface 104 may be implemented, and/or may be communicatively coupled to the earphones 600 including possibly through a wireless connection (e.g., Bluetooth®, WiFi, LTE and/or other local or long-range wireless protocols). The user authentication system 402 may effect authentication for the user 100 to log into an interface enabling management and updates to the user profile 410, to ensure proper formulation, delivery, and/or effectiveness evaluation for the sleep assistance audio 102, generative sleep content 800, the generative audio 801, and/or sleep improvement interventions 180. To streamline the experience of the user 100 in interfacing with the sleep evaluation and assistance network 199, a device ID (e.g., a device ID of the earphones 600 and/or a smartphone paired with the earphones 600) may be permanently or temporarily associated with the profile UID 411 of the user profile 410 of the user 100, for example such that use of the earphones 600 or paired device 650 automatically authenticates the user 100.

In one or more embodiments, the profile server 400 may include a database management system 404. The database management system 404 may be a commercial database management system usable to receive requests or queries and generate create, read, update, and/or delete operations for the user database 419 and/or content customization database 420. The database management system 404 may be a commercial database such as a relational and/or an SQL database, a document database (e.g., MongoDB), a columnar database (e.g., Cassandra), a key-value store, etc. In one or more embodiments, the profile server 400 may include a user database 419 which may store the user profiles 410 associated with each of one or more users 100 of the populations of users 100. In the embodiment of FIG. 4, an example of one of the user profiles 410 associated with a single user 100 is illustrated.

The user profile 410 may include a profile UID 411 enabling the user profile 410 to be uniquely addressed within a database, and/or may be utilized to associate data on one or more other devices and systems with the user profile 410 and its associated user 100. The profile UID 411, for example, may be a random string of 32 characters and/or a GUID as may be known in the art. In one or more embodiments, the user profile 410 may include a set of content preferences 413 that may be a set of data specifying general preferences of the user 100, either positive, negative, gradations of each, and/or neutral designations. The content preferences 413 may be sleep content preferences determined through questioning the user 100 at the time the user profile 410 is set up, through periodic query to the user 100, through evaluation of usage and feedback response, and/or through other interaction or evaluation of the actions of the user 100. Data from the content preferences 413 may be copied and/or translated through mappings into negative and/or positive prompts for user 100 in the user specific augment data 123, according to one or more embodiments. This may enable a static, user-readable set of preferences that can be mapped with evolving or refining data within the user specific augment data 123. For example, if the user 100 has a negative preference for country music (when attempting to sleep, e.g., the user 100 may get too excited due to certain memories or associations with the music), the content preferences 413 may list "country", but the user specific augment data 123 may list a set of negative prompts discouraging not only country but qualities of country music (e.g., "sharp string release" which may be common and distinct characteristic of country guitar music).

In one or more embodiments, the user database 419 may include a set of sleep session data 414 for each sleep session, e.g., the sleep session data 414A through the sleep session data 414N. For example, the user 100 may have one sleep session data 414 associated with each night, and some extra instances associated with naps. In one or more embodiments, the sleep session data 414 may include time series data of a cognitive state ID 415 of the user 100 over a time period associated with a time period ID 416. The sleep session data 414 may include a set of sequential time periods of arbitrary length paired with the corresponding cognitive state ID 415 of the user 100. For example, the sleep session data 414A may include a first time period 416A.1 with a corresponding cognitive state 415A.1 (e.g., a pre-sleep state in which the sleep session was initiated), a second time period ID 416A.2 with a corresponding cognitive state 415A.2 (e.g., fifty minutes of an NREM sleep state, not shown in FIG. 4), a third time period 416A.3 with a corresponding cognitive state 415A.3 (e.g., seventy two minuets of a REM state), etc.

The sleep session data 414 may also include more granular data than cognitive state, such as a time-sequenced set of physiological events (e.g., a heartbeat, a respiration event, a breath in, a held breath, an exhalation, a macro movement of the user 100) and/or data abstracted therefrom, such as an instantaneous heartrate, and heart rate variability, respiration rate, and/or respiration rate variability, as each may be calculated from rolling evaluations of two or more physiological events. In one or more embodiments, the sleep session data 414 may also track time series environmental data from the sleep environment 101, such as ambient temperature, environmental sounds, environmental light, and other physical data potentially or typically affecting sleep quality. In one or more embodiments, the sleep session data 414 may also store data about which sleep assistance audio 102 was or is being played by the user 100 for the sleep session, including synchronization of playback or playthrough times for audio aligned with cognitive state identifier 415 (e.g., shown as the cognitive state ID 415) within each of the time periods 416.

In one or more embodiments, the user profile 410 may include the physiological data 205, for example gathered by the one or more physiological sensors 612 and/or may include physiological events determined from analysis thereof, e.g., as shown and described in conjunction with the embodiments of FIG. 2. The user profile 410 may further include sleep metrics data 418, which also may be associated with each instance of the sleep session data 414. A user baseline sleep metrics data 417 may include established averages, medians, and/or other baselines from multiple instances of the sleep metrics data 418, including over all of time (e.g., every recorded sleep session data 414) and/or over some of the sleep session data (e.g., the last thirty days, the last thirty sleep sessions, etc.).

In one or more embodiments, the user profile 410 may additionally store a sleep audio effectiveness data 421 storing data specifying effective, neutral, and/or ineffective instances of the sleep assistance audio 102, whether preexisting or generative. The sleep audio effectiveness data 421 may associate the effectiveness value, effectiveness ratings, and/or hybrid effectiveness scores with input prompts 127, identifiers of stored instances of content (e.g., UIDs of preexisting or UIDs assigned to stored generative content such as the generative sleep content 800), and/or elements thereof serviced from analysis of generative content model 120 outputs (e.g., narrative elements, musical elements, acoustical properties, etc.).

In one or more embodiments, the user profile 410 may also store an intervention effectiveness data 423. The intervention effectiveness data 423 may associate the effectiveness value, effectiveness ratings, and/or hybrid effectiveness scores with: prompts used with the sleep assistance model 115, identifiers of stored instances of intervention content (e.g., UIDs of preexisting or UIDs assigned to stored generative interventions), and/or elements thereof derived from analysis of the sleep assistance model 115 output (e.g., breathing exercises incorporated within the sleep intervention, environmental light-based controls, etc.).

In one or more embodiments, the profile server 400 may include a content customization database 420. In one or more embodiments, the content customization database 420 may include data usable to customize and/or improve response to generative sleep content requests 700. Data within the content customization database 420 may be associated with the user profile 410 of an appropriate user 100 (and/or may be stored within the user profile 410, in one or more other embodiments). In one or more embodiments, the content customization database 420 may include the user specific augment data 123. In one or more other embodiments, the content customization database 420 may include a user fine-tuned model 422 which may store a custom fine-tuned instance of a generative content model 120 (e.g., the custom text generation fine-tuned model 138, the custom music generation fine-tuned model 148, the custom ambient generation fine-tuned model 158, and custom physiological guidance fine-tuned model 164, etc.). It will be recognized that a base model and/or fine tuned model comprising an artificial neural network may take a relatively large amount of storage space and/or other computing resources to train, store, and utilize. However, data size and training cost may be rapidly decreasing. In addition, new methods of "lightweight" fine tuning, including for example low rank adaptations (LoRAs) and other techniques known in the art, may significantly reduce the time, computing resources, and expense of custom fine-tuning. Therefore, in one or more embodiments, one or more custom fine-tuned model may be trained, generated, and stored, either for a particular user 100 and/or a subpopulation of users 100. As one example, a user 100 with over 2 years of sleep data may have such data and/or high-confidence effectiveness evaluations related thereto incorporated (or "fixed") into one or more generative content models 120 through custom fine-tuning. This also may be utilized for higher value and/or higher price services, which may increase query times and offset user fine-tuned model 422 and other computing resources storage fees. In one or more other embodiments, it will be recognized that the user fine-tuned model 422 may be utilized for a subpopulation of users 100. For example, fine tuning may be used to specialize one or more of the generative content models 120 for certain cultures, nations, languages, lifestyles, preference sets (e.g., as determined from the content preferences 413) and/or other demographic data based on utilizing training data associated with such sub-populations. In one or more embodiments, the user fine-tuned model 422 may include the custom text generation fine-tuned model 138, the custom music generation fine-tuned model 148, the custom ambient generation fine-tuned model 158, and/or the custom physiological guidance fine-tuned model 164. In such case, the user profile 410 may reference a unique identifier of the user fine-tuned model 422 to be utilized, and/or the user fine-tuned model 422 or associated data may reference each of the user profiles 410 which the user fine-tuned model 422 may support. In one or more embodiments, the content customization database 420 may also utilize custom voice data 424 storing data usable by the text-to-speech model 192 to generate custom voice.

Figure 5:
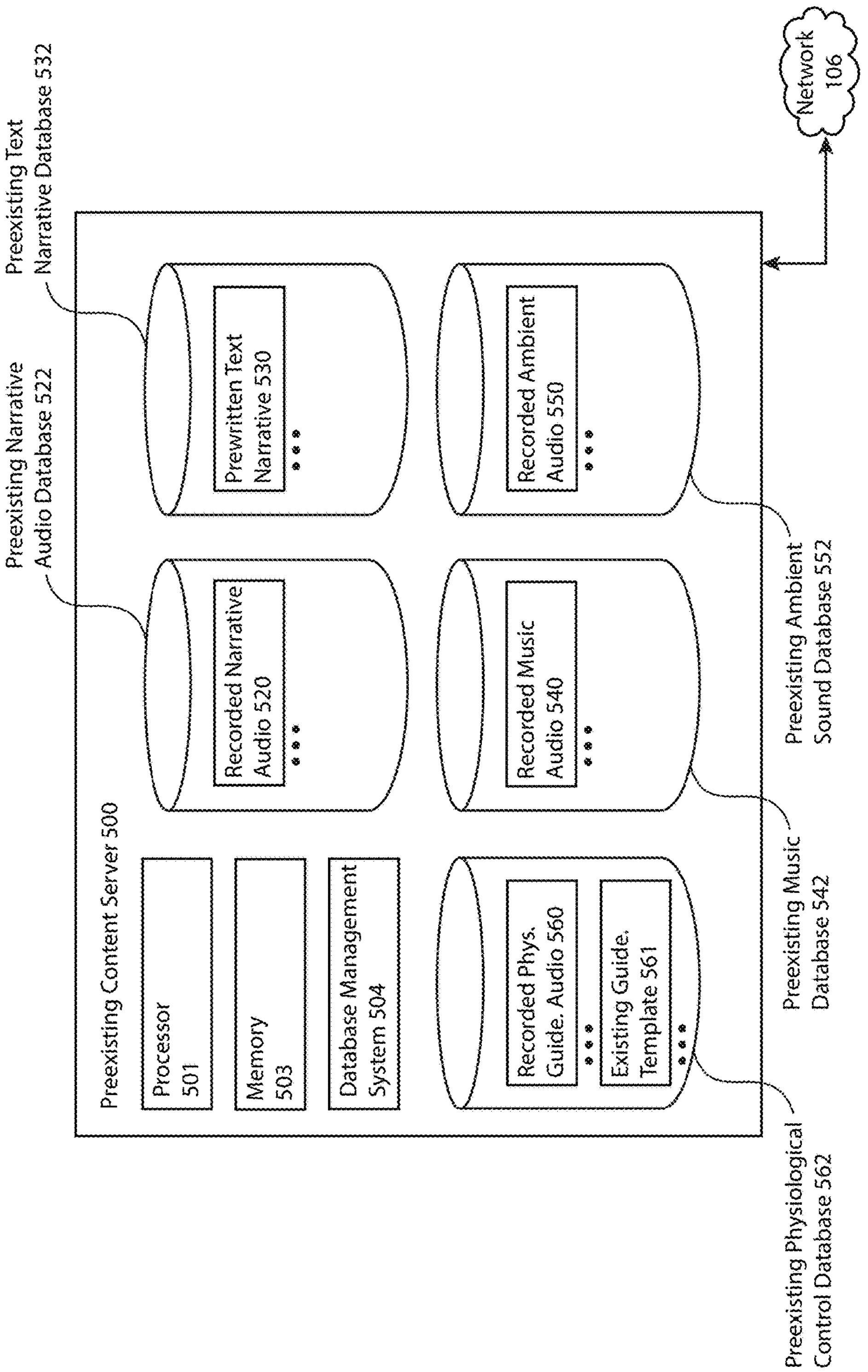
FIG. 5 illustrates a preexisting content server that stores preexisting, prewritten, and/or prerecord data that can be used and evaluated for effectiveness individually, and/or may be used to help train, guide, and/or combine with the outputs of the generative models, according to one or more embodiments.

FIG. 5 illustrates a preexisting content server 500, according to one or more embodiments. The preexisting content server 500 may include a processor 501 that may include one or more computer processors and/or central processing units (CPUs), and a memory 503 which may be a physical non-transient computer readable memory. Although shown as discrete elements in FIG. 5, each of the engines, systems, routines, subroutines, agents, databases, data, and files may be communicatively coupled to one another, through the network, the memory 203, and/or other communication networks and/or communication buses. The preexisting content server 500 may be communicatively coupled to the network 106. The preexisting content server 500 may additionally include a database management system 504, which may be similar to and/or the same type as the database management system 404.

The preexisting content server 500 may be configured to store content that may preexist the request 107 of the user 100, for example live recorded audio (e.g., a music track), previously synthesized audio (e.g., a synthesized voiceover of physiological guidance), and/or other audio files or data renderable as audio files. For example, apart from audio data, the content server 500 may also store data usable to generate audio, for example text that can be turned into audio using text-to-speech systems, and/or descriptions of music or ambiance that can be rendered (e.g., a MIDI file). Similarly, the content server 500 may include physiological guidance templates (e.g. the existing guidance template 561) that can be utilized as a constraint on one or more generative content models 120, or otherwise rendered, for example by associating voice audio ("breath in") with each of one or more cues within the existing guidance template 561.

The preexisting narrative audio database 522 may store one or more instances of the recorded narrative audio 520. The preexisting narrative audio may include a preexisting or synthesized audio file that includes narrative, for example a sleep story, a podcast, a university lecture, etc. The existing text narrative database 532 may store one or more instances of the prewritten narrative text 530. For example, the prewritten narrative text 530 may include a transcript, or otherwise store data defining the sleep story, the podcast, the university lecture, etc. The preexisting music database 542 may include one or more files of recorded music audio 540, for example recorded music tracks as part of a music catalogue or library. For example, the recorded music audio 540 may be drawn from a relatively large, licensed catalogue such as available through Spotify® or Apple Music®, and/or may be a smaller library internally composed, and synthesized and/or performed and recorded music. The preexisting ambient sound database 552 may include recorded ambient audio 550, for example soundscapes including one or more ambient sounds (e.g., nature sounds, city soundscapes, etc.). The preexisting physiological control database 562 may include recorded physiological guidance audio 560 (e.g., breathing exercises spoken by a voice, and/or breathing exercises with auditory cues) and/or an existing guidance template 561 which can be rendered and/or utilized as input to one or more of the generative content models 120.

In one or more embodiments, and although not shown in FIG. 5, it will be recognized that there may be overlap in the content and data stored within the preexisting content server 500. For example, some recorded audio may include both music and ambient sound, or a narrative audio may include periodic music backdrop.

In one or more embodiments, and although not shown in FIG. 5, previously generated instances of the generative sleep content 800 can also be stored in the preexisting content server 500, for example if a particular generative sleep content 800 is determined to be so highly effective as to warrant permanent addition to the available canned responses to the request 107 for sleep assistance audio 102. Previously generated instance of the generative sleep content 800 may also be stored for a period of time and tested for effectiveness, according to one or more embodiments.

Figure 6:
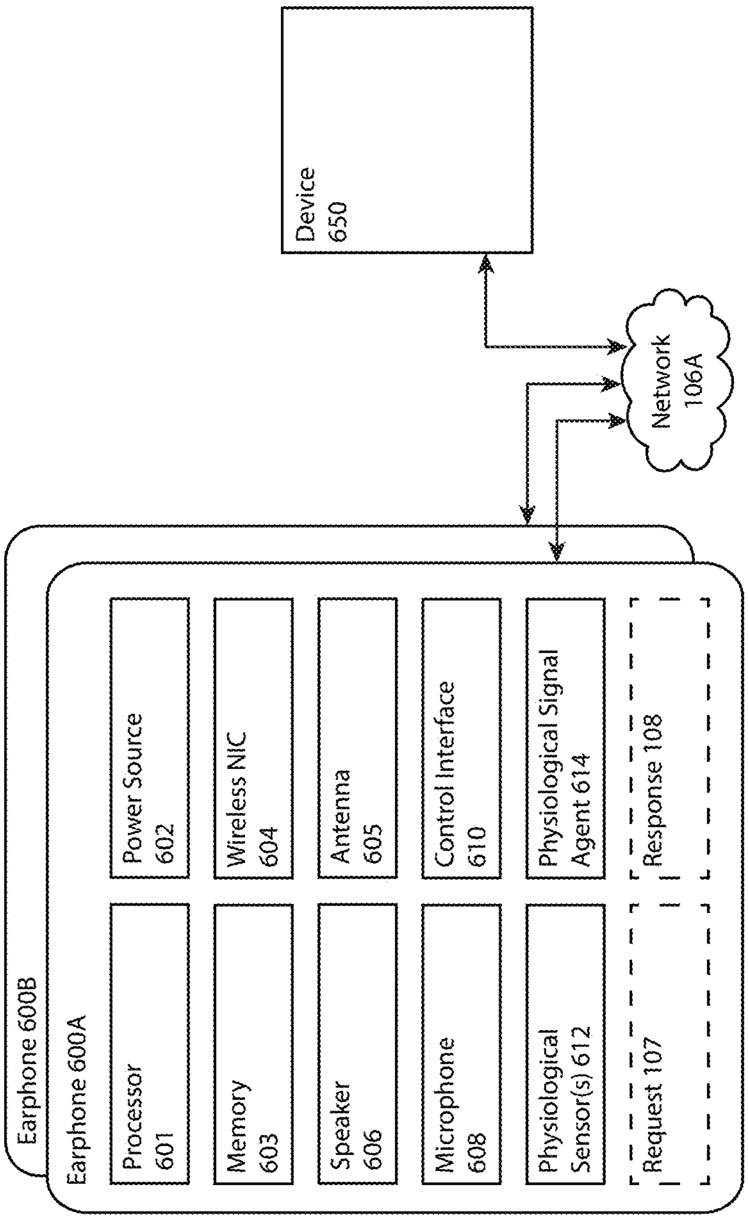
FIG. 6 illustrates a set of earphones, for example as may be implemented as earbuds and an optionally associated device such as a smartphone, that may be used to gather physiological data, initiate generative sleep content requests through a voice interface, receive sleep assistance audio, generate sleep improvement requests, and/or receive and play voiceover audio of sleep improvement interventions 180, according to one or more embodiments.

FIG. 6 illustrates one or a set of earphones 600 of the user 100, according to one or more embodiments. The earphones 600 may be communicatively coupled to the sleep assistance server 200, for example directly through a local network access point (e.g., a WiFi router) and/or though pairing with an additional device 650, such as a smartphone of the user 100 which may be communicatively coupled to the network 106. For example, in one or more embodiments the response 108 including any generative sleep content 800 may be delivered to the device 650 and then further served or streamed to the earphones 600. In one or more preferred embodiments, the earphones 600 may be implemented or as earbuds that fit inside at least the concha of the ear of the user 100. The earphones 600 may include a processor 601 that may include one or more computer processors, central processing units (CPUs), and/or microcontrollers (MCU), and a memory 603 which may be a physical non-transient computer readable memory. Although shown as discrete elements in FIG. 5, each of the engines, systems, routines, subroutines, agents, databases, data, files, and hardware elements (e.g., the speaker 606, the microphone 608) may be communicatively coupled to one another, through the network, the memory 203, and/or other communication networks or buses.

The earphones 600 may include a power source 602 such as a wired connector or, preferably, a rechargeable battery. In one or more embodiments, the earphones 600 may include a wireless network interface controller 604 (e.g., shown as the wireless NIC 604) and an antenna 605 which may be integrated into a form factor of the earphones.

The earphones 600 may include a speaker 606, for example audibly coupled to the ear canal of the user 100 when properly positioned, and/or a microphone 608 for collecting voice of the user 100 and/or implementing the voice interface 104. For example, the microphone 608 may be used to collect commands to control the earphones 600 (e.g., change volume, change audio, etc.) and/or submit the request 107. Additionally, the microphone 608 may be used to gather physiological data 205 based on sound, for example the sound of the user 100 breathing or snoring.

The earphones 600 may include a control interface 610 for controlling one or more functions of the earphones 600, either through interactions with buttons or touch sensors, and/or through the voice interface 104. For example, the control interface 610 may be able to recognize certain commands (e.g., "volume up") in a wide array of voices, languages, dialects, and/or accents without further assistance or support. The control interface 610 may be able to call for recognition of differently framed or formulated requests 107 that may be more easily recognized through a trained artificial neural network with training data comprising user 100 requests for earphone 600 control paired with competent responses (e.g., "please turn this thing down a little bit" paired with a command to decrease volume two "ticks"). The control interface 610 may also be stored on and/or utilized by the device 650, which may enable enhanced processing capability.

In one or more embodiments, the earphone 600 may include one or more physiological sensor(s) 612. The physiological sensor(s) 612 may include, for example, an inertial measurement unit (e.g., an IMU which may include an accelerometer), a thermometer, and/or the microphone 608. The IMU may be able to determine a heartbeat of the user 100, a respiration event of the user 100, and/or macro movements of the user 100 that may be indicative of restlessness, an awake state, and/or a concerted awake state.

In one or more embodiments, the earphones 600 may include a physiological signal agent 614 configured to collect and transmit physiological data from the one or more physiological sensors 612.

The physiological signal agent 614 may include computer readable instructions that when executed gather physiological data 205 of the user 100 from a sensor (e.g., a physiological sensor 612) of an earbud (e.g., an instance of the earphone 600) worn by the user 100. As previously shown and described, this data can be paired with sleep improvement interventions 180 and/or sleep assistance audio 102 to help determine effectiveness of either in promoting quality sleep. For example, the physiological data 205 may be gathered while a sleep improvement intervention 180 is being implemented and/or while the generative sleep content 800 is played as the sleep assistance audio 102 on a speaker 606 of the earbud.

FIG. 7 illustrates an example generative prompt extraction and formulation process, according to one or more embodiments. The user 100 may submit, for example through the voice interface 104, the request 107 which may include an audio generation request 701 for creation of generative audio content 800 and/or generative audio data 801. The audio generation request 701 may be parsed (e.g., though the request agent 210) to fractionate one or more prompts 702. First, the audio of the request 107 may be submitted to a speech-to-text routine 218 to transcribe the request 107, as may be executed on the sleep assistance server 200 or another location.

Each word that is specified or determined to be related to categories of generation, e.g., narrative, physiological guidance, music, and ambient sound may be extracted and collected. In one or more embodiments, the exact words of the user 100, as transcribed, may be used in formulating the prompts 702. In one or more other embodiments, additional acronyms or term mappings may be utilized. In one or more embodiments, the parsing may be effected by one or more artificial neural networks trained to recognize (i) the categories of request, and/or (ii) competent prompts 702 associated with the request text within the audio generation request 701. Some modifiers may be applied to multiple generative categories, for example "a calm story about a person who finds a castle with realistic sound" may utilize the word "calm" as both a narrative prompt 730 and a music prompt 740, according to one or more embodiments.

The narrative prompt 730 may include text prompts to act as narrative portions of the inputs prompts 127 responsive to the audio generation request 701. For example, the narrative prompt 730 may include data about a subject, setting, characters, hero, plot points, story elements (e.g., threshold, nadir, etc.), analogous stories to be modeled after, and/or other aspects of the story. The narrative modifier 732 may be a description of one or more qualities of the narrative, for example a narrative style description 734 and/or a narrative genre description 736, either of which may be explicitly identified and extracted or may be recognized and imputed (e.g., "a story about a man with no name who comes into a town and succeeds at saving the town" may be associated with a "western"). The narrative modifier 732 may also include a general quality of the narrative to be generated, for example "calm", "thoughtful," "vivid," etc. Negative items within the narrative prompt 730 may be referred to herein as a narrative filter.

The music prompt 740 may include text prompts to act as inputs prompts 127 responsive to any music portion of the audio generation request 701. For example, the music prompt 740 may specify types of instruments to be included or excluded (e.g., stringed, brass), an instrument to be included or excluded, an emotion of music to be excluded (e.g., such as dance music or sorrowful music), a user of music (e.g., ballet music), analogous music to be modeled after, etc. A music modifier 742 may be extracted from (or recognized from and imputed to) the music prompt 740, for example a description of one or more qualities of the music, including for example a music style description 744 and/or a music genre description 746. The music genre description 746 may be explicitly identified and extracted (e.g., the user 100 asking for "blue grass" or "American folk"), or may be recognized (e.g., "music was a bass, saxophone and keyboard" as likely associated with "jazz"). The music style description 744 may include a quality such as calm, allegro, complex, simple, major, minor, orchestral, string quartet, synthesized, etc. Negative items within the music prompt 740 may be referred to herein as a music filter. As further shown and described in conjunction with the embodiment of FIG. 3, where music is to be generated with limited or no explicit prompt form the user 100, a text-music relation model 352 may be utilized to generate a music prompt 740, for example by relating narrative prompts 730 to one or more musical elements, one or more music style descriptions 744, and/or one or more music genre descriptions 746.

Similarly, the ambient sound prompt 750 may include text prompts to act as inputs prompts 127 responsive to any ambient sound portion of the audio generation request 701. The ambient sound prompt 750 may include specifying a type of sound to be included or excluded (e.g., nature sounds, running water, man-made sounds, etc.), a sub-type (e.g., birds, forest sounds), analogous music to be modeled after, etc. An ambient modifier 752 may be extracted from or imputed to the ambient sound prompt 750, for example a description of one or more qualities of the ambient sound. Qualities of the ambient sound to be generated may include an ambient style description 754 which may be explicitly identified and extracted, or may be recognized (e.g., "crickets", "frogs", and "water" may be recognized as a "wetland" soundscape). Similarly to narrative and music filters, negative items within the ambient sound prompt 750 may be referred to as an ambient filter.

In one or more embodiments, the physiological guidance prompt 760 may include text prompts to act as inputs prompts 127 responsive to any physiological guidance portion of the audio generation request 701. For example, the physiological guidance prompt 760 may specify a type of physiological control (e.g., respiration, heartbeat, cognitive processing load, iso state) which may be optionally extracted as the physiological guidance type 764. The physiological guidance prompt 760 may also specify, for example, a method of physiological control (e.g., explicit voiceover instruction, integrated into music, integrated into ambient, haptic control such as vibration from a smartphone or smartwatch, etc.), and/or a quality of the physiological control (e.g., transitioning, fading out, etc.).

In one or more embodiments, any of the words or phrases of the prompts 702 may be stored and tracked for sleep effectiveness. In one or more embodiments, such words or phrases may include any of the explicitly extracted (or recognized and imputed) modifiers, styles, generates, and/or types thereof.

In one or more embodiments, a session RAG data 124 may be initiated and the prompts 702 may be initially written to the session RAG data 124. The prompts 702 may be separated by prompt type (e.g., narrative, music, ambient, physiological guidance) and as may be specified as originating from the request 107.

In one or more embodiments, a prompt compare and filter module 125 (which may execute on the generative content server 300 or another location) may compare one or more of the prompt 702 within the session RAG data 124 and either maintain, delete, supplement, and/or replace a portion of the prompt 702 depending on priority of the source. In one or more embodiments, the prompt compare and filter module 125 may enable an automated prompt engineering capable of developing a more well developed set of input prompts 127 that have a higher probability of producing competent results from the generative content models 120. This approach may be useful in managing the wide variety of potential prompts 702 that may result from a diverse population of users 100. As just one of many examples, it may be determined that certain term usable as a prompt 702 may have a specific usage within the context of sleep; such association may not help in generating competent results due to other associations with the term within the base model of an LLM. Such term can be eliminated, replaced with synonyms, and/or definitions pulled into the context window 126 and assigned substantial consideration weight utilizing one or more variables of the generative model 120.

In one or more embodiments, a general sleep model augment data 122 may be queried and relevant portions extracted for comparison and potential inclusion in the session RAG data 124. First, for example, only relevant generative types may be assessed within the general sleep model augment data (e.g., narrative and ambient). In one or more embodiments, sub-sections of the general sleep model augment data 122 then may be referenced to reinforce style, genre, and/or type descriptions. For example, where the user 100 included an explicit request within the music prompt 740 for "orchestral," the general sleep model augment data 122 may include a set of associated words and phrases to increase the probability that orchestral music will be generated. When loaded into the session RAG data 124, mutually exclusive terms (e.g., antonyms) may be excluded (with priority optionally given to the prompts 702 provided by the user 100), a limited number of synonyms may be permitted (e.g., 2, 5, 10), and words or phrases that are neither opposed or aligned in meaning may be included as new information likely leading to improved results from the generative content models 120. Any newly added terms may be additionally tested for effectiveness, for example as shown and described herein.

The prompt compare and filter module 125 may optionally query the user specific augment data 123 and relevant portions extracted for comparison and potential inclusion in the session RAG data 124. The process may be similar to that of the general sleep model augment data 122, but may, in one or more embodiments, take higher priority than the general sleep model augment data 122. Effectiveness data for the user 100 may also be inspected, including where such data is stored in or referenced by the user specific augment data 123. For example, certain words or phrases may be determined to be generally ineffective (e.g., below a threshold value) and therefore may be removed from the session RAG data 124. As just one example, where the term "instrument solo" is generally found to be ineffective, for instance because it catches the attention of the user 100 just as the user 100 is trying to fall asleep (as may be determined by the sleep session data 414), then the term "instrument solo" may be added as a negative prompt and/or filter. Continuing the example, if "instrument solo" had been added by the general sleep model augment data 122 (for example, as a common element associated with jazz), the term may be deleted.

The session RAG data 124, including all of the prompts 702 either from the user request 107 or else ware and as may have been re-engineered and/or re-formulated, may then be loaded as the inputs prompts 127 for input nodes 128. The input nodes 128 may include those for each of the relevant generative content models 120 (e.g., the text generation model 130, the music generation model 140, the ambient sound generation model 150, and the physiological guidance model 160), including for example use of a context window 126 for each of the relevant generative content models 120. Each of the relevant generative content models 120 may then proceed to process the inputs through one or more trained an artificial neural network. Alternatively, or in addition, as shown through the 'circle A', 'circle B', and 'circle C' returning from FIG. 8, any output failing quality control or other integration checks may have prompts re-engineered and/or may be resubmitted to the input nodes 128. The output of the generative content models 120 are shown and described in conjunction with the embodiment of FIG. 8.

FIG. 8 illustrates a generative sleep content creation system 890, for example illustrating the outputs of the generative content models 120 and/or synthesis into a generative sleep content 800. In one or more embodiments, the generative content models 120 may produce a set of outputs (e.g., the outputs 810), which may be further quality controlled, filtered, rendered, adjusted, and/or otherwise tested for compatibility, and then may be integrated into the sleep assistance audio 102. In one or more embodiments, each of the outputs 810A may be raw data outputs collected from the generative content models 120, according to one or more embodiments. For example, where the generative content models 120 include one or more artificial neural networks, the output may be collected from the output nodes 129 of one or more artificial neural networks of each of the generative content models 120. The outputs 810A may include a physiological guidance template 860A, a text data 830A (e.g., of a narrative text), a music audio data 840A, a music composition data 842A (e.g., that can be rendered into music audio), and/or an ambient composition data 852A (e.g., that can be rendered ambient audio).

The outputs 810A may undergo one or more quality control routines 812. For example, a quality control routine 812 may check for general coherency of the outputs 810, including in time (or estimated rendering time) synchronization. The quality control routine 812 may include checks for profanity, blasphemy, and/or indecency. Alternatively, or in addition, the quality control routine 812 may determine adherence to a physiological guidance template in such case that physiological guidance is incorporated into any of the other types of audio data (e.g., narrative, music, or ambient). In one or more embodiments, quality control routine 812 may include submitting one or more of the outputs 810A to an artificial neural network trained to recognized defects, for example in sentence structure, story structure, music structure, etc. In one or more embodiment, the quality control routine 812 may re-submit the input prompts 127 to re-generate one or more outputs 810A not initially meeting quality control, as shown through the 'circle A' association to the embodiment of FIG. 7.

In one or more embodiments, a filter 814 may be applied to one or more of the outputs 810A. For example, audio filters may be utilized to ensure that certain frequencies not conducive of restfulness or sleep may be removed from the outputs 810A. In one or more embodiments, the text data 830A may be rendered into speech through the text-to-speech model 192, any music composition data 842A may be rendered by the music rendering routine 816, and/or any ambient composition data 852A may be rendered by the ambient sound rendering routine 818. Any sound renderings be additionally quality controlled at the time of generation.

The outputs 810B may include a set of quality-controlled outputs, including the narrative audio data 832B, the music audio data 840B, the ambient audio data 850B, and/or physiological guidance template 862B (if not otherwise incorporated into one of the other sets of audio data).

A compatibility evaluation engine 822 may be configured to check audio integration compatibility of one or more of the outputs 810B. In one or more embodiments, the compatibility evaluation engine 822 may submit the one or more outputs 810B to a compatibility evaluation model 824 which may include an artificial neural network trained to recognize and/or align audio data. In one or more embodiments, an adjustment routine 826 may be configured to adjust existing audio to improve compatibility and/or alignment, for example through audio waveform transformation and/or audio files. As just one example, the narrative audio data 832B in one or more portions may be transformed such that the narrative audio data 832B overlays onto the music audio data 840B, with any resulting changes in voice tone due to such transformation (e.g., a higher tone due to time compression of the audio) counteracted through additional transformation of voice frequencies. If multiple attempted adjustments and/or compatibility evaluations fail, one or more of the outputs 810B may be resubmitted along path 'circle B' to be re-prompted, have one or more generative parameters adjusted, and/or may be resubmitted to the input nodes 128 of the relevant generative content model 120.

Following a passing compatibility evaluation, the outputs 810C may be generated. In one or more embodiments, the content integration engine 380 may then integrate the two or more outputs 810C. In one or more embodiments, the integration may include an overlay of each of the outputs 810C. In one or more embodiments, the integrating may include adjusting levels of audio, for example amplitude and any interfering tones within the outputs 810C. In one or more embodiments, the content integration engine 380 may submit the outputs 810C to an integration model 382 that may include an artificial neural network trained to generate a single audio file from two or more audio files through training data comprising (i) separate audio samples and (ii) competent synthesis and/or integration of the two separate audio samples into a single audio sample.

Following integration into a single audio data or synchronization of multiple audio data to be played concurrently, the quality control routine 829 may review the tentative output for quality, for example integration artifacts, defects, time sequence mismatch, and/or other audio quality issues. The quality control routine 829 may also perform final checks to ensure physiological guidance cues are properly included and discernable. If one or more aspects fail quality control, one or more of the outputs 810 may be resubmitted for re-prompting, prompt engineering, and/or to model parameter adjustment along path 'circle C'. If passing quality control, the generative sleep content 800 may be complete, and may utilized as, or included within, the sleep assistance audio 102 as delivered to the user 100.

Although FIG. 7 and FIG. 8 illustrate parallelized creation of the generative sleep content 800, it will be recognized that serial or partial parallel creation can be implemented. For example, the text data 830A may be first generated and then, based on various events or settings of the story, matching music or ambient sound generated along with any requests or constraints of the user 100 (e.g., "don't include insect noises").

Figure 9:
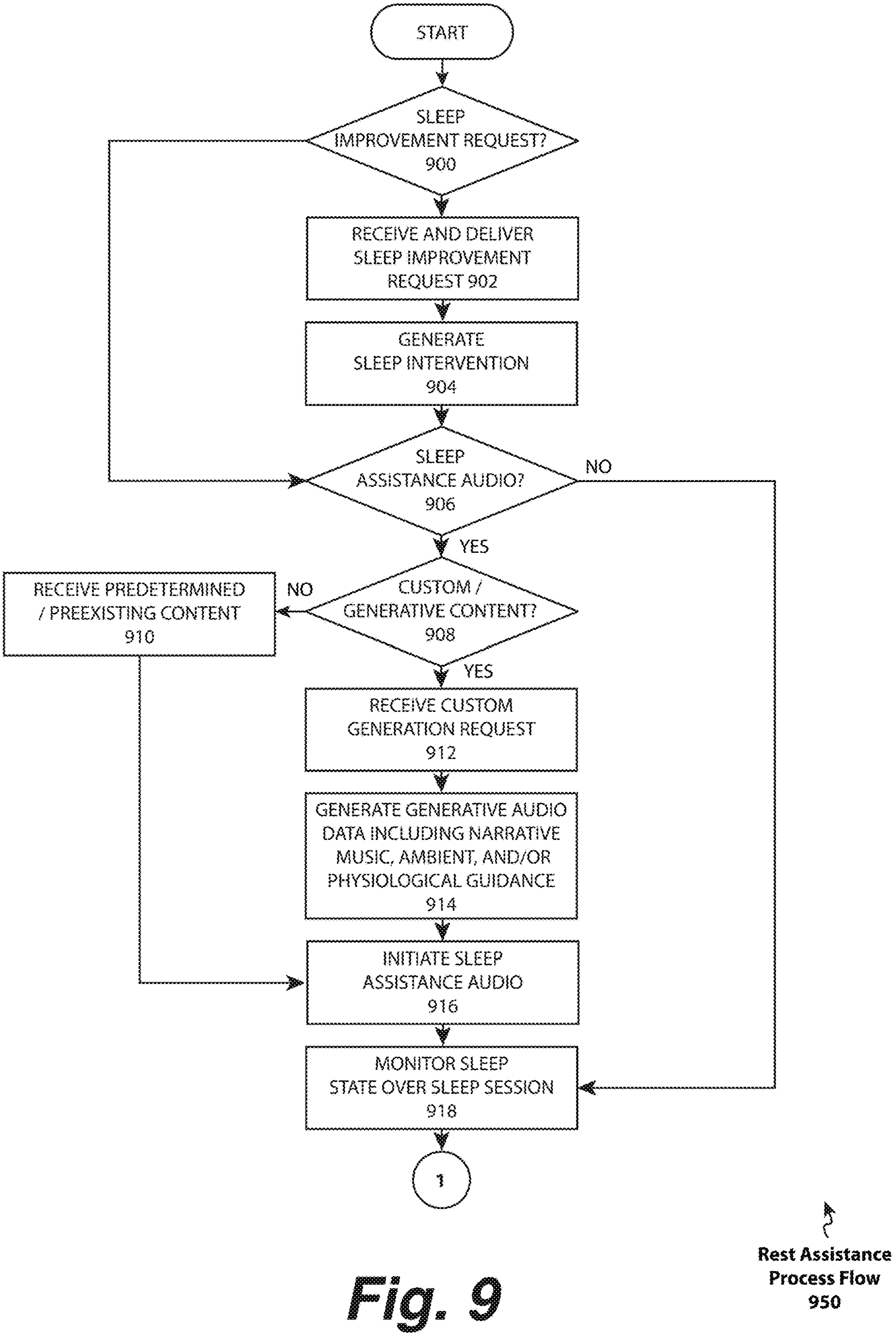
FIG. 9 illustrates a rest assistance process flow, according to one or more embodiments.

FIG. 9 illustrates a reset assistance process flow 950, according to one or more embodiments. Operation 900 determines whether there is a sleep improvement request 170 for the user 100. The sleep improvement request 170 may include a request by the user 100, and/or by an automatic device or system assessing sleep data or sleep metrics of the user 100. The request 107 may include a request for improved sleep based on perceived or felt need for sleep improvement and/or data-driven identification of sleep deficiencies (and/or opportunities for sleep improvement). Operation 900 may be initiated automatically (e.g., the user 100 placing earbuds into their ears, indicating they are about to fall asleep), automatically with consent of the user 100 (e.g., detection the user 100 is initiating a sleep session followed by a query as to whether the user 100 would like to know about a pending potential sleep improvement opportunity and/or intervention), and/or manually (e.g., the user 100 initiating a request 107 including that the user 100 would like to improve their sleep. If no sleep improvement request is to be resolved, operation 900 may proceed to operation 906. Where a sleep improvement request 170 is to be resolved, operation 900 may proceed to operation 902.

Operation 902 may receive a sleep improvement request 170. The sleep improvement request 170 may be included within the request 107 submitted by the user 100, for example through an app (e.g., a smartphone app), and/or through a voice interface 104 as may be implemented by a microphone and speaker within the earphones 600. The request 107 may be parsed to identify and extract the sleep improvement request 170 and components thereof. In one or more embodiments, additional context may be gathered external to the sleep improvement request 170 may be gathered, for example where the user 100 utilizes a keyword such as "insomnia", "worried about . . . " or "back pain."

Operation 904 may then generate and deliver a sleep improvement intervention 180 for responsive to the sleep improvement request 170. The sleep improvement intervention 180 may be stored and transmitted as the sleep improvement intervention 180. In one or more embodiments, the sleep improvement intervention 180 may include data specifying a set of guidelines, rules, steps, factors, and/or processes for the user 100 to follow or implement before, during, or after sleep. In one or more embodiments, and as shown and described throughout the present embodiments, the sleep improvement intervention 180 may be generated as the output of an artificial neural network. The ANN may be trained on, or supplemented with (e.g., through retrieval augmented generation or other methods) competent sleep query data and appropriate paired interventions, as may be developed through sleep experts and/or future system feedback based on effectiveness. Operation 904 may then proceed to operation 906.

Operation 906 may determine whether a user 100 will receive sleep assistance audio 102, for example preexisting audio (e.g., a music track) and/or generative audio (e.g., generated on demand, in real time, and/or in advance for the particular user 100 and/or subpopulation of users 100). In one or more embodiments, the generative audio may be generative sleep content 800 that may include newly generated narrative text (e.g., a "sleep story"), music, ambient sound, and/or explicit or incorporated physiological guidance such as breathing exercises. The sleep assistance audio 102 may also include a mix of both preexisting content 510 and generative content that may be integrated and/or combined. Operation 906 may be initiated automatically (e.g., the user 100 placing earbuds into their ears, indicating they are about to fall asleep), automatically with consent of the user 100 (e.g., detection the user 100 is initiating a sleep session followed by a confirmation query to the user 100, and/or manually (e.g., the user 100 initiating a request 107 requesting the sleep assistance audio 102). If sleep assistance audio 102 does not need to be utilized, operation 906 may advance to operation 918, as further described below. If sleep assistance audio 102 is to be generated, operation 906 may proceed to operation 908.

Operation 908 may determine if custom and/or generative audio is to be generated, in which case operation 908 may proceed to operation 912. If no custom and/or generative audio is to be created, operation 908 may proceed to operation 910, which may receive and/or select a predetermined and/or preexisting content. For example, an audio track may be selected, a set of breathing exercises narrated or recorded as audio, a breathing exercise template selected (e.g., an example of the existing guidance template 561), etc. The selection may be directly responsive to the request 107 of the user 100. For example, the user 100 may have requested a particular audio track, a symphony which may have been performed by two or more orchestras which can be automatically selected from, and/or a type of soundscape or primary element thereof, such as "crashing waves".

Operation 912 may receive a custom generation request from the user 100. The custom generation request may include information from the user 100 describing what the user 100 wishes to be generated for use in initiating or maintaining sleep. As just one example, the user 100 may describe the type of narrative, music, ambient sound, and/or physiological guidance that should be generated to assist in initiating or maintaining sleep. The description may have been selected by the user 100 through an app or other software application (e.g., from a preexisting menu of options, genres, styles, elements, or components), may include freeform text entered by the user 100, and/or may include text transcribed from speech of the user 100 collected through a speaking, for example via the voice interface 104. The custom generation request may be parsed, preformatted, or structured (e.g., through a selection menu) such that one or more prompts (e.g., the prompts 702) may be separated into discrete or overlapping categories of generation (e.g., narrative, music, ambient, and/or physiological guidance).

Operation 914 may generate the generative audio data 801 including narrative, music, ambient, and/or physiological guidance. Generation may occur through one or more generative processes, including for example, and as shown and described throughout the present embodiments, by utilizing one or more generative content models 120 that may include artificial neural networks. For example, one or the ANNs may be trained with training data to generate: (i) narrative text which can be rendered into audio, (ii) narrative audio, (iii) physiological guidance templates, (iv) physiological guidance audio, (v) a musical composition description that can be rendered into music audio, (vi) music audio, (vii) an ambient composition description that can be rendered into ambient audio, and/or (viii) ambient audio. In one or more embodiments, the physiological guidance may be included within the narrative structure or audio, the music, structure or audio, and/or the ambient structure or audio. The resulting generative audio data 801 may be a synthesis and/or integration of the generative outputs 810. In one or more other embodiments, it will be recognized that one, two, or three instances of the generative content model 120 may be trained to generate outputs that simultaneously include two or more of the narrative text, music, ambient sound, and/or physiological guidance, according to one or more embodiments.

Operation 916 may initiate the sleep assistance audio 102 for the user 100. For example, the sleep assistance audio 102 may begin being played on a speaker of a device 650 of the user 100, such as a smartphone, earphones (e.g., the earphones 600), and/or earbuds. The initiation of the sleep assistance audio 102 may occur automatically (e.g., upon the user 100 inserting earbuds), automatically in response to the request 107 (e.g., the instruction to initiate the playback may be made as the response 108 following the request 107), and/or at the manual request of the user 100, for example through the voice interface 104. The sleep assistance audio 102 may be stored as a file on the device that has the speaker (e.g., the earphones 600), or another device supporting the device with the speaker (e.g., the device 650 such as a smartphone).

Operation 918 may then monitor the sleep state of the user 100 over a sleep session. Monitoring may include determining quality of sleep over the time period of the sleep session, including one or more sleep quality key performance indicators as known in the art of sleep health and/or the art of sleep cycle management. In one or more embodiments, the monitoring may include monitoring for cognitive state (e.g., whether the user 100 is awake, asleep, in a deep sleep, in a REM or Non-REM sleep, etc.). For example, following termination of a sleep session, periods of cognitive state associated with time-series data may be used to calculate sleep metrics, such as sleep onset latency, number of REM cycles, number of interstitial awake periods. An interstitial awake period may include the user 100 waking up to use the bathroom, waking up due to a loud noise, waking up due to general restlessness, etc.). Cognitive state may be determined from physiological data 205 sensed from the user 100 using one or more devices (e.g., the earphones 600 and/or the device 650), and/or direct feedback from the user 100 (e.g., a faint audible chime to which the user 100 may grunt or respond if they are still awake).

The sleep session may have been initiated automatically upon detecting that the user 100 is likely attempted to sleep (e.g., placing earbuds in their ear), initiated automatically following delivery of sleep assistance audio 102, initiated automatically in response to a query to the user 100 through the voice interface 104 (e.g., “are you ready to start your bedtime routine?”) and/or initiated manually (e.g., at the request of the user 100). Initiation of the sleep session may initiate and then store a dataset or file for storing data associated with monitoring the sleep state, for example the sleep session data 414, as may be shown and described throughout the present embodiments. Operation 918 may then proceed along path ‘Circle 1’ to the operation 1000 in the embodiment of FIG. 10.

Figure 10:
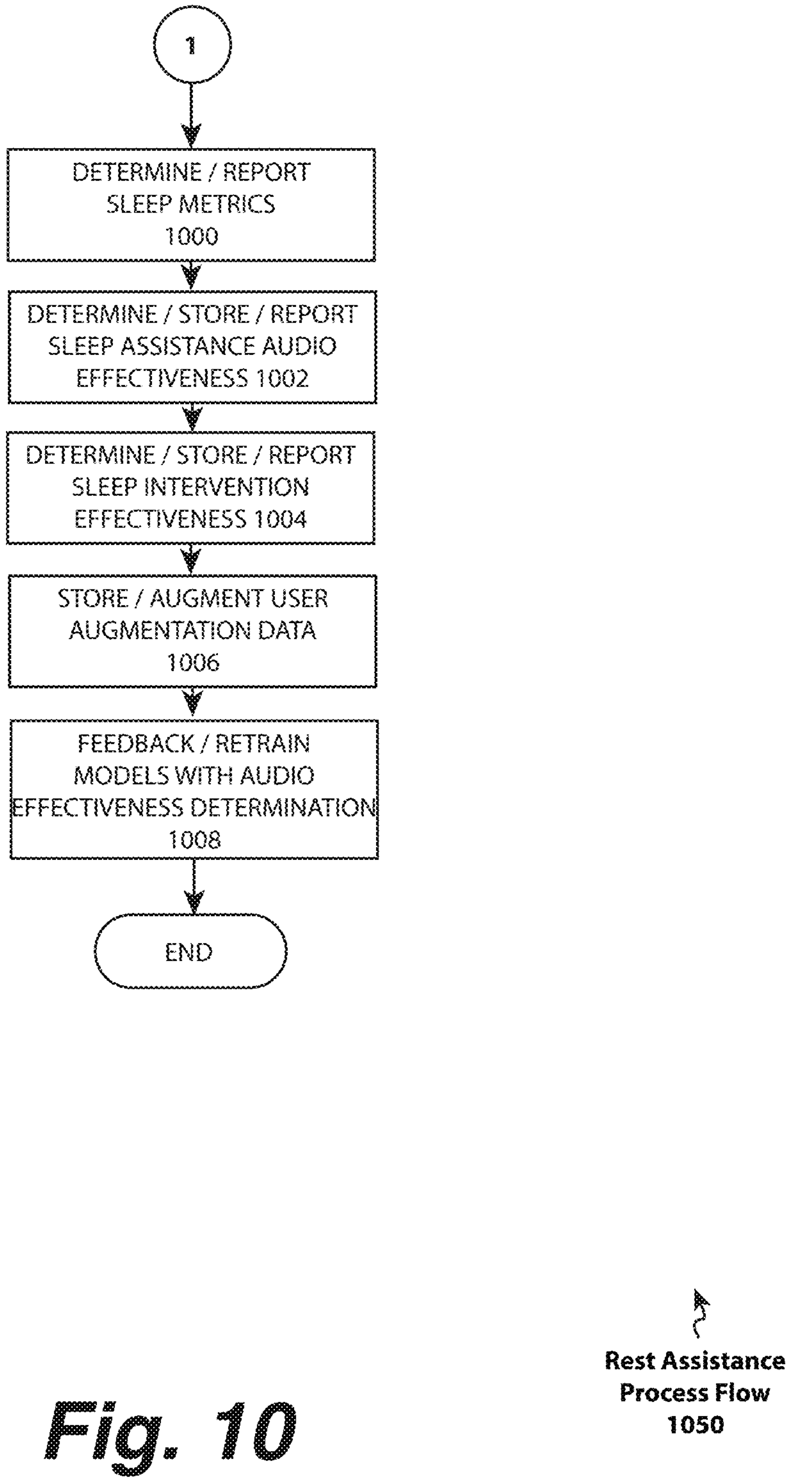
FIG. 10 illustrates a continuation of the rest assistance process flow of FIG. 9, according to one or more embodiments.

FIG. 10 illustrates a rest assistance process flow 1050, according to one or more embodiments. Operation 1000 may determine and/or report sleep metrics to the user 100. For example, the user 100 may receive an audio report as speech over the voice interface 104 that may inform the user 100 as to their sleep onset latency, improvement in sleep onset latency relative to a previous session, an amount of restlessness, a length of time of period of restlessness, a number of time the user 100 got out of bed or sat up, a percentage of environmental sounds the user 100 slept through, a hybrid quality score, etc.

Operation 1002 may determine and/or report sleep assistance audio 102 effectiveness. In one or more embodiments, for those portions of the sleep session in which the user 100 utilized the sleep assistance audio 102 (as may be tracked in the sleep session data 414), the positive or negative effect of the sleep assistance audio 102 may be determined when compared with the sleep metrics and/or cognitive state of the user 100 over such time periods. Additional factors may be considered in evaluating effectiveness, for example whether environmental disturbances occurred, whether the user 100 reported they were in an anxious state, whether the user 100 had another temporally proximate sleep session (e.g., a late nap during the day), etc. Sleep assistance audio 102 may be utilized two or more times to increase the probability and statistical reliability of effectiveness determinations. In addition, the user 100 may be asked to provide feedback as to whether the user 100 thought or believed that the sleep assistance audio 102 was useful, whether in general or as to specific aspects or with respect to certain metrics of sleep (e.g., “did the sleep story help you fall asleep faster?”).

Operation 1004 may determine and/or report effectiveness of the sleep improvement intervention 180 (e.g., delivered via the sleep improvement intervention 180). Sleep assistance audio 102 may be used for evaluating sleep improvement interventions. For portions of the sleep session in which the user 100 implemented the sleep intervention, the effect of the sleep assistance audio 102 may be determined when compared with the sleep metrics data 418 and/or cognitive state of the user 100 over such time periods. For example, where the user 100 exercised vigorously five hours before sleep, compliance with a binary intervention step may have been met. In another example, where the user 100 read a book within 30 minutes of sleeping, an amount of time may be logged (the user 100 may be asked to provide over the voice interface 104 when they started reading and stopped reading). As yet another example, where the user 100 implemented a reduction in environmental light within a sleep environment 101, the entire time period of the sleep session after the user 100 turned off the lights may be specified. Additional factors may be similarly considered in generating effectiveness, for example whether environmental disturbances occurred, whether the user 100 reported they were in an anxious state, whether the user 100 reported they are taking medication that may interfere with or induce sleep, etc. Sleep assistance audio 102 may be utilized or implemented multiple times to increase statistical reliability. In addition, the user 100 may be asked to provide direct feedback, whether general or related to specific aspects of a sleep improvement intervention 180.

In one or more embodiments, following the determination of effectiveness of any sleep assistance audio 102 and any sleep improvement intervention 180, operation 1006 may store the effectiveness data for later use or reference (e.g., as the sleep audio effectiveness data 421 and/or the intervention effectiveness data 423, respectively). Operation 1006 may also update one or more augmentation files (E.g., the user specific augment data 123) usable for adjusting requests, generative content, and interventions in future requests 107, for example future sleep improvement requests 170 and/or generative sleep content requests 700.

Operation 1008 may then feedback the results of the effectiveness determination to improve future requests 107 for sleep assistance audio 102 and/or sleep improvement interventions 180. For example, ratings, values, scores, and/or descriptions of effectiveness may be stored for further evaluation. In one or more embodiments, an intervention determined to be effective in one user 100 may be put into testing for another user 100, implementation for a sub-population of users 100, and/or put into production use for the entire population of user 100. In one or more embodiments, the feedback may be implemented in whole or in part by storing effectiveness data or references thereto within the general sleep model augment data 122 and/or the user specific augment data 123. In one or more other embodiments, one or more sleep improvement interventions 180 and/or one or more items or elements of sleep assistance audio 102 may be utilized to retrain one or more AI models. For example, one or more generative content models 120 and/or the sleep assistance model 115 may be fine-tuned and/or further trained utilizing paired or associated data that can be utilized to adjust node-weights and other adjustable parameters of one or more artificial neural networks. Such paired or associated data may include, for example: (i) request for improvement/intervention resulting in metric improvement, (ii) intervention/metric improvement, (iii) audio/resulting metric improvement, (vi) request/audio resulting in metric improvement, and/or (v) many other combinations as will be recognized to one skilled in the art. Operation 1008 may then terminate, or may return to operation 900, for example upon initiation of the next sleep session of the user 100.

Although "sleep assistance" is described herein, in one or more embodiments it will be recognized that assistance for general rest and relaxation is also possible. For example, the objective of the user 100 may be to engage in physiological control for purposes of meditation, managing anxiety, calming down, and/or for other purposes other than sleep.

Figure 11:
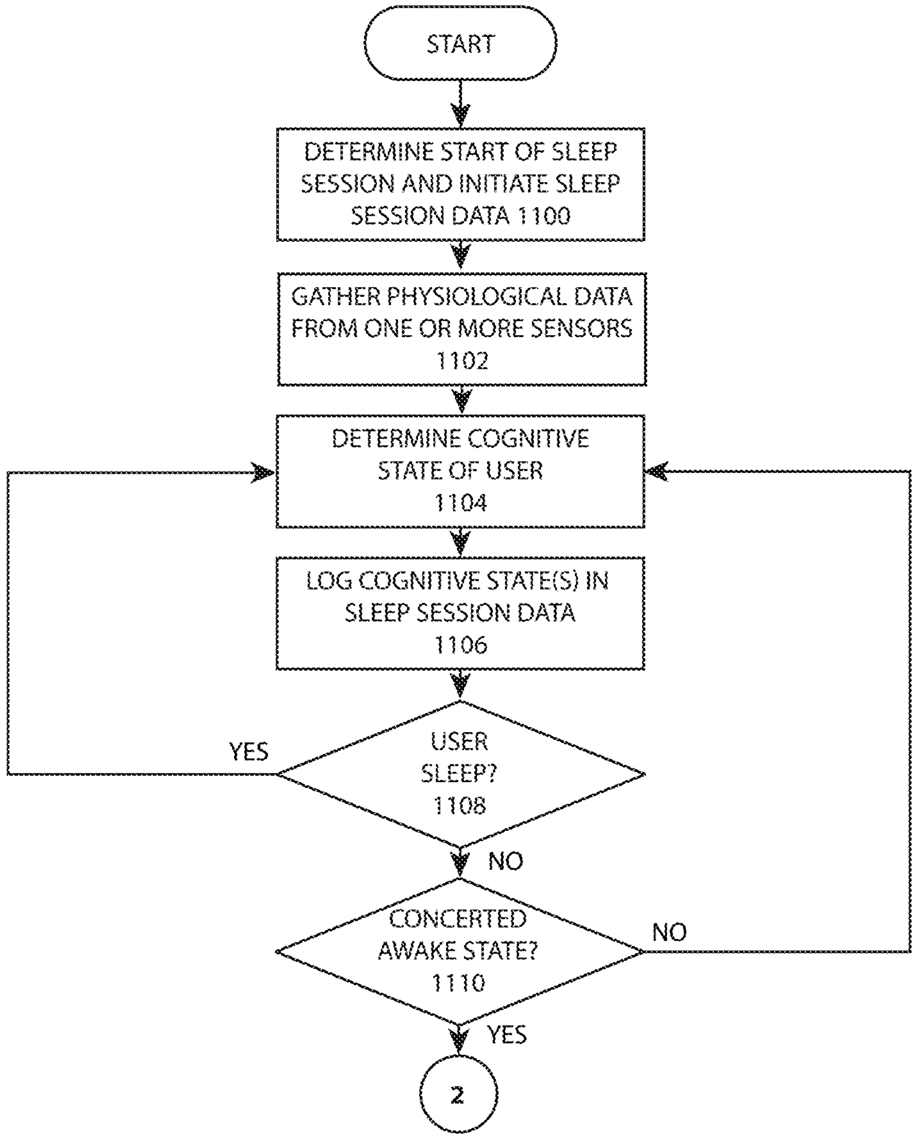
FIG. 11 illustrates a sleep session analysis process flow, according to one or more embodiments.

FIG. 11 illustrates a sleep session analysis process flow 1150, according to one or more embodiments. Operation 1100 determines a start of a sleep session and initiates a sleep session data 414. For example, a ruleset may be developed to determine conditions upon which the sleep session initiates, such as the user 100 lying relatively still and having their earbuds installed, as may be determined from an IMU and infrared touch proximity sensors, respectively. The sleep session data 414 may be stored in association with the user profile 410 of the user 100.

Operation 1102 may gather physiological data 205 from one or more sensors. The sensors may be from various devices within the sleep environment of the user 100, including for example wearable devices (e.g., a smartwatch, a smart ring, a medical device outputting sensor data), a smartphone (e.g., providing a microphone and/or an IMU which may be useful if placed on a bed to determine if the user 100 is moving), a smart alarm clock or bedside unit, and/or a base station with a microphone (e.g., for charging earbuds).

Operation 1104 may determine a cognitive state of the user 100 from the physiological data 205. As known in the art, the physiological data 205 may be utilized to determine physiological events, such as heart beats, respiration events (including breathing in, breathing out, and between periods at the "top" and "bottom of breaths), micro movements (e.g., vibration from snoring), and/or macro movements (e.g., the user 100 rolling over or changing position). The physiological events, when time-sequenced, may be further analyzed to result in physiological features such as respiration rate, respiration rate variability, heartrate, heartrate variability, and periods of physical discomfort. The physiological features may be further analyzed, as known in the art, to determine cognitive state, including for example an awake state, a pre-sleep state, an asleep state, a REM state, and/or a NREM state.

Operation 1106 logs the cognitive state, such as the sleep state, in the sleep session data 414. For example, the cognitive state may be identified with a cognitive state ID 415 recorded in the sleep session data 414 along with a timestamp of the cognitive state. Operation 1108 determines if the user 100 has achieved a cognitive state that includes a sleep state, for example from analysis of the physiological features. As just one example known in the art, the respiration rate of the user 100 may be slowly decreasing in the pre-sleep state until, upon entering the sleep state, there may be a sudden increase in respiration rate and/or stabilization of respiration rate variability. If the user 100 is determined to be asleep, operation 1108 returns to operation 1104 for continual determination of cognitive state. If the user 100 is not determined to be in the sleep state, operation 1108 may proceed to operation 1110 which may determine if the user 100 is in a concerted awake state. For example, a user 100 may often wake up due to a loud environmental sound or some other momentary disturbance. The user 100 may also need to get up to go to the bathroom, take medication, or tend to a child. Short periods of wakefulness in which the user 100 then goes back to sleep (or attempts to sleep) may still be considered as, and logged as, occurring within the same sleep session, according to one or more embodiments. For example, where the IMU of a wearable device and/or earphones 600 determine that the user 100 engaged in macro movement (e.g., sitting up and walking for 5 minuets but then laid back down), no concerted awake state may be determined and data on the same sleep session may continue to be gathered. Conversely, where continuous, patterned, or relatively intense movement is sensed, the sleep session may be terminated and the sleep session data 414 reduced to only include activity up until the macro movement was initially sensed.

If the user 100 is not determined to be in a concerted awake state, operation 1110 may return to operation 1104. If the user 100 is determined to be in a concerted awake state, operation 1110 may terminate, or may proceed along path 'Circle 2' to the process flow of FIG. 12, according to one or more embodiments.

Figure 12:
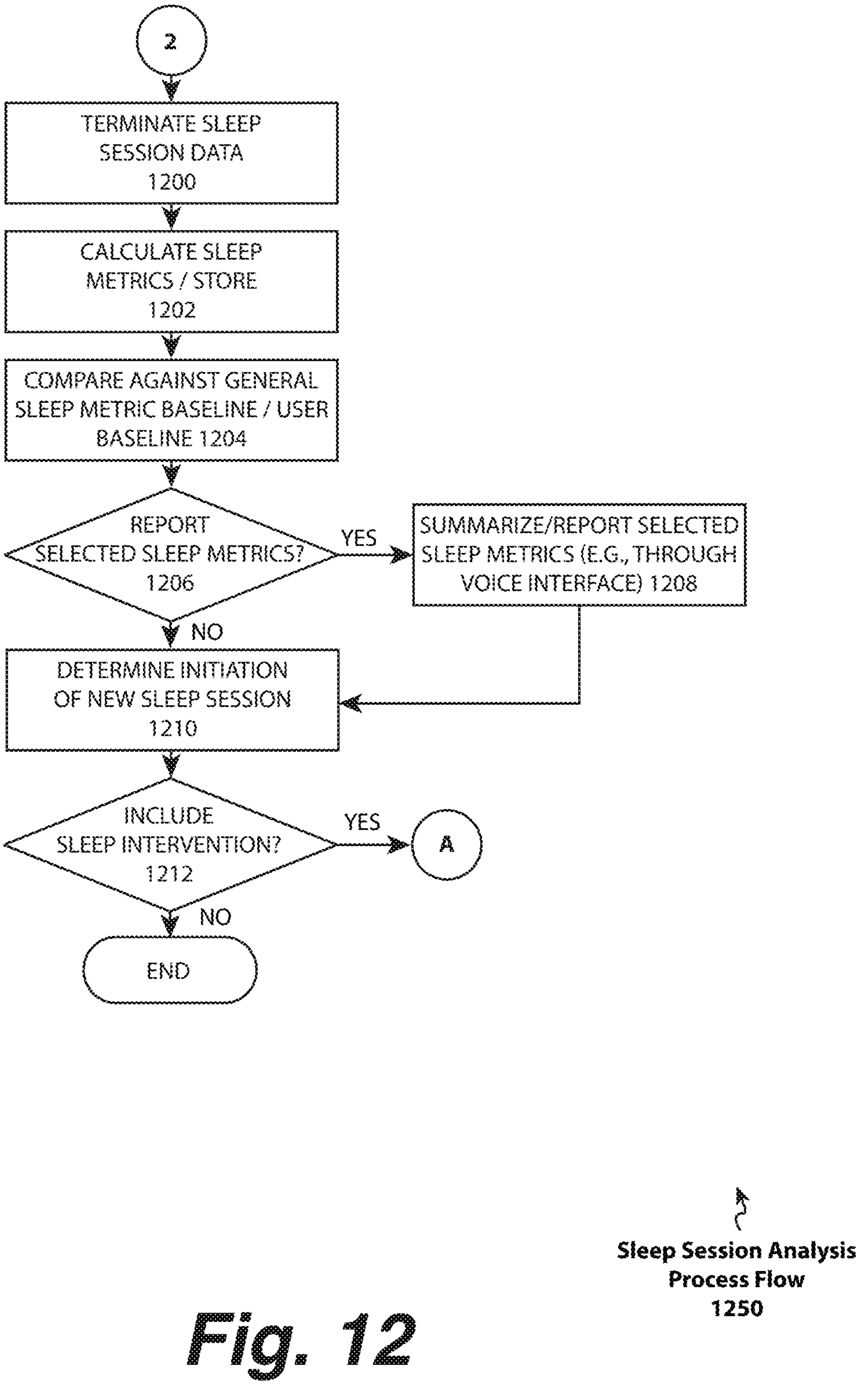
FIG. 12 illustrates a continuation of the sleep session analysis process flow of FIG. 11, according to one or more embodiments.

FIG. 12 illustrates a sleep session analysis process flow 1250, according to one or more embodiments. Operation 1200 terminates the sleep session data 414, for example upon a determination that the user 100 is in a concerned awake state or for another reason (e.g., an explicit instruction from the user 100 to stop tracking, an unstable network connection between one or more sensors over the network 106, etc.). Upon termination of the sleep session, the sleep session data 414 may store a sequence of specified time periods, each with an associated cognitive state, including timestamps of the initiation, transition, and/or termination of the cognitive state. Any periods of uncertainty during transition between cognitive states also may be stored.

Operation 1202 calculates one or more sleep metrics from the sleep session data 414, for example sleep onset latency, total sleep, interstitial wake-up periods, total REM sleep, number of REM sleep sessions, quality of sleep based on macro movements, snoring periods, sleep apnea periods (e.g., difficulty or cessation of breathing), unstable breathing periods, and/or other sleep quality metrics as may be known in the art of sleep science and sleep health. The sleep metrics may be stored in association with the user profile 410, for example within the sleep metrics data 418. Operation 1204 may compare the sleep metrics data 418 against a sleep metric baseline of a populations of users 100 and/or again to baseline of a particular user 100. For example, trends may be determined (e.g., the total sleep time of the user 100 has been steadily increasing over the last month), comparisons may be made (e.g., it takes the user 12 more minutes than the average population of users 100 to fall asleep, and the overall sleep quality of the user 100 is 18% lower than the average), and/or continued progression or regression may be tracked (e.g., if a sleep pattern continues to persist, the user 100 will be chronically deprived of sleep).

Operation 1206 determines whether one or more of the sleep metrics, for example stored within the sleep metrics data 418, are to be reported to the user 100. If the sleep metrics data 418 are to be reported, operation 1206 may proceed to operation 1208 which may report and/or summarize the selected sleep metrics, for example through a voice interface 104. In one or more embodiments, the sleep metrics data 418 may be held until an appropriate time for delivery. For example, the user 100 may awaken, and as soon as the concerted awake state is determined (or upon the user 100 asking), the summary may be read aloud to the user 100, e.g., by narrating the sleep metrics with a text-to-speech system. Operation 1208 may then proceed to operation 1210. Alternatively, where operation 1206 does not report and/or summary the sleep metrics data 418 for the user 100, operation 1206 may proceed to operation 1210. Operation 1212 determines whether the user 100 should receive a sleep improvement intervention 180, for example based on one or more of the sleep metrics or comparison thereof. For example, after determining the user 100 has not experienced a high-quality sleep for more than five days in the row, operation 1210 may determine that a sleep improvement intervention 180 should be formulated and presented to the user 100. The user 100 also may be queried, for example through the voice interface 104 or through a message to a software application on a device 650 (e.g., an "app" on a smartphone), as to whether the user 100 would like a sleep improvement intervention 180 to assist them in initiation sleep, maintaining sleep, and/or achieving quality sleep. If a sleep improvement intervention 180 is to be formulated, operation 1210 may proceed along path 'Circle A' to the embodiment of FIG. 15. Otherwise, operation 1520 may terminate.

Figure 13:
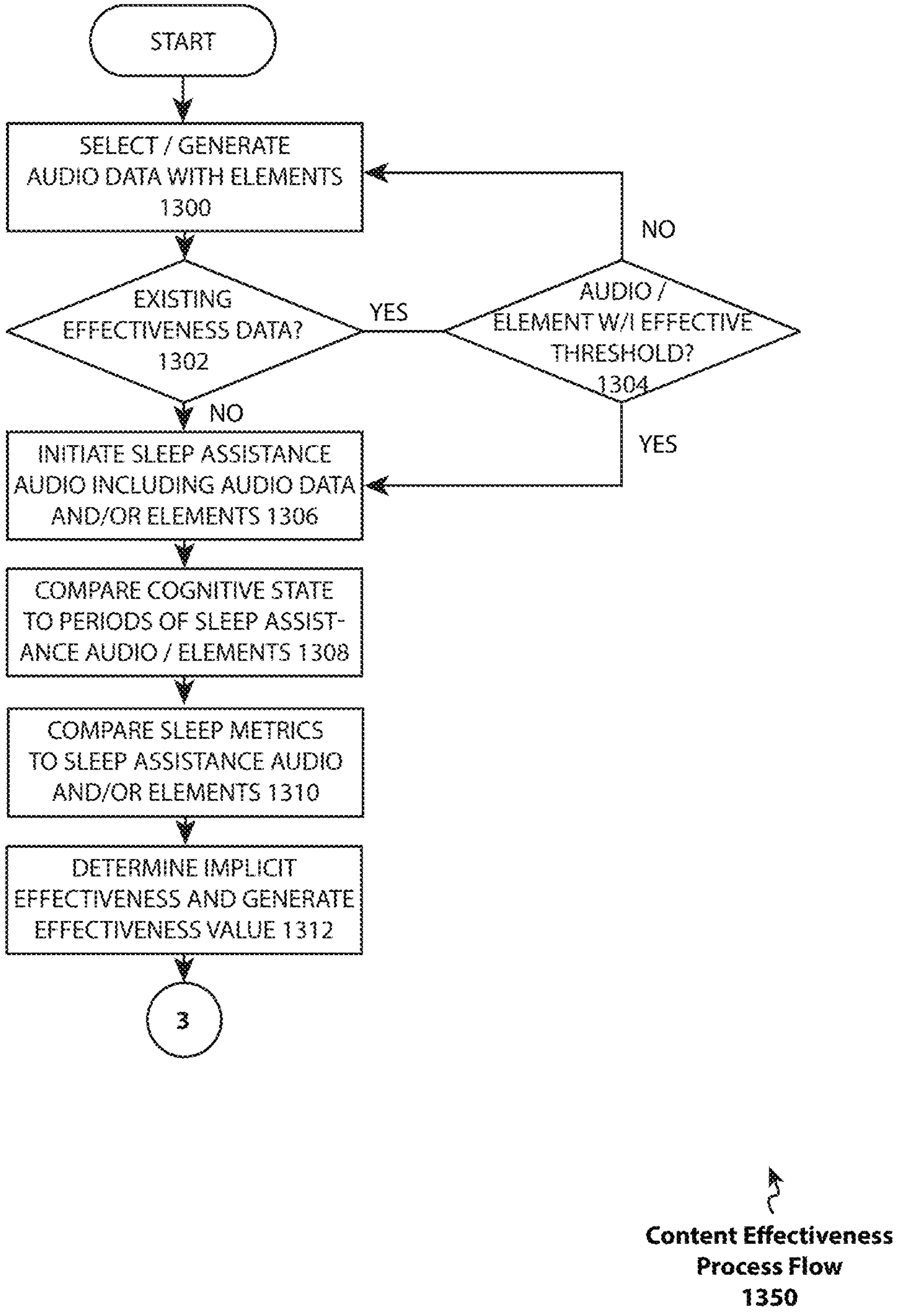
FIG. 13 illustrates a content effectiveness process flow, according to one or more embodiments.

FIG. 13 illustrates a content effectiveness process flow 1350, according to one or more embodiments. Operation 1300 may select and/or generate an audio data with one or more elements thereof. For example, the audio data may include generative sleep content 800 in which individual elements (e.g., musical sounds, musical phrases, musical layers such as melody or beats, particular complex or simple waveforms, narrative components, sentences, paragraphs, physiological guidance cues, etc.) may be discretely specified in time sequence with the audio data.

Operation 1302 determines if the audio data or elements thereof have been previously assessed for effectiveness, in which case operation 1302 may proceed to operation 1304 which may determine whether the selected audio or elements thereof meets an effectiveness threshold. For example, audio elements may be provided with an aggregate score based on an effectiveness rating or effectiveness value associated with each, contexts for positive or negative preferences for the same item, or the whole may have received an effectiveness score or value. If the effectiveness does not meet the threshold, operation 1304 may return to operation 1300 for selection of a different audio data and/or different elements thereof. For example, replacement of certain elements (which may be possible with generative audio) or selection of a different preexisting audio track that is still responsive to a request 107 of the user 100 may exceed the effectiveness threshold.

It should be noted that, with respect to operation 1300, operation 1302, and operation 1304, the prompts 702 may also be assessed for effectiveness, where each prompt 702, or group of prompts (e.g., those applying to narrative generation, such as the narrative prompt 730) may be treated as an element with a separate effectiveness determination. It may be known that the output of an AI model sometimes may be difficult to predict, and individual prompts may be likely to interact (e.g., with some combinations adventitious while some detrimental). However, utilizing one or more of the present embodiments for evaluating effectiveness, such predictability may improve over a period of time and/or after evaluating a number of requests 107. As a result, in one or more embodiments, the prompts 702 may be identified to be effective for sleep, and even correlated pairs or groups determined to be effective.

Similarly, in one or more embodiments the output of one or more generative content models 120 (e.g., the generative sleep content 800, or its pre-integrated components such as the narrative audio data 382 as shown and described in conjunction with FIG. 8) may be made to determine their constituent elements. The constituent elements then may be compared to those already evaluated with respect to the user 100 to determine probabilistic effectiveness of the input prompts 127 and/or the audio data in the pending outputs 810 (e.g., pre- or post-integration).

Where the audio or elements thereof are determined to exceed the threshold value for effectiveness, operation 1304 may proceed to operation 1306. Where the selected audio or elements thereof have never been assessed, operation 1302 may proceed to operation 1306. Operation 1306 may initiate a sleep assistance audio 102, including the audio data or elements thereof. The sleep assistance audio 102 may be generative (e.g., generated on demand and/or specifically for the user 100) and/or may be preexisting (e.g., recorded music, recorded breathing exercises, a recorded sleep story of a live voice actor with ambient sound added in post-production, etc.). Operation 1308 may compare cognitive state within a time period to the sleep assistance audio and/or elements thereof played during such time period. For example, it may be determined that while the audio data was being played on a speaker of a device for the user 100 that the user 100 had better physiological control over breathing and more rapidly lowered their heartbeat. Individual elements of the audio data may also be assessed. For example, it may be determined that a particular sound or series of sounds of one type (e.g., a music baseline) caused the heartbeat of the user 100 to increase. The determination may be made in the abstract (e.g., without regard to other data) and/or relative to other sounds of that type. Operation 1310 may compare one or more sleep metrics to the sleep assistance audio 102 or elements thereof. Operation 1312 may then apply an effectiveness value to the audio data of the sleep assistance audio 102 and/or each element thereof. In one or more embodiments, the effectiveness value provided through comparison to events of the sleep session data 414 and/or sleep metrics data 418 may be referred to herein as the "implicit effectiveness" of audio and/or its elements. In one or more embodiments, the audio data may receive a total effectiveness value based on sleep metrics data 418. Alternatively, or in addition, each of the elements of the audio data specified may receive an effectiveness value. For example, such effectiveness values for each element may be based on physiological events and/or physiological features associated with the playback or experiencing of such elements by the user 100, as may be temporally tracked within the sleep session data 414. In one or more other embodiments, the effectiveness of the whole or aggregate of elements may be imputed to all of the constituent elements. Many other approaches to determining element effectiveness and correlating element effectiveness will be apparent to one skilled in the art of statistics by reviewing one or more of the present embodiments. Following a determination of effectiveness, operation 1312 may proceed along path 'Circle 3' to the process flow of FIG. 14.

Figure 14:
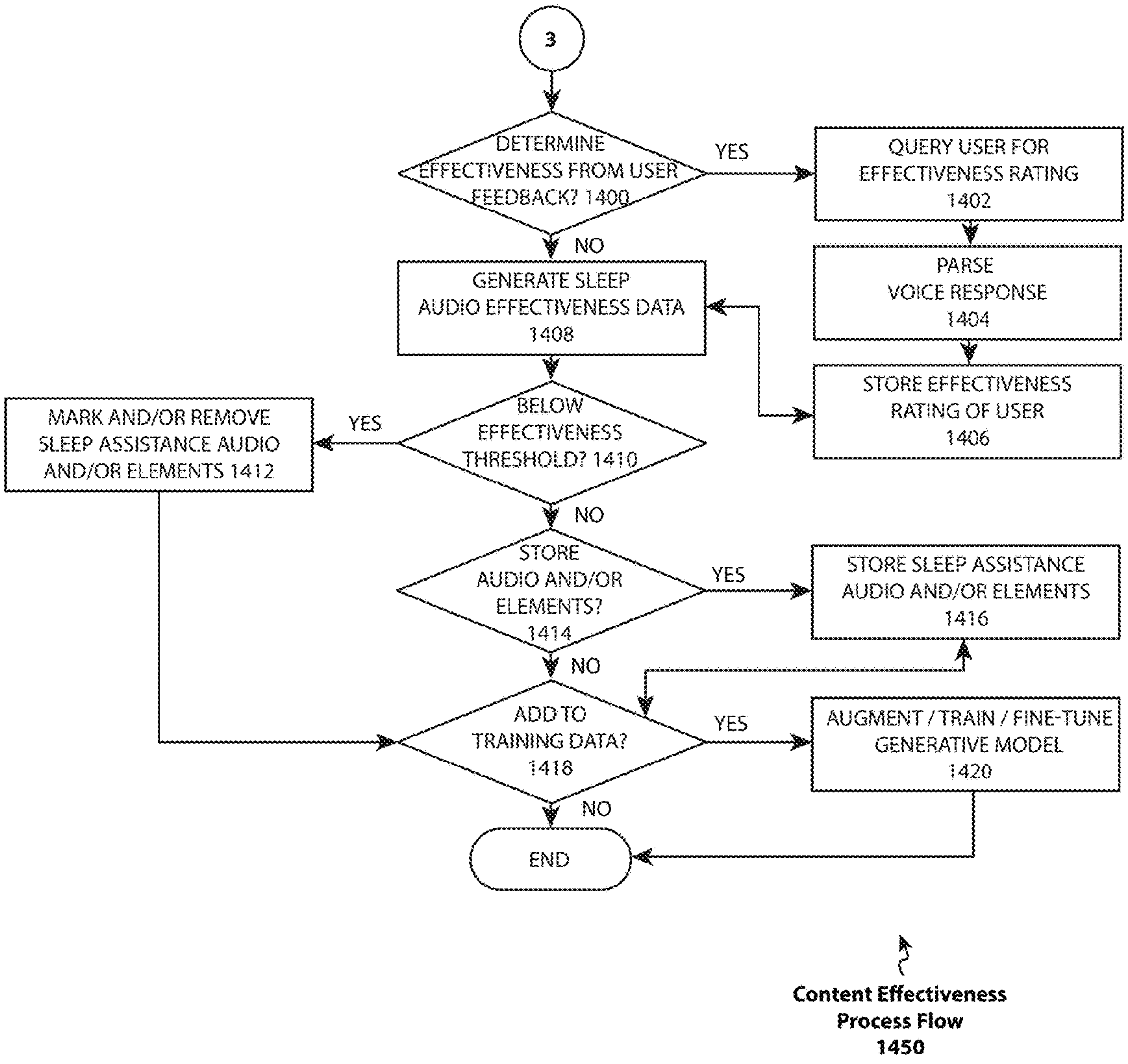
FIG. 14 illustrates a continuation of the content effectiveness process flow of FIG. 13, according to one or more embodiments.

FIG. 14 illustrates a content effectiveness process flow 1450, according to one or more embodiments. FIG. 14 may initiate at operation 1400, or operation 1400 may be a continuation of operation 1312 from the process flow of FIG. 13. Operation 1400 may determine if effectiveness should be assessed from user feedback, in which case operation 1400 may proceed to operation 1402, and otherwise proceed to operation 1408. Operation 1402 may query the user 100 for an effectiveness rating, for example through the voice interface 104. The query may be made upon occurrence of a condition, for example an end to the sleep session data, to ensure the query does not disturb the sleep (or initiation of sleep) for the user 100. In one or more other embodiments, the query may be made concurrently with playback of the sleep assistance audio 102, for example by playing a small chime, softly spoken request, or other barely noticeable request. For example, if the user 100 is awake, the user can respond to the gentle request, preferably in a quick or simple way (e.g., with a "good", "bad", a number between one and five, a slight nod or other head motion that can be determined from the IMU of a device, a slight tap on their body or an object that can be determined from the IMU, etc.).

Operation 1404 may parse a voice response of the user 100 which includes the effectiveness rating. The effectiveness rating may be specified within a predefined format or scale known to the user 100 and/or may be user-defined but normalized for statistical comparison and analysis. In one or more other embodiments, and especially if the user 100 may provide a narrative evaluation of the effectiveness (e.g., "it was good at the beginning, but then was too repetitive"), the voice response may be submitted to an artificial neural network that may be trained with training data comprising text descriptions of effectiveness evaluations each associated with ratings, scores, and/or other effectiveness metrics. Operation 1406 may then store the effectiveness rating of the user 100, for example in temporary memory, and proceed to operation 1408. In one or more embodiments, the effectiveness rating also may be referred to herein as explicit effectiveness. The effectiveness rating may occur for one or more elements (e.g., if the user 100 is asked to evaluate those elements or volunteers feedback), and/or the effectiveness rating may be imputed to all or some of the elements.

Operation 1408 may generate a sleep audio effectiveness data, for example stored within the sleep audio effectiveness data 421 within the user profile 410. The sleep audio effectiveness data may specify the sleep assistance audio 102 and/or its elements, along with the effectiveness values determined in the embodiment of FIG. 13 and/or the effectiveness ratings determined in the embodiment of FIG. 14.

Operation 1410 determines if the sleep assistance audio 102 and/or any of its elements are below a threshold value for effectiveness. If below the threshold value, operation 1412 may mark (e.g., tag with data) and/or remove (e.g., delete) the sleep assistance audio 102 and any of its elements. However, in one or more embodiments, effectiveness data with respect to the sleep assistance audio 102, a description of the sleep assistance audio 102 or its elements, and/or metadata thereof, may persist within the sleep audio effectiveness data 421 to provide data for future assessments and/or such that ineffective audio or elements thereof are not repeated. Operation 1412 may then proceed to operation 1418.

Where the audio data and/or elements are not below the effectiveness threshold, operation 1410 may proceed to operation 1414 which may determine whether the sleep assistance audio 102 or elements thereof should be stored for future use, either for the user 100 and/or for other users 100. For example, the user 100 may have provided explicit effectives feedback that a particular physiological guidance pattern was highly effective at inducing sleep quickly (especially a specific instantiation in which cues were associated with specific ambient sounds). The sleep assistance audio 102, or portions to which the user 100 referred, may be permanently stored in association with the user profile 410 such that the user 100 may have future access or use, and/or may share the sleep assistance audio 102 with one or more other users 100. If sleep assistance audio 102 or elements thereof are to be stored, operation 1414 may proceed to operation 1416 which may store the sleep assistance audio or elements thereof for future use. Operation 1416 may then proceed to operation 1418. Operation 1418 also may be arrived at if no storage of the sleep assistance audio 102 or elements thereof is to occur. Operation 1418 determines whether any of the audio effectiveness data 421 is to be utilized as training data, for example for one or more artificial neural networks that may comprise one or more of the generative content models 120. If no training data is to be presently defined, operation 1418 may terminate. If training data is to be utilized, operation 1418 may proceed to operation 1420 which may augment, train, and/or fine-tune one or more of the generative content models 120 such that the generative content models 120 may generate increasingly competent outputs.

In one or more embodiments, it will be recognized that one of the present advantages include that a user 100 may specify a portion of audio they like (e.g., "the first half", "right after the violin came in", etc.) and that portion may be recognized (e.g., through an artificial neural network), isolated. Then, to the benefit of the user 100, additional sleep content matching or stylistically coordinating with the portion may be created through one or more of the generative content models 120. For example, an input prompt to the music generation model 140 may include a 30 second portion of a music audio (whether generative or prerecorded), with an instruction to "extend" or "vary" the music audio within the structure, style, or other quality of the music audio, as may be known in the art of AI models.

Figure 15:
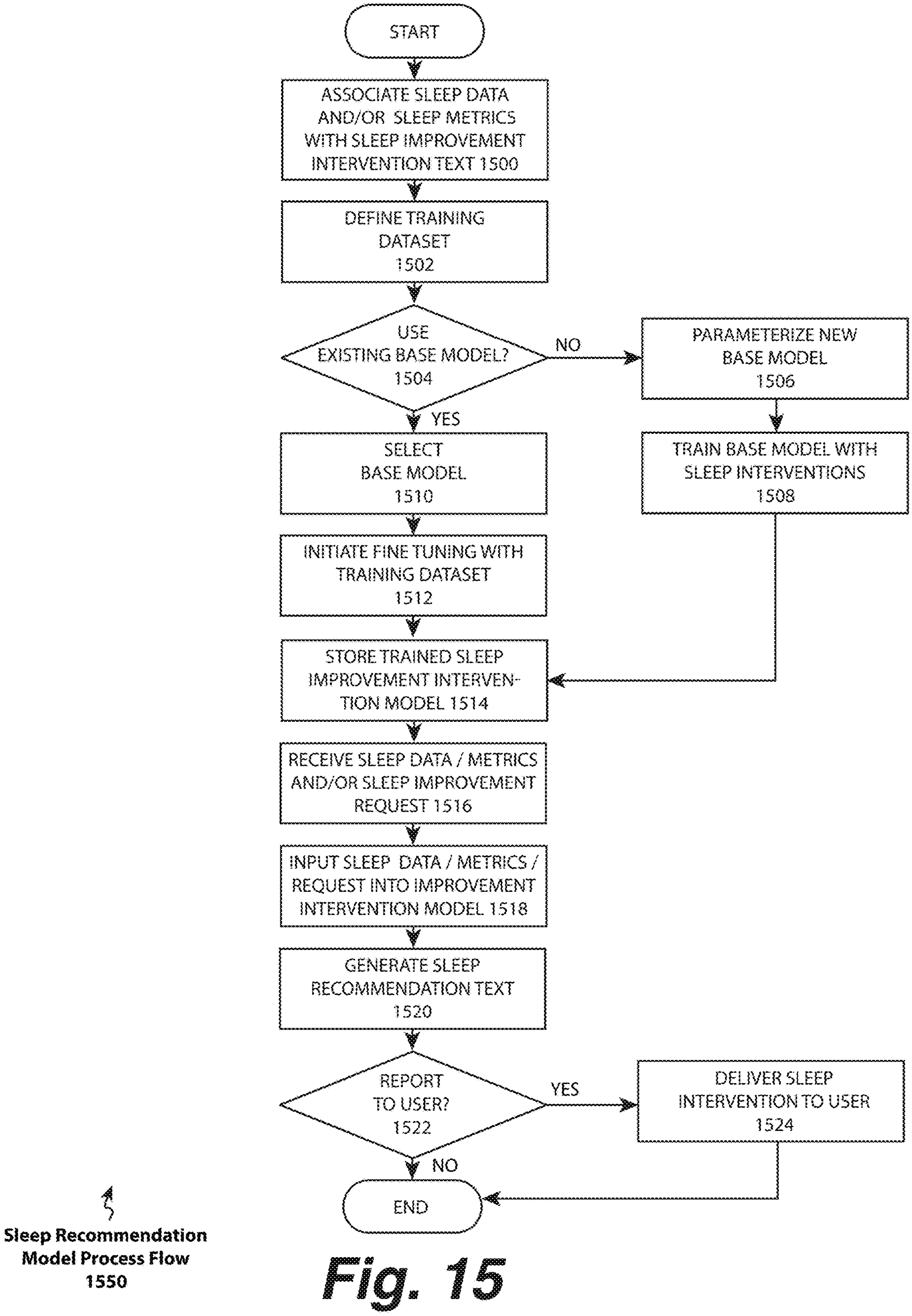
FIG. 15 illustrates a sleep recommendation and intervention model process flow, according to one or more embodiments.

FIG. 15 illustrates a sleep recommendation and intervention process flow 1550, according to one or more embodiments. Operation 1500 through operation 1514 illustrate one method of training of a sleep assistance model 115, and specifically a portion that may be utilized for generation of sleep improvement interventions 180, according to one or more embodiments. Operation 1500 may associate (i) the sleep data (including for example the sleep session data 414, the physiological data 205 or features thereof, etc.) and/or sleep metrics data 418, with (ii) text describing sleep improvement interventions 180 and/or sleep condition diagnoses matchable to predefined sleep improvement interventions 180 tagged with such condition. The sleep metrics data 418 and/or sleep data may be transcribed into text form to assist in utilizing a predictive text model that receives text as an input and outputs predictive text as an output, such as a large language model. The transcription may also include summarization (e.g., translating raw data showing a week of poor sleep as "the user has experienced seven nights of poor sleep."). Operation 1502 may then define the training dataset, for example as a stored training dataset file. Operation 1504 may determine whether an existing base model should be selected (e.g., a base LLM 111). If an existing base model is to be selected for fine-tuning, operation 1504 may advance to operation 1510. However, where no new base model has been selected, operation 1504 may proceed to operation 1506 which may parameterize a new base model.

Operation 1506 may then train the base model with the training data, for example to adjust all node weights and fix other "learnable" parameters within an artificial neural network as known in the art of AI models. Operation 1508 may then proceed to operation 514.

It should be noted that, in one or more embodiments, a substantial training dataset may be required to train a competent base model from scratch (e.g., to assign values to nodes or other parameters unassigned, unvalued, and/or random node weights). However, in one or more embodiments, the each of the data sources of operation 1500, and/or other sleep metrics shown and described herein, may provide the substantial training dataset when gathered over a period of time and/or for a group of users 100.

Where an existing base model is to be utilized, operation 1504 may proceed to operation 1510 which may select an existing base model, for example a large language model such as Llama2®. Operation 1512 may then initiate fine tuning with the training dataset, for example readjusting one or more node weights and/or other adjustable parameters of the artificial neural network of the large language model. Operation 1514 may then store the trained sleep improvement intervention model in computing memory. The sleep improvement intervention model then may be set up for production, including receiving prospective requests 107 from additional users 100. Although the embodiment of FIG. 15 refers to a specialized model for sleep improvement interventions, as shown and described above, the sleep improvement intervention model may be incorporated within the sleep assistance model 115 (the sleep assistance model 115 may encompass training for the other capabilities, such as responding to general sleep information and/or controlling a device), according to one or more embodiments.

It will be recognized that other specialized forms of artificial neural network model, and training and evaluation thereof, may be effected through one or more of the techniques described herein. For example, in one or more embodiments, an artificial neural network may receive as input physiological feature data over time and output an issue diagnosis. The training dataset may include many instances of the sleep session data 414, each associated with one or more diagnoses (or probabilities thereof) assigned by a trained sleep physician or clinical researcher. Other models may receive as inputs the raw data from sensors, such as the physiological data 205, to generate such diagnoses. Operation 1516 may receive sleep data (e.g., the sleep session data 414), the sleep metrics data 418, and/or data from a sleep improvement request 170. Operation 1518 may input the sleep data, sleep metrics data 418, and/or request of the user 100 into the inputs of the sleep improvement intervention model (which may be included within the sleep assistance model 115). Operation 1520 may then generate a sleep improvement intervention 180, according to one or more embodiments, for example as a predictive text output of a large language model trained with the training dataset.

Operation 1522 may determine whether to report the sleep improvement intervention 180 to the user 100. For example, in one or more embodiments, the sleep improvement intervention 180 may be held until the most opportune or appropriate time, as may be based on both the schedule of the user 100 and/or the type of sleep intervention. For example, the user 100 may be informed or reminded at noon that any vigorous exercise should occur at least five hours before intended sleep, as a result of the user 100's typically bedtime schedule, this may mean prior to 4 PM. If the sleep improvement intervention 180 or portion thereof should be reported, operation 1522 may proceed to operation 1524 which may deliver the sleep improvement intervention 180 to a device of the user 100 (including delivery via the voice interface 104, according to one or more embodiments).

In one or more embodiments, and as shown and described in conjunction with the embodiment of FIG. 1B and FIG. 2, it will be recognized that the sleep improvement intervention 180 may be tracked and assessed for effectiveness, both implicitly (e.g., through sleep data, sleep session data 414, and/or sleep metrics data 418) and explicitly (e.g., through explicit feedback or ratings of the user 100).

In one or more embodiments, it will be recognized that certain audio, characteristics, and/or elements of the audio may be useful in addressing particular types of challenges the user 100 may be experiencing with sleep. In one or more embodiments, one or more of the techniques as described herein can be utilized to evaluate effectiveness with respect to certain conditions, issues, or challenges related to sleep. For example, certain audio, breathing exercises, or elements thereof may be particularly capable at reducing anxiety and inducing sleep in the context of anxiety of the user 100.

In one or more embodiments, an artificial neural network may include a training dataset comprising an association of (i) determined sleep condition or challenge, (ii) sleep assistance audio 102 or elements thereof, (iii) effectiveness scores associated with the effectiveness of addressing the particular sleep condition or challenge, including with respect to sleep KPIs such as sleep onset latency.

Figure 16:
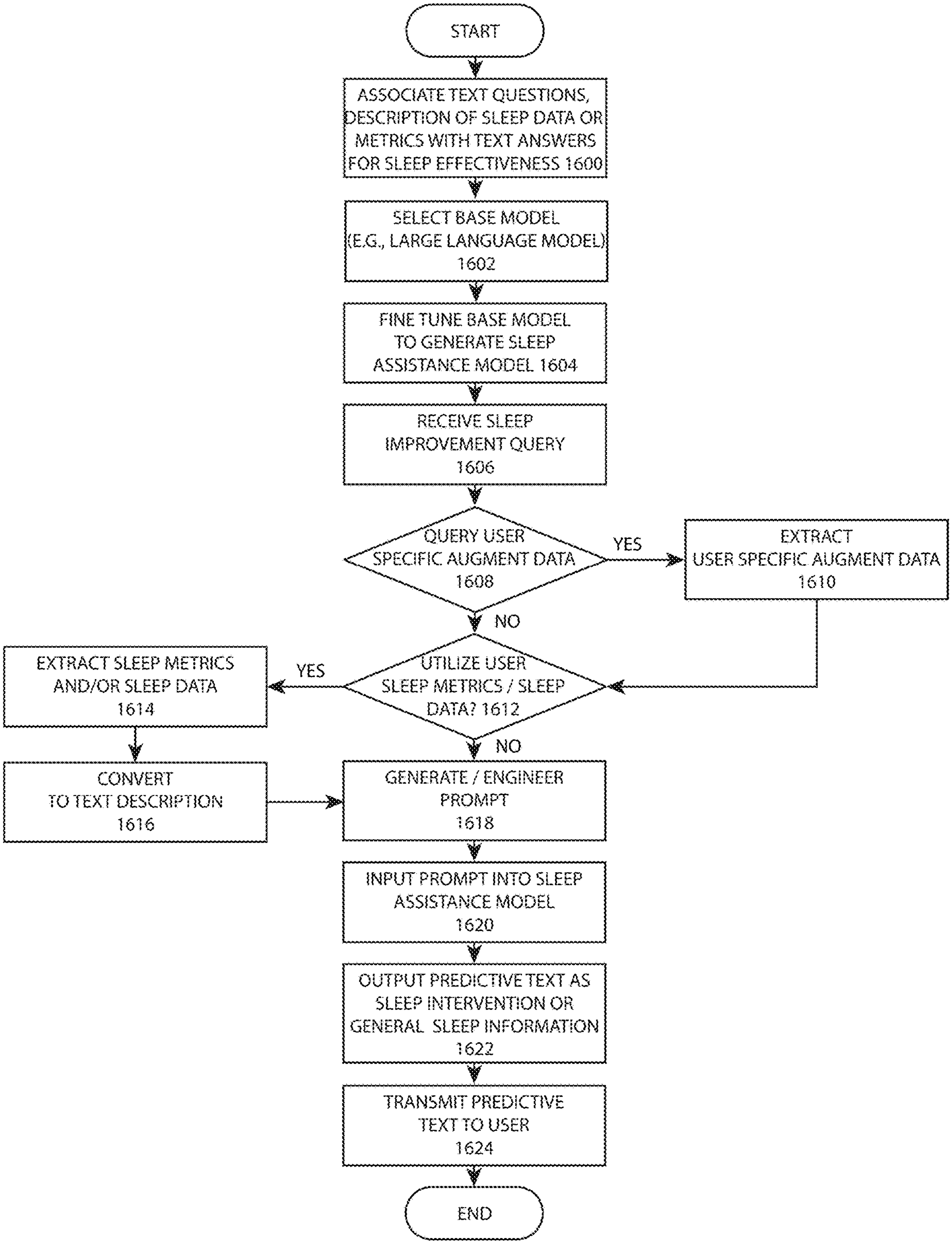
FIG. 16 illustrates a sleep assistance model process flow, according to one or more embodiments.

FIG. 16 illustrates a sleep assistance process flow 1650, according to one or more embodiments. In one or more embodiments, FIG. 16 may illustrate a method for training and utilizing the sleep assistance model 115, including both responding to general queries for information about sleep and responding to sleep improvement requests 170 resulting in generation of sleep improvement interventions 180.

Operation 1600 may associate (i) text questions (e.g., example instances of the sleep improvement request 170 and/or general requests for sleep information) and/or descriptions of sleep data or sleep metrics with one or more text answers that are considered competent responses, as may be reviewed by sleep experts, and/or dedicated review personnel. In one or more embodiments, the text questions and text answers may also include what may be determined to be effective responses based on one or more sleep improvement requests 170. The text questions with the text answers may define a training dataset and/or a fine-tuning dataset.

Operation 1602 may select a base model for fine tuning, for example a large language model. It will be noted that the base model, depending on its training dataset (e.g., a multitude of webpages and other documents available over the Internet), may have some level of competence in responding to general questions about sleep. However, base models may include a static training dataset that may lack new information, may include inaccurate information, and/or may be have other extraneous training information that may negatively influence and/or lower the competence of the output. The base model may also include inaccurate information in disproportion to accurate or effective information, which may result in incompetent predictive outputs. In one or more embodiments, it may be possible to utilize a base model without further customization and/or specialization. However, in one or more preferred embodiments, augmentation and/or fine-tuning may be advantageous. As such, operation 1604 may fine-tune the base model to generate a sleep assistance model 115 that is specialized for addressing sleep-based answers.

Operation 1606 may receive a sleep improvement request 170 from the user 100, for example through the voice interface 104 of a device (e.g., the earphones 600 having a microphone 608) transmitted over the network 106 to a server or other computing system within a request 107. Operation 1608 may then determine if a user specific augment data 123 should be utilized to gather additional context related to the user 100. The additional context, for example, might include: previous sleep improvement requests 170 of the user 100; sleep improvement interventions 180 attempted, completed, or continuously utilized, previous results or effectiveness values; and/or other data. Operation 1610 extracts the user specific augment data 123 or relevant portion thereof responsive that may be determined through one or more additional processes to be responsive to the sleep improvement request 170. The user specific augment data 123 may be loaded into data container storing prompts, potential prompts, and/or additional data for a context window (e.g., the context window 126) to be utilized in conjunction with input prompts 127. Operation 1610 may then proceed to operation 1612.

Operation 1612 may determine if sleep data (e.g., the physiological data 205, the sleep session data 414) and/or sleep metrics data 418 are to be utilized. If sleep data and/or sleep metrics are to be utilized, operation 1612 may proceed to operation 1614 which may extract the sleep data from the sleep session data 414, and/or the sleep metrics from the sleep metrics data 418, for example by querying the user profile 410 of the user 100. The sleep data and/or sleep metrics data 418 may be converted into a text description in operation 1616, such that the inputs may be able to be more easily ingested by the sleep assistance model 115, according to one or more embodiments. Operation 1616 may then proceed to operation 1618. Operation 1618 may generate and/or engineer a prompt for submission to the sleep assistance model 115. For example, the prompt may include data from the sleep improvement request 170, the user specific augment data 123, the sleep session data 414, and/or sleep metrics data 418 (including across one or more sessions, or the baselines, averages, and/or summaries thereof). It should be noted that data from a general sleep model augment data 122 may be utilized as well. However, in one or more embodiments, the fine-tuned model for the sleep assistance model 115 may incorporate the general, population-wide information to be included within the model and that might otherwise be need to be moved into the context window 126 to influence the predictive output.

Operation 1620 may input the prompt into the sleep assistance model 115. Operation 1622 may output predictive text (e.g., the predictive text 182) that may include the sleep improvement intervention 180, or general information about sleep, as the case may be. Operation 1624 may transmit the predictive text 182 to a device of the user 100 for delivery, for example a smartphone or over to speakers 606 of the earphones 600. Operation 1624 may then terminate. In one or more embodiments, the sleep improvement intervention 180 may include a set of concrete steps to improve one or more sleep metrics that may be tracked within the sleep metrics data 418. The sleep improvement intervention 180 may be separated depending on when one or more steps are best implemented. For example, as part of a comprehensive sleep health program: (i) any advice pertaining to post wake-up period may be delivered in the morning (e.g., to the smartphone of the user 100 if the voice interface 104 is not currently being utilized); (ii) any advice related to eating may be delivered prior to dinner (e.g., around 6 PM); (iii) any pro-relaxation steps may be delivered at initiation of the sleep session, etc. In one or more embodiments, and as further described above, the sleep improvement intervention 180 may be monitored for implementation (e.g., through sensors and/or queries to the user 100) and/or may be tracked for effectiveness. The resulting effectiveness data may be usable to both update the model augmentation data (e.g., within the text RAG data 112), and/or re-train or otherwise update the fine-tuning of the sleep assistance model 115.

Figure 17:
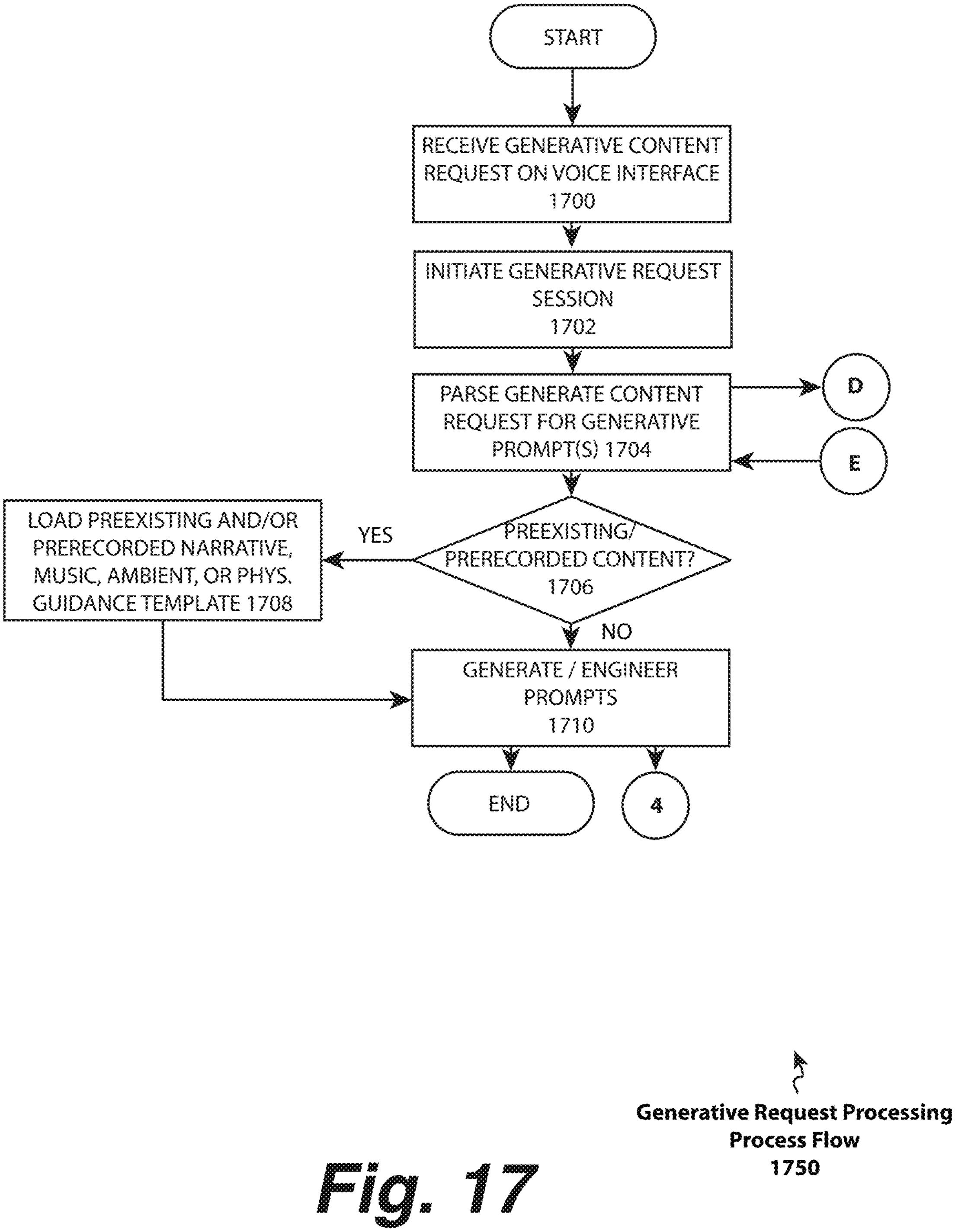
FIG. 17 illustrates a generative request processing process flow, according to one or more embodiments.

FIG. 17 illustrates a generative request processing process flow 1750, according to one or more embodiments. Operation 1700 receives a generative sleep content request 700 from a user 100 through a voice interface 104, for example implemented with a set of earbuds having a microphone 608 and a speaker 606. The generative sleep content request 700 may have been received or parsed from a request 107 including one or more additional requests, for example requests for controlling a device (such as the earbuds) and/or request for formulation of a sleep assistance improvement intervention 180. Operation 1702 initiates a generative request session. In one or more embodiments, a data container may be initiated for receiving data to formulate and/or engineer prompts from one or more sources, beginning with the generative sleep content request 700. Operation 1704 may then parse the generative request for one or more generative prompts. An example parsing process for the generative request is shown and described in conjunction with the embodiment of FIG. 18.

Operation 1706 determines if any preexisting and/or prerecorded content is to be utilized within the generative sleep content request 700. For example, the user 100 may have identified an existing audio track that they would like the sleep assistance audio 102 to be "similar to" and/or include a portion of. If preexisting and/or prerecorded content is to be utilized, operation 1706 may proceed to operation 1708, which may load the preexisting and/or prerecorded content, including any narrative, music, ambient sound, and/or a physiological guidance template. In one or more embodiments, rather than loading the content, individual elements thereof may be loaded. Similarly, descriptors of characteristics of the content (e.g., genre, style, instruments, story elements, etc.) may be loaded. Operation 1710 may then generate and/or engineer one or more prompts (e.g., the prompts 702) for the generative request.

Operation 1710 may then terminate, for example storing the prompts 702 for later use, and/or proceed along path 'Circle 4' to the process flow of the embodiment of FIG. 19.

FIG. 18 illustrates a generative request parsing process flow 1850, according to one or more embodiments. The generative request parsing process flow 1850 may implement one or more parsing processes of the generative sleep content request 700, for example operation 1704 of the generative request processing process flow 1750. Operation 1800 may determine whether a narrative generation request is present within the generative sleep content request 700. For example, the generative sleep content request 700 may have been preformatted (e.g., the user 100 guided through providing each portion of their generative request, including narrative generation). If it is not included, operation 1800 may proceed to operation 1806. Where a narrative request is included, operation 1800 may proceed to operation 1802 which may extract the narrative prompt 730. Operation 1802 may then optionally determine one or more narrative modifiers 732, such as the narrative style description 734 and/or the narrative genre description 736. Any of the modifiers shown and described as part of the prompt 702, such as in the present case the narrative modifiers 732, may be usable to compare against previously utilized prompts 702 for effectiveness and/or implicit or explicit preferences of the user 100. In one or more other embodiments, the generative sleep content request 700 may be submitted to an artificial neural network trained to recognize, and/or generate prompts 702, which may implement operation 1800, operation 1802, and/or operation 1804.

Operation 1806 may determine whether a music generation request is present within the generative sleep content request 700. Where the music generation request is not included, operation 1806 may proceed to operation 1812. Where music request is included, operation 1806 may proceed to operation 1808 which may extract the music prompt 740. Operation 1810 may then optionally determine that one or more music modifiers 742 are present, such as the music style description 744 and/or the music genre description 746. In one or more other embodiments, the generative sleep content request 700 may be submitted to an artificial neural network trained to recognize and/or generate prompts 702, which may implement operation 1806, operation 1808, and/or operation 1810.

Operation 1812 may determine whether an ambient sound generation request is present within the generative sleep content request 700. In the case that no ambient sound generation request is included, operation 1812 may proceed to operation 1818. Where ambient sound request is included, operation 1812 may proceed to operation 1814 which may extract the ambient sound prompt 750, and operation 1816 may then optionally determine one or more ambient modifiers 752, such as the ambient style description 754 and/or the ambient filter 753. In one or more other embodiments, the generative sleep content request 700 may be submitted to an artificial neural network trained to recognize and/or generate prompts 702, including the ambient sound prompt 750 or portions thereof, which may implement operation 1812, operation 1814, and/or operation 1816.

Operation 1818 may determine if a "forced" music and/or ambient sound is to be included, even if not present within the generative sleep content request 700. For example, the user 100 may have requested physiological guidance and/or a "sleep story" (e.g., a narrative text translated from text to speech), but it may be assumed, or customary, to generate supporting music or ambient sound. If forced music or ambient sound is not included, operation 1818 may proceed to operation 1822. If forced music and/or ambient sound is to be included, operation 1818 may proceed to operation 1820. In one or more embodiments, operation 1818 may then proceed to operation 1820, which may generate music prompts 740 and/or ambient sound prompts 750 utilizing the narrative prompt 730 or portions thereof. For example, a text-text translation array may be utilized to determine proximate, responsive music or ambient sound descriptors to one or more words within the generative sleep content request 700 and/or narrative prompts 730. As just one example, if a narrative genre description 736 includes a western story, a western music genre and/or folk music genre may be selected as the music genre description 706.

Operation 1822 may determine whether a physiological guidance request is present within the generative sleep content request 700. Where the physiological guidance request is included, operation 1822 may proceed to operation 1824, which may extract the physiological guidance prompt 760, and operation 1826 may then optionally determine one or more physiological guidance modifiers 762, such as a physiological guidance type 764. In one or more other embodiments, the generative sleep content request 700 may be submitted to an artificial neural network trained to recognize, and/or generate prompts 702, including the physiological guidance prompt 760 or portions thereof, which may implement operation 1822, operation 1824, and/or operation 1826.

Following execution of operation 1800 through operation 1826, a data container may include discrete prompts 702 which may be compared, supplemented, de-duplicated, and/or otherwise manipulated or engineered. For example, and as shown and described in conjunction with the embodiment of FIG. 7, a session RAG data 124 may store the prompts 702, which then may be further engineered and/or supplemented through comparison and filtering against the general sleep augment data 122, the user specific sleep augment data 123, and/or other data, for example as shown and described in conjunction with the embodiment of FIG. 19.

Figure 19:
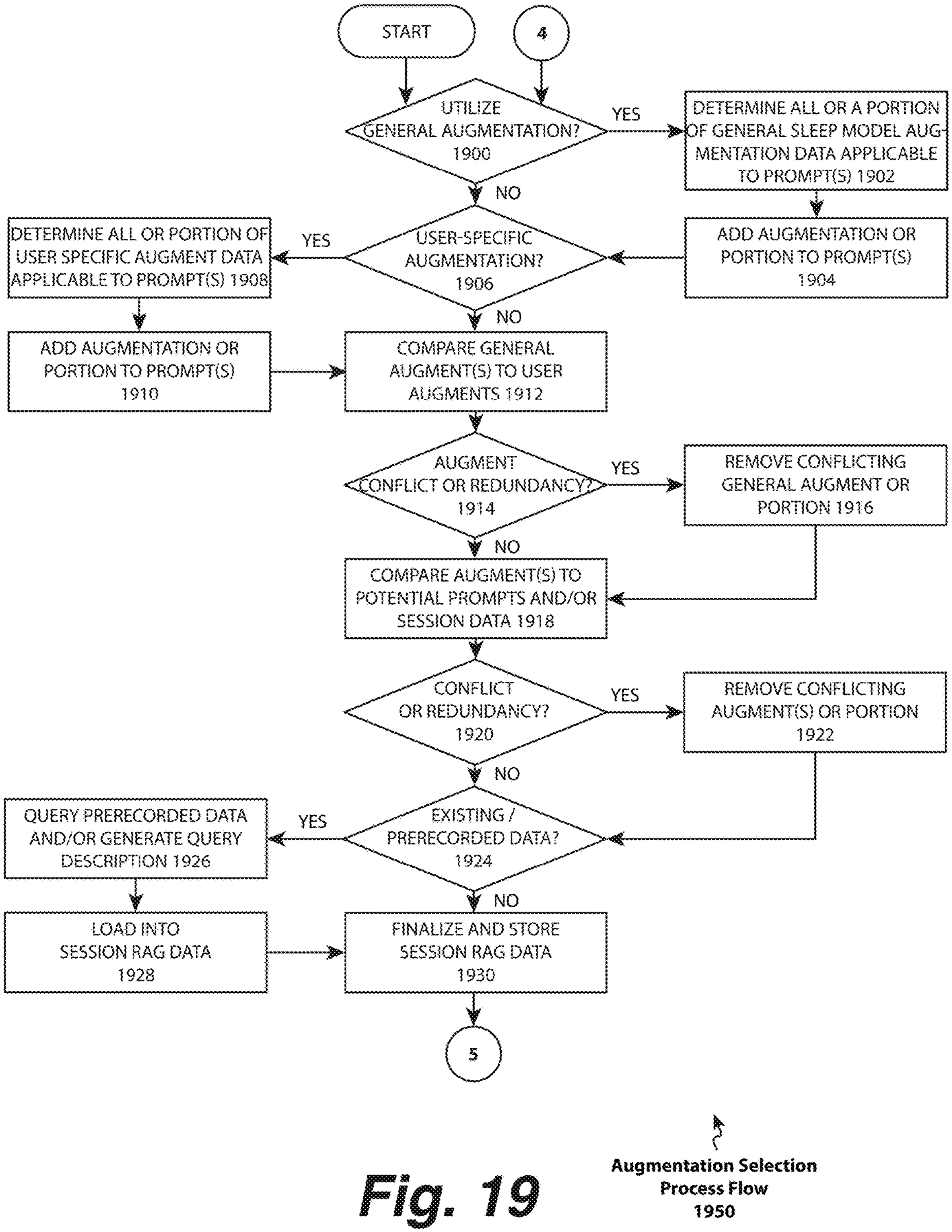
FIG. 19 illustrates a model augmentation process flow, according to one or more embodiments.

FIG. 19 illustrates a model augmentation process flow 1950, according to one or more embodiments. The model augmentation process flow 1950 may be utilized to augment one or more prompts (e.g., the prompts 702, prompts for a general sleep information query, prompts requesting a sleep intervention, etc.) and/or AI model inputs. The potential prompts may be temporarily stored in a data container within computing memory, for example the session RAG data 124. The model augmentation process flow 1950 may be initiated at operation 1900 with an existing set of prompts and/or potential AI model inputs, and/or may be a continuation of the embodiment of FIG. 17 along path 'Circle 4'.

Operation 1900 may determine whether to utilize a general augmentation data, for example intended for use with, or as data applicable to, a broad population of users 100 and/or sub-population of users 100. As shown and described herein, the general augmentation data (e.g., the general sleep model augment data 122) may be selected to improve outputs of one or more artificial numeral networks by providing additional information or "context" within the input nodes 127 and/or the context window (e.g., the context window 126). If no general augmentation is to be utilized, operation 1900 may proceed to operation 1906. If a general augmentation is to be utilized, operation 1900 may proceed to operation 1902. Operation 1902 may determine all or a portion of the general sleep model augment data 122 applicable to the prompts 702. For example, the general sleep model augment data 122 may store data in a structured hierarchy depending on one or more intended platform capabilities, for example: generating generative content and sub-portions thereof, generating sleep improvement interventions 180 and sub-portions thereof, etc. Other data structures may include graph data structures (including data modeling of interconnected factors, concepts, content, interventions, and/or considerations). In one or more other embodiments, the data within any augmentation data source may be unstructured and further parsed on demand to determine relative portions based on closeness of textual concepts from a text-text relation model. Operation 1904 may then add the augmentation or portion thereof to the prompts already assembled (e.g., within the session RAG data 124), and proceed to operation 1906.

Operation 1906 determines whether a user-specific augmentation should be utilized, in which case operation 1906 may proceed to operation 1908. If no user specific augmentation is to be utilized, operation 1906 may proceed to operation 1912, as further described below. Operation 1908 may determine all or a portion of the user specific augment data 123 applicable to the prompts 702. The general sleep model augment data 122 may have a similar data structural organization as the general sleep model augment data 122, or may be organized differently, according to one or more embodiments. Operation 1910 may then add the augmentation or portion thereof to the existing prompts, and proceed to operation 1912 once compiled.

Operation 1912 through operation 1924 may then compare the text or other data and (i) remove redundancies, (ii) remove conflicts, (iii) vary prompts, and/or (vi) reinforce or supplement positive prompts. Although one order is illustrated, it will be apparent that multiple orders and/or priorities of integrating data from the various sources may be adopted and utilized to achieve the goal of flexible supplementation and/or engineering of the prompts 702.

Operation 1912 compares any the general augments to the user augments (e.g., general sleep model augment data 122 to the of the user specific augment data 123). For example, the comparison may be made line-for-line in high structured data. In such case that the existing prompts and augmentation data are text intended for a large language model, composition may be made through a text-text relation model evaluating the similarity of words, phrases, and/or concepts. Operation 1916 may remove a conflicting general augmentation or portion thereof from the potential prompts. In this example, priority is provided to the user specific augment data 123 as likely more relevant, effective, and/or having a higher probability of resulting in a competent and/or effective output of an artificial neural network (such as may be used by the sleep assistance model 115 and/or one or more of the generative content models 120). Operation 1916 may then proceed to operation 1918, which may compare all remaining augments (e.g., non-conflicting portions of the general sleep model augment data 122 and the user specific augment data 123) to the request 107 of the user 100 and/or session RAG data 124.

Operation 1920 determines a conflict and/or redundancy in the remaining augmentation data and the prompts 702 submitted by the user 100. Operation 1922 may then remove conflicting or redundant pending augmentations (e.g., removed from the remaining portions of the general sleep model augment data 122 and the user specific augment data 123), giving priority to existing pending prompts 702. In one or more embodiments, there may be exceptions to priority. For example, where the user 100 includes the term "insomnia" in their request for an intervention, but no prior data such as the sleep metrics 418 show the user 100 has signs of insomnia (e.g., as may be determined from querying the user profile 410), the user 100 may be likely utilizing the term "insomnia" colloquially for "sleeplessness". Clarification may be requested from the user 100 before proceeding to prioritize or de-prioritize the prompts 702 from the present request 107, for example as may have been assembled within the session RAG data 124.

Operation 1924 may determine whether an existing and/or prerecorded data is to be utilized as an input. For example, where the user 100 has requested a music track or sleep story that is preexisting, but may then request the support of additional generative content, operation 1924 may proceed to operation 1926 which may optionally query the prerecorded data and/or generate or query a description of the prerecorded data. For example, where one or more generative models can receive a sample of an audio track as a model input, the sample may be extracted and utilized. In one or more other embodiments, a description of the music, its elements, and characteristics may be utilized. Operation 1928 may then load the prerecorded data, portion thereof, or description thereof, into the session RAG data 124. Operation 1928 may then proceed to operation 1930 which may finalize the session RAG data 124 as potential inputs to the input prompts 127 (e.g., the sleep assistance model 115, one or more generative content models 120, etc.). In such case that the sleep session RAG data 124 includes a sleep improvement request 170, the finalized prompts relating to the sleep improvement request 170 may be input into the sleep assistance model 115 and/or context window 126 thereof. In the case in which the sleep session RAG data 124 includes a generative sleep content request 700 input, prompts 127 from the sleep session RAG data 124 may submitted to relevant generative content models 120. In one or more embodiments, the sleep session RAG data 124 may be further parsed, and a possible order of content generation utilized, in which case operation 1930 may proceed along path 'Circle 5' to the process flow of the embodiment of FIG. 20.

FIG. 20 though FIG. 25 illustrate one method for generation of the generative sleep content 800, including physiological guidance, a voice narrative, supporting music and ambient sound, and/or integration thereof into the sleep assistance audio 102, according to one or more embodiments.

FIG. 20 illustrates a physiological guidance content generation process flow 2050, according to one or more embodiments. The physiological guidance content generation process flow 2050 may initiate at operation 2000, and/or may continue from operation 1930 of the process flow of FIG. 19 along path 'Circle 5'.

Operation 2000 may determine whether the generative sleep content request 700 includes a physiological guidance prompt 760. In one or more embodiments, the physiological guidance prompt 760 and any generation of a physiological guidance template may be the first to be performed to ensure physiological guidance cues properly appear in other generative content. This may be especially the case if the cues are implemented or "translated" into music or ambient sound. If no physiological guidance is included, operation 2000 may proceed along path 'Circle F' to the embodiment of FIG. 21. Where a physiological guidance prompt 760 is included, operation 2000 may proceed to operation 2002.

Operation 2002 may determine whether the generative sleep content request 700 includes a request for generative physiological guidance (e.g., generation of both pattern of cues and rendering of cues), a request for generative audio based on a template physiological guidance cues and relative timings therefore, and/or a request for recorded physiological guidance audio 560. Where generative content is not intended to generate the physiological guidance, operation 2002 may proceed to operation 2004 which may determine whether audio data should be utilized, in which case operation 2004 may proceed to operation 2006 which may load the recorded physiological guidance audio 560. For example, the recorded physiological guidance audio 560 may be loaded as one of the files and/or data usable during integration with one or more other generative outputs of the generative content models 120. Operation 2006 may then proceed to operation 2016, which may optionally add a description of the recorded physiological guidance audio 560 to the context window 126, for instance to assist in passing context and/or increasing the probability of structural or stylistic integration.

If no recorded audio data is to be utilized, operation 2004 may instead proceed to operation 2008, which may select a preexisting physiological guidance template, for example data describing temporally spaced cues which may act as a data scaffold upon which audio may be rendered as sound, including: a voiceover of the physiological guidance (e.g., "breath in"), music, narrative, and/or ambient sound. Operation 2010 may then proceed to operation 2016, which may optionally add the physiological guidance template and/or textualize (e.g., generate a description of) the physiological guidance template into the context window 126. In one or more embodiments, the physiological guidance template may be utilized as a constraint on one or more generative content models 120, for example requiring adherence to the temporal timing of the physiological guidance cues within the template.

Returning to the decision of operation 1202, where generative content is to be utilized in generation the physiological guidance template, operation 2002 may proceed to operation 2012. Operation 1202 may input the physiological guidance prompt into a physiological guidance model 160, for example as shown and described in conjunction with the embodiment of FIG. 1C. Operation 2014 may then generate the physiological guidance template and proceed to operation 2016. Optionally, the generated physiological guidance template, description thereof, or portion thereof may be added to the context window 126, according to one or more embodiments. Operation 2016 and/or operation 2007 may then proceed along path 'Circle 6' to the process flow of FIG. 21.

Figure 21:
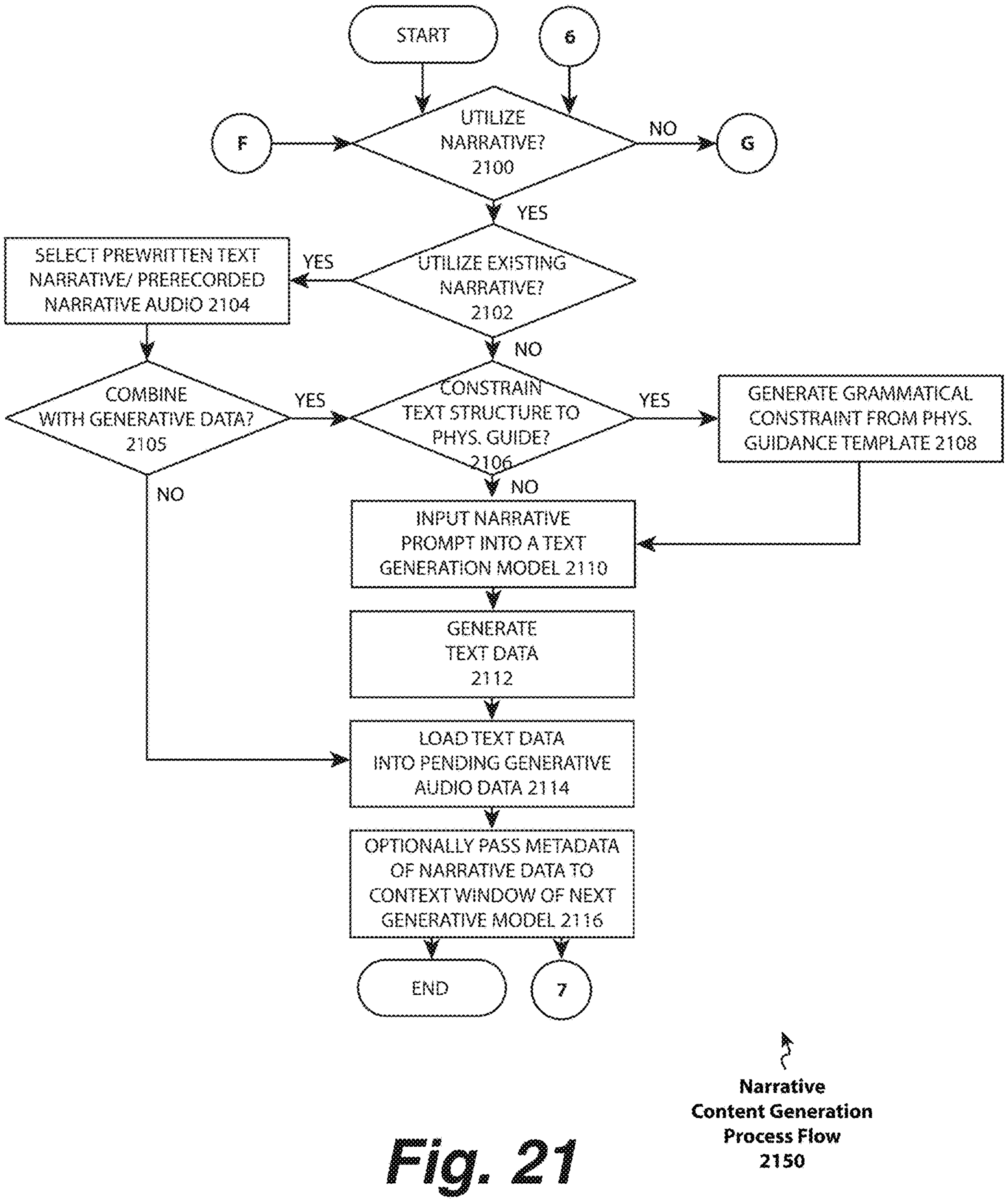
FIG. 21 illustrates a narrative content generation process flow, according to one or more embodiments.

FIG. 21 illustrates a narrative content generation process flow 2150, which may initiate at operation 2100 and/or may be a continuation from the process flow of FIG. 20. For example, operation 2100 may be a continuation from operation 2016 along path 'Circle 6' in the case that physiological guidance was utilized, or may be a continuation from operation 2000 along path 'Circle F' in which case physiological guidance was not utilized.

Operation 2100 may determine if narrative is to be generated, for example in response to a pending content generation request 700. For example, it may be determined whether a narrative prompt 730 may be present within the prompts 702 that may be stored within a pending session RAG data 124 and/or a request for narrative was otherwise included in the audio generation request 701 (including for example recorded narrative audio 520 and/or prewritten narrative text 530). If no narrative is to be utilized, operation 2100 may proceed along path 'Circle G' to the process flow of FIG. 22. If narrative is to be generated, operation 2100 may proceed to operation 2102.

Operation 2102 may determine whether the existing narrative data is to be utilized. If existing narrative is to be utilized (e.g., prerecorded, preexisting, and/or pre-written), operation 2102 may proceed to operation 2104. Operation 2104 may select prewritten narrative text 530 and/or recorded narrative audio 520 that is responsive to the audio generation request 701. For example, the user 100 may have requested a specific sleep story, encyclopedia entry, or other narrative that was already recorded by a human voice and/or may be text renderable in human speech. Operation 2104 may then proceed to operation 2105, which may determine if the preexisting narrative data is to be utilized in conjunction with further narrative generation, in which case operation 2105 may proceed to operation 2110 and, if not, operation 2105 may proceed to operation 2114.

Returning to operation 2102, if existing narrative data is not utilized, operation 2102 may proceed to operation 2106. Operation 2106 may determine whether the narrative text to be generated should be constrained in text structure (e.g., sentence length, sentence syllables, grammatical structure, and/or syntactic structure) according to the physiological guidance template. For example, the narrative text and/or its speech rendering may be constrained such that emphasis, words, or punctuation falls on or near physiological guidance cues. As just one example, an entire sentence may be read over 4 seconds when the user 100 is to breath in, a sentence may be read over 7 seconds when the user 100 is to hold their breath, and a sentence being read over 8 seconds when the user is to exhale. In one or more embodiments, the text data 830 may be constrained such that rendering into speech may likely fall within such temporal constraints, as may be further adjusted during speech rendering. If the narrative text is to be constrained, operation 2106 may proceed to operation 2108, which may generate grammatical constraint from the physiological guidance template, then proceed to operation 2110. Operation 2110 may be similarly arrived at from operation 2106 if no physiological constraint is to be added.

Operation 2110 inputs a narrative prompt 730 (and/or preexisting narrative data selected in operation 2104 or a description thereof) into a text generation model 130, which may include one or more artificial neural networks, for example as shown and described in conjunction with the embodiment of FIG. 1C. Operation 2112 may then proceed to operation 2112 which may generate the text data 830, for example as an output of the text generation model 130. Operation 2112 may then load the text data 830 into a pending generative audio data to be rendered and/or integrated, for example a temporary data storage container storing the outputs 810 as shown and described in conjunction with the embodiment of FIG. 1C. Operation 2116 may then optionally pass metadata of the narrative data (e.g., whether preexisting or generative) to the context window 126 of a next generative content model 120 to be utilized (e.g., ambient sound generation). Passing of the metadata to the context window 126 of the next generative content model 120 to be applied may assist in stylistic and/or structural coordinate of each generative aspect when serially created. Operation 2116 may terminate or may proceed to the process flow of FIG. 22 along path 'Circle 7'.

Figure 22:
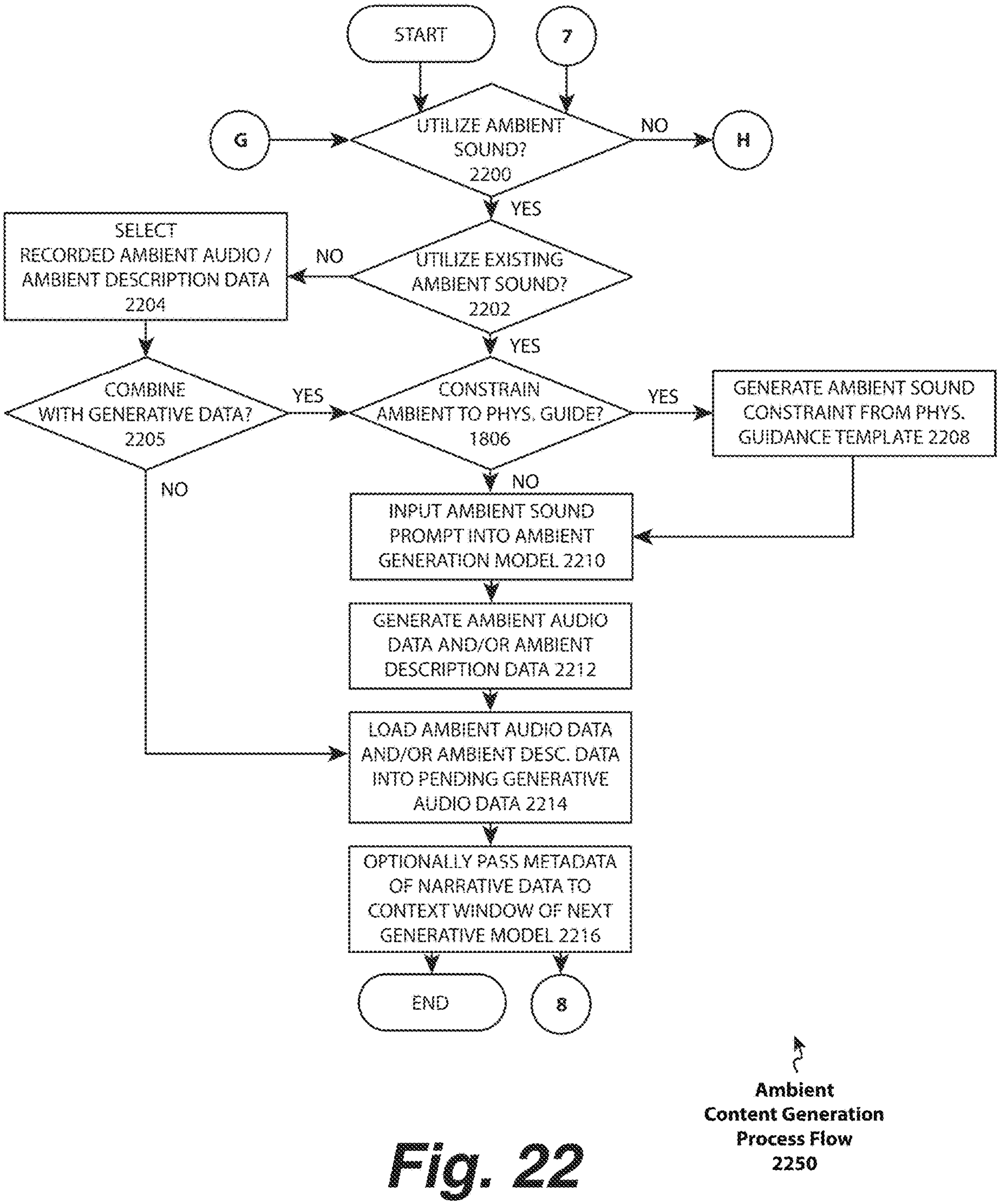
FIG. 22 illustrates an ambient content generation process flow, according to one or more embodiments.

FIG. 22 illustrates an ambient content generation process flow 2250, which may initiate at operation 2200 and/or may be a continuation from the process flow of FIG. 21. According to one or more embodiments, for example, operation 2200 may be a continuation from operation 2116 along path 'Circle 7' in the case that narrative was utilized, or may be a continuation from operation 2100 along path 'Circle G' in such case narrative was not utilized.

Operation 2200 may determine if ambient sound is to be utilized, for example in response to a pending content generation request 700. For example, it may be determined whether an ambient sound prompt 750 may be present within the prompts 702 and/or a request for ambient sound was otherwise included in the audio generation request 701 (including for example, a request for recorded ambient audio 550 and/or a description of preexisting ambient data which can be rendered into audio). If no ambient sound is to be utilized, operation 2200 may proceed along path 'Circle H' to the process flow of FIG. 23. If ambient sound is to be utilized, operation 2200 may proceed to operation 2202.

Operation 2102 may determine whether the existing ambient sound data is to be utilized as the ambient sound. If existing ambient sound is to be utilized (e.g., prerecorded, preexisting, and/or pre-described for rendering), operation 2202 may proceed to operation 2204. Operation 2204 may select recorded ambient audio 550, and/or a description of ambient sound that can be rendered into audio, either or both of which are responsive to the audio generation request 701. For example, the user 100 may have requested a specific ambient sound or soundscape that was previously formulated, synthesized, and/or recorded. Operation 2204 may then proceed to operation 2205, which may determine if the preexisting ambient sound data is to be utilized in conjunction with further ambient sound generation, in which case operation 2205 may proceed to operation 2210 and, if not, operation 2205 may proceed to operation 2214.

Returning to operation 2202, where existing ambient data is not utilized, operation 2202 may proceed to operation 2206. Operation 2206 may determine whether the ambient audio to be generated should be constrained according to the physiological guidance template. For example, the description of ambient sound and/or the ambient audio may be constrained such that ambient sounds or portions thereof occur on or near physiological guidance cues. As just one example: the sound of an ocean wave may be defined to break over 4 seconds when the user 100 is to breath in; silence or the sound of the resolving wave may be defined to occur over 7 seconds when the user 100 is to hold their breath; and the sound of withdrawing water may be defined to occur over 8 seconds when the user is to exhale. If the ambient sound is to be constrained, operation 2206 may proceed to operation 2208, which may generate an ambient sound constraint from the physiological guidance template, then proceed to operation 2210. Operation 2210 may be similarly arrived at from operation 2206 if no physiological constraint is to be added.

Operation 2210 inputs an ambient sound prompt 750 (and/or preexisting recorded ambient audio 550 or a description thereof) into an ambient sound generation model 150, which may include one or more artificial neural networks, for example as shown and described in conjunction with the embodiment of FIG. 1C. Operation 2210 may then proceed to operation 2212 which may generate the ambient audio data 850, for example as an output of the ambient sound generation model 150. Operation 2212 may then load the ambient audio data 850 into a pending generative audio data to be rendered and/or integrated, for example within a temporary data storage container storing the outputs 810 as shown and described in conjunction with the embodiment of FIG. 1C. Operation 2216 may then optionally pass metadata of the ambient audio data (e.g., whether preexisting or generative) to the context window 126 of a next generative content model 120 to be utilized (e.g., music generation). As described above in conjunction with the embodiment of FIG. 21, passing of metadata to the context window 126 of the next generative content model 120 to be applied may assist in stylistic and/or structural coordination of each generative aspect when serially created. Operation 2116 may then terminate, or may proceed to the process flow of FIG. 23 along path 'Circle 8'.

FIG. 23 illustrates a music content generation process flow 2350, which may initiate at operation 2300 and/or may be a continuation from the process flow of FIG. 22. For example, operation 2300 may be a continuation from operation 2216 along path 'Circle 8' if ambient sound was utilized, or may be a continuation from operation 2200 along path 'Circle H' in such case that ambient sound was not utilized.

Operation 2300 may determine if music is to be utilized, for example in response to a pending content generation request 700. For example, it may be determined whether a music prompt 740 may be present within the prompts 702 that may be stored within a pending session RAG data 124 and/or a request for music was otherwise included in the audio generation request 701 (including, for example, recorded music audio 540 and/or a description of preexisting music data which can be rendered into music audio). If no music is to be utilized, operation 2300 may proceed along path 'Circle I' to the process flow of FIG. 24. If music is to be utilized, operation 2300 may proceed to operation 2302.

Operation 2302 may determine whether the existing music data is to be utilized as the music. If existing music data is to be utilized (e.g., prerecorded, preexisting, and/or pre-described for rendering), operation 2302 may proceed to operation 2304. Operation 2304 may select recorded music audio 540, and/or a description of music sound that can be rendered into audio (e.g., a MIDI file or other similar format), that are responsive to the audio generation request 701. For example, the user 100 may have requested a specific musical track that was previously formulated, synthesized, and/or recorded. Operation 2304 may then proceed to operation 2305, which may determine if the preexisting music data is to be utilized in conjunction with further music generation, in which case operation 2305 may proceed to operation 2310 and, if not, operation 2305 may proceed to operation 2314.

Returning to operation 2302, if existing music audio is not utilized, operation 2302 may proceed to operation 2306. Operation 2306 may determine whether the music audio to be generated should be constrained according to the physiological guidance template. For example, the description of music and/or the music audio may be constrained such that music, musical notes, elements of music, or portions thereof may be rendered on or near physiological guidance cues. If the music audio is to be constrained, operation 2306 may proceed to operation 2308, which may generate musical constraint from the physiological guidance template, then proceed to operation 2310. The constraint can be a text description of the constraint, and/or other data usable to scaffold or steer the output of an ANN. Operation 2310 may be similarly arrived at from operation 2306 if no physiological constraint is to be added.

Operation 2310 inputs a music prompt 740 (and/or recorded music audio 540 or a description thereof) into a music generation model 140, which may include one or more artificial neural networks, for example as shown and described in conjunction with the embodiment of FIG. 1C. Operation 2312 may then proceed to operation 2312 which may generate the music audio data 840, for example as an output of the music generation model 140. Operation 1312 may then load the music audio data 840 into a pending generative audio data to be rendered and/or integrated, for example a temporary data storage container storing the outputs 810, as shown and described in conjunction with the embodiment of FIG. 1C. Operation 2314 may terminate, or may proceed to the process flow of FIG. 24 along path 'Circle 9'.

Figure 24:
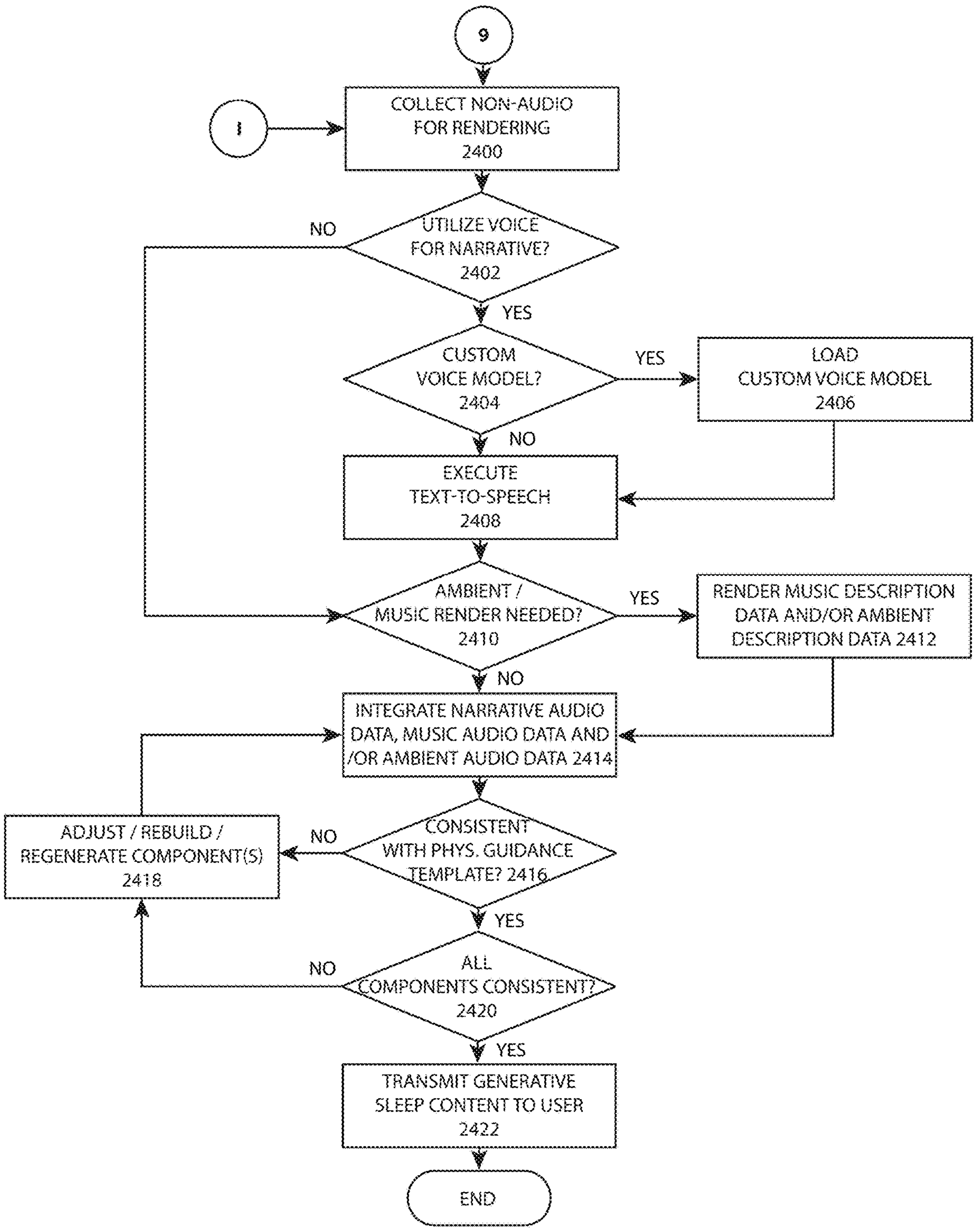
FIG. 24 illustrates a content integration process flow, according to one or more embodiments.

FIG. 24 illustrates a content integration process flow 2450, according to one or more embodiments. Operation 2400 may continue from the process flow of FIG. 23, for example from operation 2300 if no music was utilized along path 'Circle I', and from operation 2314 if music was utilized along path 'Circle 9' if music was utilized. Operation 2400 collects non-audio components for rendering, for example generative outputs describing ambient sound or music to be rendered, text data 830 to be turned into speech, and/or physiological guidance templates not already incorporated into one or more of the other generative outputs. Operation 2402 may determine if voice is to be utilized for rendering any text data 830, in which case operation 2404 may proceed to operation 2404. If no voice is to be utilized (e.g., there is no narrative text within the generative sleep content request 700 and/or the narrative is already available as prerecorded audio), operation 2402 may proceed to operation 2410. Operation 2404 may determine if a custom voice model is to be utilized (e.g., the custom voice model 194), in which case operation 2404 may proceed to operation 2406 which may load the custom voice model 194. Operation 2408 may then execute the text-to-speech rendering of the text data 830 (e.g., via the text-to-speech model 192), including any custom voice model 194 loaded in operation 2406.

Operation 2410 may determine if any of the ambient sound and/or music may need to be rendered. For example, audio rendering may be needed for a description of ambient sound (e.g., the ambient composition data 852) and/or description of music (e.g., the music description data 842) that may be an output of a generative content model 120 and/or a preexisting description. If ambient sound and/or music rendering is to be utilized, operation 2410 may proceed to operation 2412, which may render the ambient composition data 852 and/or the music description data 842. For example, rendering may occur in whole or in part by assigning music notes, tones, complex waveforms, soundbites, and/or ambient sounds, to each portion of the described ambient sound or music such that a digital-to-analog converter can generate sound signals from audio data. Operation 2412 may then proceed to operation 2414. If no ambient and/or music rendering is needed (e.g., the ambient sound is already defined as ambient audio data 850 and/or the music is already defined as the music audio data 840), then operation 2410 may also proceed to operation 2414.

Operation 2414 may integrate the narrative audio data 832, the music audio data 840, and/or the ambient audio data 850. For example, integration may occur through overlay of each of the audio data, followed by compilation and/or "flattening" into a single audio file. Other methods for integration are shown and described in conjunction with the embodiment of FIG. 8 and throughout the present embodiments. The output of operation 2414 may be a tentative and/or preliminary generation of generative sleep content 800, according to one or more embodiments.

Operation 2416 determines whether the tentative generative sleep content 800 is consistent with any physiological guidance template, for example to verify that the rendering and/or any adjustments made in integration still define accurate physiological guidance cues in line with the template. If not, operation 2416 may proceed to operation 2418, which may adjust, rebuild, and/or regenerate one or more components of the generative sleep content 800. For example, re-integration including re-alignment may be attempted. However, in one or more embodiments, operation 2418 may re-submit one or more of the generative content model 120 outputs (e.g., the outputs 810) back to their respective generative content model 120 to be re-generated, including, if needed, utilizing additional context for all other aspects with which integration is intended to potentially improve integration compatibility (e.g., narrative, physiological guidance, ambiance, music). Upon successful integration constant with the physiological guidance template, operation 2416 may proceed to operation 2420, which may perform a general determination of consistency and/or compatibility of the integrated product. If a component or element has been improperly integrated, or otherwise fails quality control requirements, operation 2420 may return to operation 2418. If all components appear consistent and properly integrated, operation 2420 may advance to operation 2420. Operation 2410 may then transmit the generative sleep content 800 to the user 100, for example over the network 106 to a device 650 of the user 100 and/or the earphones 600 to be utilized in assisting with initiating or maintaining sleep.

An advantage of one or more of the present embodiments includes generation of custom sleep audio particular to the needs or desires of the user 100. Another advantage of one or more of the embodiments includes generation of custom sleep audio which includes effective structure but novel implementation and/or detail so that a user 100 does not get bored while still having experienced effective content at inducing or maintaining sleep.

An advantage of one or more of the present embodiments includes integrating two or more of physiological guidance, narrative, music, and/or ambient sounds. Another advantage of one or more of the present embodiments includes incorporating physiological guidance into narrative audio, music audio, and/or ambient audio. Yet another advantage of one or more of the present embodiments may be adjusting population-wide content, such as a standard physiological guidance template, for the individual needs and desires of a user.

An advantage of one or more of the present embodiments includes an easily used voice interface 104 that can serve some or all of the sleep needs of the user 100, including without limitation: control over sleep-assisting hardware such as earbuds, reporting sleep data and sleep metrics, providing general information about sleep, providing sleep improvement interventions 180 for actionable plans related to sleep improvement, and/or for generation of custom sleep assistance audio 102. From the perspective of the user 100, such a capable voice interface 104 (and technology supporting it) may reduce cognitive load on the user 100 when the user is trying to sleep, provide a natural language interface that requires little learning to achieve the complete benefit thereof, and provides actionable information at opportune times. An advantage of one or more of the embodiments includes flexible determination of when and how to present sleep data, sleep interventions, sleep metrics, and/or generative sleep content 800 to the user 100 to maximize the probability for helping the user initiate or maintain sleep. An advantage of one or more of the present embodiments also includes a single source for both generative sleep content 800 and sleep improvement interventions 180, including optionally recommending sleep assistance audio 102 as part of a sleep improvement intervention 180.

In one or more embodiments, an advantage includes the capability to evaluate the effectiveness of sleep assistance audio 102, including evaluation of the prompts 702 used to generate any generative sleep content 800 used as model input and/or the elements or characteristics of the generative sleep content 800 as model outputs. In one or more embodiments, an advantage also includes (i) determining effectiveness for sleep assistance audio 102 with respect to a single user, and/or (ii) determining effectiveness for sleep assistance audio 102 from one user 100 to improve generation of sleep assistance audio for other users 100. In one or more embodiments, an advantage also includes determining effectiveness in order to build training data to augment, train, re-train, fine-tune, specialize, one or more AI models, artificial neural networks, and/or large language models.

In one or more or more embodiments, an advantage includes the capability to evaluate the sleep improvement interventions 180, including prompts used as model input and/or the elements, steps, or characteristics generated as model outputs. In one or more embodiments, an advantage also includes (i) determining effectiveness for sleep improvement interventions 180 with respect to a single user, and/or (ii) determining effectiveness for sleep improvement interventions 180 from one user 100 to improve sleep improvement interventions 180 generated for other users 100. In one or more embodiments, an advantage also includes determining effectiveness in order to build better training dataset to augment, train, re-train, fine-tune, and/or specialize one or more AI models, artificial neural networks, and/or large language models.

Yet another advantage of one or more embodiments includes the efficient mediation of specialized models for producing common auditory aspects to assisting sleep: physiological guidance, narrative, music, and ambient sound. Similarly, an advantage of one or more of the present embodiments includes serialization and context-passing between and among generative models (e.g., the generative content models 120) such that the probability of successful integration of results from disparate AI models is achieved.

Still another advantage of one or more of the present embodiments includes influencing outputs of AI models, such as an ANN, CNN, RNN, KAN, and/or LLM through feedback of the effectiveness of the inputs and outputs and producing physiologically effective content, whether sleep assistance intervention 102 and/or a sleep improvement intervention 180.

Another advantage of one or more of the present embodiments includes a workable coordination of two or more AI models for the purpose of generating sleep content, including generative audio and/or sleep improvement interventions 180, that results in steady and continuous improvement in the sleep quality of a user 100.

Although the present embodiments have been described with reference to specific example embodiments, it will be evident that various modifications and changes may be made to these embodiments without departing from the broader spirit and scope of the various embodiments. For example, the various devices, engines, agent, routines, and modules described herein may be enabled and operated using hardware circuitry (e.g., CMOS based logic circuitry), firmware, software, or any combination of hardware, firmware, and software (e.g., embodied in a non-transitory machine-readable medium). For example, the various electrical structure and methods may be embodied using transistors, logic gates, and electrical circuits (e.g., application specific integrated circuitry (ASIC) and/or Digital Signal Processor (DSP) circuitry).

In addition, it will be appreciated that the various operations, processes, and methods disclosed herein may be embodied in a non-transitory machine-readable medium and/or a machine-accessible medium compatible with a data processing system (e.g., the sleep assistance server 200, the generative content server 300, the profile server 400, the preexisting content server 500, the earphones 600, the device 650, etc.). Accordingly, the specification and drawings are to be regarded in an illustrative rather than a restrictive sense.

The structures in the figures such as the engines, routines, and modules may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the preceding disclosure.

Embodiments of the invention are discussed above with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures.

From reading the present disclosure, other variations and modifications will be apparent to persons skilled in the art. Such variations and modifications may involve equivalent and other features which are already known in the art, and which may be used instead of or in addition to features already described herein.

Although claims have been formulated in this application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any claim and whether or not it mitigates any or all of the same technical problems.

Features which are described in the context of separate embodiments may also be provided in combination in a single embodiment. Conversely, various features which are, for brevity, described in the context of a single embodiment, may also be provided separately or in any suitable sub-combination. The applicants hereby give notice that new claims may be formulated to such features and/or combinations of such features during the prosecution of the present application or of any further application derived therefrom.

References to "one embodiment," "an embodiment," "example embodiment," "various embodiments," "one or more embodiments," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least one or more embodiments of the invention" includes the stated particular feature, structure, or characteristic.

The enumerated listing of items does not imply that any or all of the items are mutually exclusive, unless expressly specified otherwise.

It is understood that the use of a specific component, device and/or parameter names are for example only and not meant to imply any limitations on the invention. The invention may thus be implemented with different nomenclature and/or terminology utilized to describe the mechanisms, units, structures, components, devices, parameters and/or elements herein, without limitation. Each term utilized herein is to be given its broadest interpretation given the context in which that term is utilized.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant (PDA); a portable telephone; a smartphone, application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, a system on a chip, or a chip set; a data acquisition device; an optical computer; a quantum computer; a biological computer; and generally, an apparatus that may accept data, process data according to one or more stored software programs, generate results, and typically include input, output, storage, arithmetic, logic, and control units.

Those of skill in the art will appreciate that where appropriate, one or more embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Where appropriate, embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The example embodiments described herein can be implemented in an operating environment comprising computer-executable instructions (e.g., software) installed on a computer, in hardware, or in a combination of software and hardware. The computer-executable instructions can be written in a computer programming language or can be embodied in firmware logic. If written in a programming language conforming to a recognized standard, such instructions can be executed on a variety of hardware platforms and for interfaces to a variety of operating systems. Although not limited thereto, computer software program code for carrying out operations for aspects of the present invention can be written in any combination of one or more suitable programming languages, including an object oriented programming languages and/or conventional procedural programming languages, and/or programming languages such as, for example, Hypertext Markup Language (HTML), Dynamic HTML, Extensible Markup Language (XML), Extensible Stylesheet Language (XSL), Document Style Semantics and Specification Language (DSSSL), Cascading Style Sheets (CSS), Synchronized Multimedia Integration Language (SMIL), Wireless Markup Language (WML), Java™, Jini™, C, C++, Smalltalk, Perl, UNIX Shell, Visual Basic or Visual Basic Script, Virtual Reality Markup Language (VRML), ColdFusion™ or other compilers, assemblers, interpreters or other computer languages or platforms.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

A network is a collection of links and nodes (e.g., multiple computers and/or other devices connected together) arranged so that information may be passed from one part of the network to another over multiple links and through various nodes. Examples of networks include the Internet, the public switched telephone network, the global Telex network, computer networks (e.g., an intranet, an extranet, a local-area network, or a wide-area network), wired networks, and wireless networks.

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the figures illustrate the architecture, functionality, and operation of possible implementations of systems, methods and computer program products according to various embodiments. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

It will be readily apparent that the various methods and algorithms described herein may be implemented by, e.g., appropriately programmed general purpose computers and computing devices. Typically a processor (e.g., a microprocessor) will receive instructions from a memory or like device, and execute those instructions, thereby performing a process defined by those instructions. Further, programs that implement such methods and algorithms may be stored and transmitted using a variety of known media.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The functionality and/or the features of a device may be alternatively embodied by one or more other devices which are not explicitly described as having such functionality/features. Thus, other embodiments of the present invention need not include the device itself.

The term "computer-readable medium" as used herein refers to any medium that participates in providing data (e.g., instructions) which may be read by a computer, a processor or a like device. Such a medium may take many forms, including but not limited to, non-volatile media, volatile media, and transmission media. Non-volatile media include, for example, optical or magnetic disks and other persistent memory. Volatile media include dynamic random access memory (DRAM), which typically constitutes the main memory. Transmission media include coaxial cables, copper wire and fiber optics, including the wires that comprise a system bus coupled to the processor. Transmission media may include or convey acoustic waves, light waves and electromagnetic emissions, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, removable media, flash memory, a "memory stick", any other memory chip or cartridge, a carrier wave as described hereinafter, or any other medium from which a computer can read.

Where databases are described, it will be understood by one of ordinary skill in the art that (i) alternative database structures to those described may be readily employed, (ii) other memory structures besides databases may be readily employed. Any schematic illustrations and accompanying descriptions of any sample databases presented herein are exemplary arrangements for stored representations of information. Any number of other arrangements may be employed besides those suggested by the tables shown. Similarly, any illustrated entries of the databases represent exemplary information only; those skilled in the art will understand that the number and content of the entries can be different from those illustrated herein. Further, despite any depiction of the databases as tables, an object-based model could be used to store and manipulate the data types of the present invention and likewise, object methods or behaviors can be used to implement the processes of the present invention.

Embodiments of the invention may also be implemented in one or a combination of hardware, firmware, and software. They may be implemented as instructions stored on a machine-readable medium, which may be read and executed by a computing platform to perform the operations described herein.

More specifically, as will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Unless specifically stated otherwise, and as may be apparent from the following description and claims, it should be appreciated that throughout the specification descriptions utilizing terms such as "processing," "computing," "calculating," "determining," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The term "processor" may refer to any device or portion of a device that processes electronic data from registers and/or memory to transform that electronic data into other electronic data that may be stored in registers and/or memory. A "computing platform" may comprise one or more processors.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied.

It will be further apparent to those skilled in the art that at least a portion of the novel method steps and/or system components of the present invention may be practiced and/or located in location(s) possibly outside the jurisdiction of the United States of America (USA), whereby it will be accordingly readily recognized that at least a subset of the novel method steps and/or system components in the foregoing embodiments must be practiced within the jurisdiction of the USA for the benefit of an entity therein or to achieve an object of the present invention.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Having fully described at least one embodiment of the present invention, other equivalent or alternative methods of implementing the sleep assistance server 200, the generative content server 300, the profile server 400, the preexisting content server 500, the earphones 600, the device 650, the generative content models 120, and/or the sleep assistance model 115, according to the present invention will be apparent to those skilled in the art. Various aspects of the invention have been described above by way of illustration, and the specific embodiments disclosed are not intended to limit the invention to the particular forms disclosed. The particular implementation of the sleep assistance server 200, the generative content server 300, the profile server 400, the preexisting content server 500, the earphones 600, the device 650, the generative content models 120, and/or the sleep assistance model 115 may vary depending upon the particular context or application. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims. The following claims are hereby incorporated into the detailed description, with each claim standing on its own as a separate embodiment.

What is claimed is:

1. A system for generating customized audio for increasing effectiveness of relaxation and/or sleep, the system comprising:

a network;

an earbud wearable by a user comprising:

a speaker, a microphone, a processor of the earbud, a memory of the earbud that is a non-transient computer readable memory of the earbud, a wireless network interface controller communicatively coupled to the network, and a request generation routine comprising computer readable instructions that when executed on the processor of the earbud generate an audio generation request through a voice interface implemented on the speaker and the microphone;

a sleep assistance server communicatively coupled to the network, comprising:

a processor of the sleep assistance server,
a memory of the sleep assistance server that is a non-transient computer readable memory of the sleep assistance server,
a request agent comprising computer readable instructions that when executed receive the audio generation request,
a content prompt extraction routine comprising computer readable instructions that when executed:
parse the audio generation request to extract a narrative prompt, and
store the narrative prompt in the memory of the sleep assistance server; and
a generative content server communicatively coupled to the network, comprising:
a processor of the generative content server,
a memory of the generative content server,
a text generation routine comprising computer readable instructions that when executed:
input the narrative prompt into a text generation model comprising an artificial neural network of the text generation model,
wherein the artificial neural network comprising a plurality of nodes comprising a set of input nodes, a set of hidden nodes, and a set of output nodes, and
generate a text data as the output of the artificial neural network of the text generation model,
a voice generation routine comprising computer readable instructions that when executed:
input the text data into a text-to-speech model, and
store a narrative audio data as an output of the text-to-speech model,
a content integration routine comprising computer readable instructions that when executed generate a generative audio data comprising an overlay of the narrative audio data and at least one of a music audio data, a physiological guidance data, and an ambient audio data, and
a generative content engine comprising computer readable instructions that when executed transmit the generative audio data to the earbud of the user to assist the user in achieving at least one of relaxation and sleep through the customized audio.

2. The system of claim 1,
wherein the earbud further comprising:
an inertial measurement unit, and
a physiological signal agent comprising computer readable instructions that when executed gather a physiological data of the user from the inertial measurement unit of the earbud worn by the user while the generative audio data plays sound on the speaker of the earbud,
wherein the physiological data comprising at least one of motion of the user comprising a heartbeat, a respiration, and a macro movement; and
wherein the sleep assistance server further comprising:
a state monitoring routine comprising computer readable instructions that when executed utilize the physiological data gathered from the inertial measurement unit to determine the user is in at least one of a sleep state and an awake state over a time period,
a sleep metric routine comprising computer readable instructions that when executed determine one or more sleep metrics for a sleep session comprising a sleep onset latency value, a length of a sleep period during the time period, a ratio of the sleep period to an awake period during the time period, a number of rapid eye movement (REM) periods, a length of REM periods, a number of Non-REM periods, a length of Non-REM periods, a number of interstitial awake periods, and a length of the awake period during the time period, and
a sleep content evaluation routine comprising computer readable instructions that when executed:
extract one or more generative elements of at least one of the narrative audio data and the text data associated with the narrative audio data, and
store one or more generative elements in association with an effectiveness value and an effectiveness rating based on the one or more sleep metrics.

3. The system of claim 1, wherein the generative content server further comprising:
a general augmentation routine comprising computer readable instructions that when executed:
querying a general augment data comprising at least one of general augment narrative data, general augment music data, general augment ambient data, and general augment voice data,
extract a subset of the general augment data based on textual association with the audio generation request, and
load the subset of the general augment data into at least one of an input prompt of an artificial neural network and a context window of the artificial neural network,
wherein the input prompt comprises at least one of the narrative prompt, a music prompt, and an ambient prompt, and
wherein the artificial neural network is at least one of an artificial neural network of the text generation model.

4. The system of claim 1, further comprising:
a specific augmentation routine comprising computer readable instructions that when executed:
query a user specific augment data comprising at least one of user augment narrative data, user augment music data, user augment ambient data, and user augment voice data,
extract a subset of the user specific augment data relevant to the audio generation request,
overwrite at least some of the subset of the general augment data within at least one of the input prompt of the artificial neural network and a context window of the artificial neural network, and
load the subset of the user specific augment data into at least one of the input prompt of the artificial neural network and the context window of the artificial neural network.

5. The system of claim 1,
wherein the generative content server further comprising:
a model training routine comprising computer readable instructions that when executed retrain the artificial neural network of the text generation model based on at least one of the effectiveness value and the effectiveness rating,
wherein retraining comprises adjusting a parameter of at least one of the artificial neural network of the text generation model,
wherein adjusting the parameter comprising modifying a node weight of an artificial neural network (ANN) node,
wherein tuning the parameter adjusts a weight value of at least one node of the set of input nodes, the set of hidden nodes, the set of output nodes, wherein the text generation model is a large language model, and wherein the text data input into a voice synthesizer comprising a custom voice model; and a guidance prioritization subroutine comprising computer readable instructions that when executed constrain the output of the artificial neural network of a narrative generation model to produce the text data in which a text clause of the text data is temporally associable with a physiological guidance element of a physiological guidance template, wherein the text-to-speech model generates the narrative audio such that a voiceover of the text data is temporally associated with a physiological guidance element.

6. A method for generating customized audio for increasing effectiveness of relaxation and/or sleep, the method comprising:

receiving an audio generation request through a voice interface collected on a microphone of an earbud;

parsing the audio generation request to extract a narrative prompt and a physiological guidance prompt;

storing the narrative prompt in a computer readable memory;

determining a narrative modifier from the audio generation request comprising at least one of a narrative style description and a narrative genre description;

inputting the narrative prompt into a text generation model comprising an artificial neural network of the text generation model;

generating a text data as an output of the artificial neural network of the text generation model;

inputting the text data into a text-to-speech model;

outputting a narrative audio data;

storing the physiological guidance prompt in the computer readable memory;

determining a physiological guidance modifier from the audio generation request comprising a physiological guidance type, wherein the physiological guidance type comprising at least one of a respiration rate, a respiration pattern, and a heart rate;

inputting the physiological guidance prompt into a physiological guidance model comprising an artificial neural network of the physiological guidance generation model, generating a physiological guidance template as an output of the artificial neural network of the physiological guidance model;

wherein the physiological guidance comprising one or more physiological generating a generative audio data comprising an overlay of the narrative audio data and audio generated from the physiological guidance template; and transmitting the generative audio data to the earbud of a user to assist the user in achieving at least one of relaxation and sleep through the customized audio.

7. The method of claim 6, further comprising:

parsing the audio generation request to further determine if a music prompt is included within the audio generation request;

generating, if the music prompt was not present when the audio generation request was parsed, the music prompt by inputting the narrative prompt into a text-music relation model relating a text to at least one of musical elements, a music style description, and a music genre description;

optionally extracting a music modifier comprising at least one of a music filter, the music style description, and the music genre description;

storing in the computer readable memory the music prompt and optionally at least one of the music style description, the music genre description, and the music filter;

inputting the music prompt into a music generation model comprising an artificial neural network of the music generation model, wherein the music generation model trained with training data comprising associations between text tokens and musical elements; and generating a music audio data as an output of the artificial neural network of the music generation model, wherein the generative audio data further comprising an overlay of the music audio data.

8. The method of claim 7, further comprising:

parsing the audio generation request to further determine an ambient sound prompt;

storing the ambient sound prompt in the computer readable memory;

receiving an ambient modifier comprising at least one of an ambient filter and an ambient style description;

inputting the ambient sound prompt and the ambient modifier into an ambient sound generation model comprising an artificial neural network of the ambient sound generation model, wherein the ambient sound generation model trained with training data comprising associations between text tokens and sound elements; and generating an ambient audio data as an output of the artificial neural network of the ambient generation model, wherein the generative audio data further comprising an overlay of the ambient audio data.

9. The method of claim 8, further comprising:

querying a general augment data comprising at least one of general augment narrative data, general augment music data, general augment ambient data, and general augment voice data;

extracting a subset of the general augment data based on textual association with the audio generation request; and loading the subset of the general augment data into at least one of an input prompt of an artificial neural network and a context window of the artificial neural network, wherein the input prompt comprises at least one of the narrative prompt, the music prompt, and the ambient prompt, and wherein the artificial neural network is at least one of an artificial neural network of the text generation model, an artificial neural network of the music generation model, and an artificial neural network of the ambient sound generation model.

10. The method of claim 9, further comprising:

querying a user specific augment data comprising at least one of user augment narrative data, user augment music data, user augment ambient data, and user augment voice data, extracting a subset of the user specific augment data relevant to the audio generation request;

overwriting at least some of the subset of the general augment data within at least one of the input prompt of the artificial neural network and the context window of the artificial neural network; and loading the subset of the user specific augment data into at least one of the input prompt of the artificial neural network and the context window of the artificial neural network.

11. The method of claim 10, further comprising:

constraining the output of the artificial neural network of the ambient sound generation model to produce an ambient audio data in which an ambient element is temporally associated with a physiological guidance element;

constraining the output of the artificial neural network of the music generation model to produce the music audio data in which a musical element is temporally associated with a physiological guidance element; and constraining the output of the artificial neural network of the text generation model to produce the text data in which a text clause of the text data is temporally associable with a physiological guidance element, wherein the text-to-speech model generates the narrative audio such that a voiceover of the text data is temporally associated with a physiological guidance element.

12. The method of claim 11, further comprising:

gathering a physiological data of the user from a sensor of an earbud worn by the user while the generative audio data plays sound on a speaker of the earbud;

determining the user is in a sleep state;

determining one or more sleep metrics comprising a sleep onset latency value, a length of a sleep period during a time period, a ratio of the sleep period to an awake period during the time period, a number of rapid eye movement (REM) periods, a length of REM periods, a number of Non-REM periods, a length of Non-REM periods, a number of interstitial awake periods, and a length of the awake period during the time period;

extracting one or more generative elements of at least one of the generative audio data, the narrative audio data, the text data associated with the narrative audio data, the music audio data, the ambient audio data, and the one or more physiological guidance elements;

storing the one or more generative elements in association with an effectiveness value and an effectiveness rating; and retraining at least one of the artificial neural network of the text generation model, the artificial neural network of the music generation model, the artificial neural network of the physiological guidance model and the artificial neural network of the ambient generation model, wherein retraining comprises adjusting a parameter of at least one of the artificial neural network of the text generation model, the artificial neural network of the music generation model, and the artificial neural network of the physiological guidance model and the artificial neural network of the ambient generation model, and wherein adjusting the parameter comprising modifying a node weight of an artificial neural network (ANN) node.

13. The method of claim 12, further comprising:

querying a prerecorded audio comprising at least one of a recorded narrative audio, a recorded music audio, a recorded ambient audio, and a recorded physiological guidance audio, and integrating the prerecorded audio with the generative audio, wherein the artificial neural network each comprising a plurality nodes comprising a set of input nodes, a set of hidden nodes, and a set of output nodes, wherein tuning the parameter adjusts a weight value of at least one node of the set of input nodes, the set of hidden nodes, and the set of output nodes, wherein the text generation model is a large language model, and wherein the text data input into a voice synthesizer comprising a custom voice model.

* * * * *